United States Patent [19]

Oshima et al.

[11] Patent Number: 5,010,087

[45] Date of Patent: Apr. 23, 1991

[54] TRICYCLIC COMPOUNDS AND TXA$_2$ ANTAGONISTIC COMPOSITIONS THEREOF

[75] Inventors: Etsuo Oshima, Shizuoka; Hiroyuki Obase, Mishima; Akira Karasawa; Kazuhiro Kubo, both of Shizuoka; Ichiro Miki, Tokyo; Akio Ishii, Shizuoka, all of Japan

[73] Assignee: Kyowa Hakko Kogyo Co., Ltd., Tokyo, Japan

[21] Appl. No.: 381,330

[22] Filed: Jul. 18, 1989

Related U.S. Application Data

[62] Division of Ser. No. 255,485, Oct. 11, 1988, Pat. No. 4,882,351.

[30] Foreign Application Priority Data

Oct. 14, 1987 [JP] Japan .................. 62-259145

[51] Int. Cl.$^5$ .................. A61K 31/47; A61K 31/44; C07D 215/20; C07D 217/26
[52] U.S. Cl. .................. 514/307; 514/309; 514/310; 514/312; 514/313; 514/314; 514/337; 514/338; 514/346; 514/345; 514/347; 514/348; 514/349; 514/350; 514/352; 514/354; 514/355; 514/357; 514/422; 514/423; 514/424; 514/426; 514/427; 514/428; 514/429; 546/141; 546/743; 546/148; 546/149; 546/153; 546/162; 546/269; 546/285; 546/270; 546/274; 548/525; 548/526; 548/527
[58] Field of Search .............. 546/274, 270, 269, 285, 546/135, 143, 141, 148, 149, 153, 162; 548/525, 526, 527; 514/337, 338, 346–350, 352, 353, 354, 355, 357, 422–427, 310, 313, 309, 307, 310–314, 345

[56] References Cited

U.S. PATENT DOCUMENTS

| | | | |
|---|---|---|---|
| 3,354,155 | 11/1967 | Tretter | 260/240 |
| 3,420,851 | 1/1969 | Bloom et al. | 260/333 |
| 3,905,972 | 9/1975 | Dostert et al. | 548/528 |
| 4,282,365 | 8/1981 | Rokach et al. | 548/252 |
| 4,396,550 | 8/1983 | Takizawa et al. | 549/354 |
| 4,465,835 | 8/1984 | Takizawa et al. | 549/354 |
| 4,585,788 | 4/1986 | Helsley et al. | 514/450 |
| 4,596,804 | 6/1986 | Takizawa et al. | 514/25 |
| 4,749,703 | 6/1988 | Uno et al. | 514/253 |

FOREIGN PATENT DOCUMENTS

| | | |
|---|---|---|
| 0085870 | 8/1983 | European Pat. Off. |
| 188802 | 7/1986 | European Pat. Off. |
| 214779 | 3/1987 | European Pat. Off. |
| 0235796 | 9/1987 | European Pat. Off. |
| 139073 | 8/1983 | Japan |
| 227879 | 12/1984 | Japan |
| 152673 | 7/1986 | Japan |
| 152674 | 7/1986 | Japan |
| 152675 | 7/1986 | Japan |
| 152676 | 7/1986 | Japan |
| 257981 | 11/1986 | Japan |
| 153280 | 8/1987 | Japan |
| 1167263 | 2/1967 | United Kingdom |
| 8705014 | 2/1987 | World Int. Prop. O. |

OTHER PUBLICATIONS

Chemical Abstracts, vol. 105 (1986), abst. No. 60549g.
Chemical Abstracts, vol. 96 (1982), abst. No. 68848v.
J. Med. Chem. 19, 941 (1976), Ueno et al.
J. Med. Chem. 20, 1499, Aultz et al.
J. Med. Chem. 21, 633 (1978), Yoshioka et al.
Drugs, 13, 161 (1977), Pinder et al.
Arz.—Forsch., 13, 1039 (1963), Metvsova et al.
Arz.—Forsch., 14, 100 (1964), Benesova et al.

Primary Examiner—Joseph Paul Brust
Assistant Examiner—Jacqueline Haley
Attorney, Agent, or Firm—Fitzpatrick, Cella, Harper & Scinto

[57] ABSTRACT

Novel tricyclic compounds having a TXA$_2$-antagonizing activity represented by formula (I):

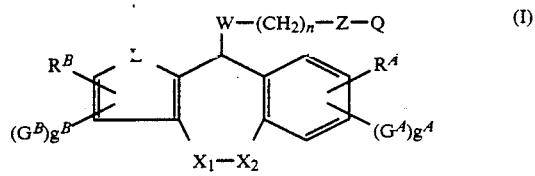

which strongly antagonize an action of thromboxane A$_2$ and are expected to have preventive and therapeutic effects on ischemica diseases, cerebro-vascular diseases, etc.

10 Claims, No Drawings

TRICYCLIC COMPOUNDS AND TXA₂ ANTAGONISTIC COMPOSITIONS THEREOF

This application is a division of application Ser. No. 255,485, filed Oct. 11, 1988 now U.S. Pat. No. 4,882,351.

BACKGROUND OF THE INVENTION

The present invention relates to novel tricyclic compounds which strongly antagonize an action of thromboxane A₂ (hereafter referred to as TXA₂).

It is hitherto known that TXA₂ strongly aggregates platelets and is a potent vasoconstrictor [cf. Arachidonic Acid Cascade and Drugs, edited by Shozo Yamamoto, Gendai Iryo Publishing Co., Ltd. (1958)]. Further TXA₂ is a powerful vasoconstrictor against bronchus and bronchial smooth muscle. Therefore, TXA₂ is considered to take part in pathological conditions over a wide range. The following diseases can be exemplified.

(1) Ischemic disease

For example, myocardial infarction, angina pectoris, and thrombosis (2) Cerebro-vascular disease For example, transient ischemic attack, migraine, cerebral hemorrhage, and cerebral infarction, (3) Peripheral vascular diseases and disease caused by unbalanced lipid.

For example, atherosclerosis, capillary convulsion, peripheral circulation disorders, hypertension, and pulmonary embolism (4) Inflammatory and allergic diseases For example, bronchial asthma, bronchitis, pneumonia, nephritis, and hepatitis (5) Shock (6) Cancer metastasis Accordingly, compounds that antagonize the action of TXA₂ are expected to have therapeutic effects in preventing or treating one or more of the diseases described above or other diseases involving TXA₂. Further where in drugs used for medical purposes heretofore, application thereof is limited due to side effects mediated by TXA₂ or assumed to be mediated by TXA₂, it is expected to alleviate the side effects by the use of compounds which antagonize the action of TXA₂.

As an antagonist of TXA₂, representative compounds are exemplified in Thrombosis Research, 44, 377 (1986). Furthermore, an indole compound having the following structure:

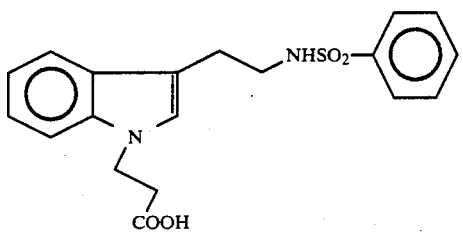

etc. is disclosed in Japanese Published Unexamined Patent Application No. 249960/1986 [West German Patent Application (DE) No. 3,514,696] and a compound having the following structure:

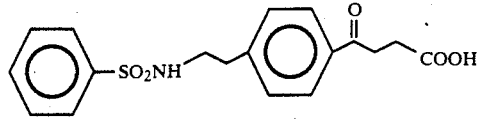

is disclosed in Japanese Published Unexamined Patent Application No. 212552/1986 [West German Patent Application (DE) No. 3,508,692]. These compounds are derivatives having a phenylsulfonamide group and exhibit an activity of antagonizing TXA₂.

On the other hand, among tricyclic compounds represented by the following formula:

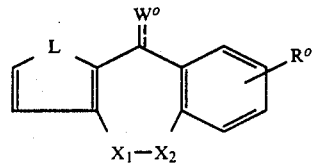

wherein L is —CH=CH—, $R^o$ as a substituent on the aromatic ring has carboxyl or a derivative thereof (for example, an ester, an amide, etc.; hereafter collectively referred to as carboxylic acid group) directly or via an alkylene chain, etc. and $W^o$ is hydrogen or a substituent such as oxo (=O), methylene (=CH₂), hydroxyl, alkoxyl, etc., oxepine derivatives wherein $X_1$—$X_2$=—CH₂O— are known to show antiinflammatory, antiallergic activities, etc. [J. Med. Chem., 19, 941 (1976); ibid., 20, 1499 (1977); ibid, 21, 633 (1978); U.S. Patent No. 4,282,36(Japanese Published Unexamined Patent Application No. 21679/1983); U.S. Pat. No. 4,585,788; Japanese Published Unexamined Patent Application Nos. 152673/1986; 152674/1986 and 152675/1986]. Further, it is also known that oxepine derivatives wherein $R^o$ is hydrogen or a substituent other than the carboxylic acid group, such as alkyl, alkoxyl, halogen, etc. and $W^o$ has an alkylaminoalkyl chain via hetero atom (—NH—, —O—, —S—, etc.) show antihistaminic, antiallergic, antiasthmatic, activities, etc. [Japanese Published Unexamined Patent Application Nos. 150083/1981 (U.S. Pat. Nos. 4,396,550 and 4,465,835); 139073/1982; 126883/1983 (EP 0085870A) and 227879/1984]. It is also known that derivatives such as oxepine or thiepine (wherein $X_1$—$X_2$ is —CH₂S—) wherein $W^o$ is alkylaminoalkylidene show an antidepressant action, etc. [U.S. Pat. Nos. 3,354,155 and 3,420,851; Drugs, 13, 161 (1977), Arz.-Forsch., 13, 1039 (1963); ibid.,14, 100 (1964)]. Furthermore, it is known that derivatives such as cycloheptene (wherein $X_1$—$X_2$ is —CH=CH—) or thiepine wherein $W^o$ has an alkyl chain substituted with an alicyclic nitrogen-containing heterocyclic group such as piperazine, etc. at the terminal thereof via —NHCO— have a calcium antagonizing activity [Japanese Published Unexamined Patent Application Nos. 47466/1986 (USP 4,749,703) and 153280/1987].

Further oxepine derivatives having an antiallergic activity wherein $R^o$ has carboxylic acid group and $W^o$ has an alkylaminoalkyl chain via a hetero atom are known [Japanese Published Unexamined Patent Application Nos. 28972/1985 (U.S. Pat. No. 4,596,804); 152669/1986; 152670/1986; 152671/1986; 152672/1986 (all of them correspond to EP 188802 A); 152676/1986 and 257981/1986]. Furthermore, oxepine or cycloheptene (wherein $X_1$—$X_2$ =—CH₂CH₂—) derivatives showing an antihistaminic activity wherein $W^o$ is alkylaminoalkylidene are known [Japanese Published Unexamined Patent Application No. 45557/1987 (EP 214779A)].

In addition, thienobenzoxepine and thiepine derivatives showing an antiinflammatory activity wherein L is —S—, $R^o$ has carboxylic acid group and $W^o$ is oxo are disclosed in J. Med. Chem., 21, 633 (1978) supra.

SUMMARY OF THE INVENTION

Novel and useful $TXA_2$ antagonists are expected to have preventive and therapeutic effects on various diseases, and are in demand.

An object of the present invention is to provide novel tricyclic compounds having a $TXA_2$-antagonizing activity by containing side chains in combination, wherein aforementioned $R^o$ is the carboxylic acid group and $W^o$ is an aminoalkyl chain or aminoalkylidene substituted with an acyl group such as carbonyl, sulfonyl, etc. via a hetero atom.

The present invention relates to a tricyclic compound [hereafter referred to as Compound (I); terms like this shall apply to other compounds]represented by formula (I):

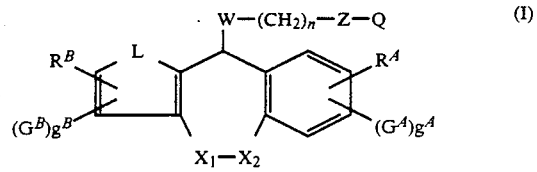

wherein ═, $X_1$—$X_2$ represents —$CH_2O$—,

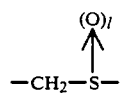

(wherein l represents 0, 1 or 2), —$CH_2$—$CH_2$— or —CH=CH—;

L represents —CH=CH— or —S—;

represents a single bond or a double bond;

W represents —S—, —O—, —NH—, —CH—, —NHCO— or =CH— (wherein the left side of each formula is bound to the mother nucleus); n is 0, 1, 2 or 3; Z represents —$NR^1CO$—, $NR^1SO_2$—, $NR^1CONH$—, $NR^1CONH$—, —$NR^1CSNH$—, —$NR^1NHCON$-H—,—$NR^1NHCSNH$—,—NR1COO— or —NR1COS—(wherein $R^1$ represents hydrogen or lower alkyl, in which the right side of each formula is bound to Q);

Q represents straight or branched alkyl having 1 to 18 carbon atoms, alicyclic alkyl having 3 to 6 carbon atoms, lower alkenyl having 2 to 6 carbon atoms, or optionally substituted aryl, optionally substituted aralkyl, optionally substituted aralkenyl, optionally substituted aromatic heterocyclic group [the group represents furyl, thienyl, N-substituted or unsubstituted pyrrolyl (the N-substituent is selected from lower alkyl, phenyl and benzyl), pyridyl, quinolyl or isoquinolyl]or coumarinyl; wherein the substitution means that with 1 to 3 substituents onto the aromatic ring and the substituent is independently selected from lower alkyl, phenyl, benzyl, halogen, trifluoromethyl, nitro, $OR^2$ and $SR^2$ (wherein $R^2$ represents hydrogen, lower alkyl, phenyl or benzyl); one of $R^A$ and $R^B$ represents hydrogen and the other represents —Y—M [wherein Y represents single bond, —$CR^3R^4$—$(CH_2)m$— or —$CR^3$=$CR^4$—(CH )m— (wherein each of $R^3$ and $R^4$ independently represents hydrogen or lower alkyl and m represents 0, 1, 2, 3 or 4, in which the left side of each formula is bound to the mother nucleus); M represents —$COOR^5$ (wherein $R^5$ represents hydrogen or lower alkyl), —$CONR^{5a}R^{5b}$ (wherein each of $R^{5a}$ and $R^{5b}$ independently has the same significance for $R^5$ as described above) or tetrazolyl]; each of $G^A$ and $G^B$ independently represents lower alkyl, halogen or $OR^6$ (wherein $R^6$ represents hydrogen, lower alkyl, phenyl or benzyl);

each of $g^A$ and $g^B$ independently represents 0, 1, 2 or 3; and a pharmaceutically acceptable salt thereof.

DETAILED DESCRIPTION OF THE INVENTION

In the definition of Q in formula (I), examples of the straight or branched alkyl having 1 to 18 carbon atoms include methyl, ethyl, propyl, isopropyl, butyl, isobutyl, sec-butyl, tert-butyl, pentyl, neopentyl, hexyl, heptyl, octyl, nonyl, decyl, undecyl, dodecyl, tridecyl, tetradecyl, pentadecyl, hexadecyl, heptadecyl and octadecyl, etc.; and examples of the alicyclic alkyl having 3 to 6 carbon atoms include cyclopropyl, cyclopentyl and cyclohexyl, etc. Examples of the lower alkenyl having 2 to 6 carbon atoms include vinyl, allyl, propenyl, butenyl and hexenyl, etc. The aryl is exemplified by phenyl and naphthyl having 6 to 10 carbon atoms, etc.; the aralkyl, by benzyl, phenethyl and benzhydryl having 7 to 15 carbon atoms, etc.; and the aralkenyl by styryl and cinnamyl having 8 to 18 carbon atoms, etc.

Further in the definition of each group in formula (I), examples of the lower alkyl include the straight or branched alkyl having 1 to 6 carbon atoms such as methyl, ethyl, propyl, isopropyl, butyl, isobutyl, sec-butyl, tert-butyl, pentyl, hexyl, etc. and of the alicyclic alkyl having 3 to 6 carbon atoms such as cyclopropyl, cyclopentyl and cyclohexyl, etc.; and examples of the halogen atom include fluorine, chlorine, bromine and iodine.

The pharmaceutically acceptable salt of Compound (I) includes an acid addition salt, a metal salt, an ammonium salt, an organic amine addition salt, an amino acid addition salt, etc. which are pharmaceutically acceptable.

As the pharmaceutically acceptable acid addition salt of Compound (I), mention may be made of the inorganic acid salt such as hydrochloride, sulfate, phosphate, etc. and the organic acid salt such as acetate, maleate, fumarate, tartarate, citrate, etc. As the pharmaceutically acceptable metal salt, the alkali metal salt such sodium salt, potassium salt, etc.; alkaline earth metal salt such as magnesium salt, calcium salt, etc. and further the aluminum salt and the zinc salt are appropriate. As the ammonium salt, mention may be made of a salt of ammonium, tetramethylammonium, etc. As the pharmaceutically acceptable organic amine addition salt, mention may be made of an addition salt of morpholine, piperidine, etc. As the pharmaceutically acceptable amino acid addition salt, an addition salt of lysine, glycine, phenylalanine or the like are mentioned.

Compounds represented by formula (II) can be used as the starting material in the process for producing Compound (I):

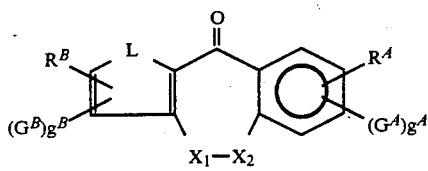

(wherein $X_1-X_2$, L, $R^A$, $R^B$, $G^A$ $G^B$, $g^A$ and $g^B$ have the same significances as described above).

Compounds (II) are either described in J. Med. Chem., 19, 941 (1976); ibid., 21, 1035 (1978); ibid., 20, 1557 (1977); ibid., 20, 1499 (1977); ibid., 29, 2347 (1986); ibid., 21, 633 (1978); ibid., 20, 456 (1977); U.S. Pat. Nos. 4,172,949 and 4,282,365; Japanese Published Unexamined Patent Application Nos. 21679/1983; 28972/1985; 152669/1986; 152672/1986; 152675/1986 and 10784/1988, etc. or can be synthesized according to methods described in these publications.

Hereafter processes for producing Compound (I) are described below but the production of Compound (I) is not deemed to be restricted thereto. Further in various processes, reaction conditions can be appropriately chosen from those described below.

A reaction solvent may be chosen from water or an organic solvent which does not participate in the reaction and can be used alone or in combination. Examples of the organic solvent include an alcohol such as methanol, ethanol, propanol, isopropanol, etc.; an ether such as diethyl ether, dioxane, tetrahydrofuran, ethylene glycol monomethyl ether or ethylene glycol dimethyl ether, etc.; a hydrocarbon such as benzene, toluene, xylene, hexane, cyclohexane, petroleum ether, ligroin, decaline, etc.; a ketone such as acetone, methyl ethyl ketone, etc.; an amide such as formamide, dimethylformamide, hexamethylphosphoric triamide, etc.; acetonitrile, ethyl acetate, dimethylsulfoxide or a halogenated hydrocarbon such as methylene chloride, dichloroethane, tetrachloroethane, chloroform, carbon tetrachloride, etc. Further in case that bases or acids later described are liquid, they may also be used as a solvent.

As the appropriate base, an inorganic or organic base can be used. These bases include an alkali metal hydroxide, for example, lithium hydroxide, sodium hydroxide or potassium hydroxide; an alkali metal carbonate, for example, sodium carbonate, sodium hydrogencarbonate or potassium carbonate; an alkali metal acetate, for example, sodium acetate or potassium acetate; an alkali metal alkoxide, for example, sodium methoxide, sodium ethoxide or potassium tert-butoxide; or an organic metal compound, for example, sodium hydride, n-butyl lithium, sec-butyl lithium; and an organic amine, for example, triethylamine, tri-n-butylamine, pyridine, N,N-dimethylamino-pyridine, picoline, lutidine, N,N-dimethylaniline, dicyclohexylmethylamine, N-methylpiperidine, morpholine, diazabicyclooctane, diazabicycloundecene or N-benzyltrimethylammonium hydroxide (Triton B), etc.

As the appropriate acid, an inorganic or organic acid or Lewis acid can be used. Examples of the inorganic acid include hydrochloric acid, hydrobromic acid, hydroiodic acid, sulfuric acid, nitric acid, hypochloric acid, sulfurous acid or nitrous acid, etc. Examples of the organic acid are formic acid, acetic acid, trifluoroacetic acid, benzoic acid, p-toluenesulfonic acid, camphorsulfonic acid or methanesulfonic acid, etc. Examples of the Lewis acid include aluminum chloride, zinc chloride, tin chloride, boron trifluoride, boron trifluoride diethyl ether complex, titanium tetrachloride, etc.

A reaction temperature is generally from $-80°$ C. to a boiling point of a solvent It is also possible to heat in the absence of any solvent The reaction may generally be carried out under normal pressure but it is also possible to apply pressure In this case, the reaction temperature may be raised to a temperature higher than the boiling point of a solvent.

A reaction time is generally in a range of 1 minute to a week.

In the following description, preferred reaction conditions are given.

Further in the following description, the tricyclic moiety that does not directly participate in the reaction:

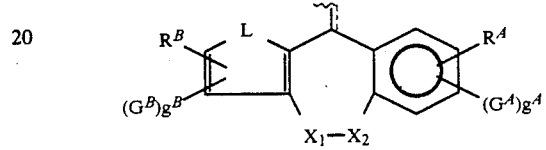

wherein , $X_1-X_2$, L, $R^A$, $R^B$, $G^A$, $G^B$, $g^A$ and $g^B$ have the same significances as described above; is sometimes referred to as:

Method 1-1

Synthesis of Compound (Ia) in Compound (I), wherein W is $W_a$ and Z is $-NR^1SO_2-$ (part 1)

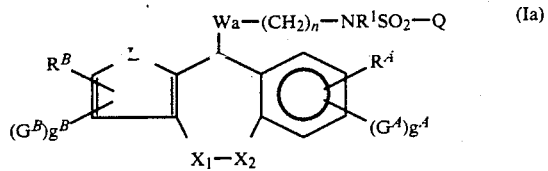

wherein $W_a$ represents $-S-$, $-O-$ or $-NH-$; and $X_1-X_2$, L, $R^A$, $R^B$, $G^A$, $G^B$, $R^1$, Q, n, $g^A$ and $g^B$ have the same significances as described above.

Firstly, the carbonyl group of Compound (II) is converted into Compound (IIIa), (IIIb) or (IIIc) according to the following reaction equations:

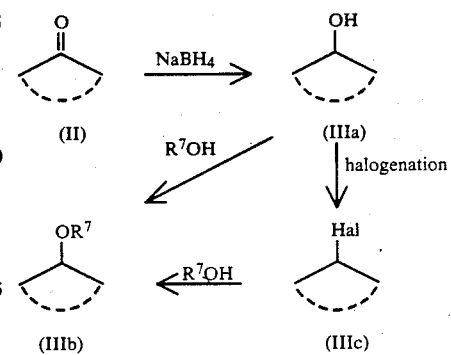

wherein

has the same significance as described above;

$R^7$ represents lower alkyl and Hal represents halogen. Herein the definitions of the lower alkyl and halogen are the same as in the definitions of the lower alkyl and halogen for the respective groups in formula (I).

Compound (II) and 0.5 to 5 molar equivalents of sodium borohydride are reacted in an alcohol, for example, methanol, at a temperature from 0° C. to room temperature for 1 to 24 hours to obtain Compound (IIIa).

Compound (IIIb) can be obtained by reacting Compound (IIIa) with an alcohol shown by $R^7$—OH in the presence of an appropriate acid catalyst, for example, p-toluenesulfonic acid, etc. at between room temperature and a boiling point of the alcohol for 1 to 24 hours.

Compound (IIIc) can be obtained by reacting Compound (IIIa) with 1 to 5 molar equivalents of a halogenating agent such as thionyl chloride, phosphorus oxychloride, phosphorus tribromide, etc. as they are, or, in an inert solvent such as methylene chloride, chloroform, etc., at a temperature from 0° C. to room for 1 to 24 hours.

Further, the thus obtained Compound (IIIc) is led to Compound (IIIb) by reacting Compound (IIIc) with an alcohol shown by $R^7$—OH, if necessary and desired, in the presence of a base such as pyridine, etc., at between room temperature and a boiling point of the alcohol for 1 to 24 hours.

The thus obtained Compounds (IIIa), (IIIb) and (IIIc) are converted into Compound (Va) according to the following reaction step.

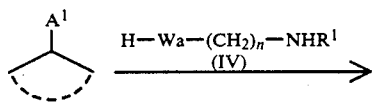

(IIIa)  ($A^1$ = OH)
(IIIb)  ($A^1$ = $OR^7$)
(IIIc)  ($A^1$ = Hal)

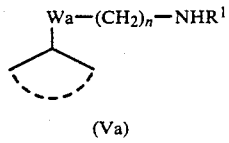

(Va)

wherein $A^1$ represents OH, $OR^7$ or Hal, and

$W_a$, $R^1$, $R^7$, Hal and n have the same significances as described above.

Compound (Va) or acid addition salts thereof can be obtained by reacting Compound (IIIa) with 1 to 5 molar equivalents of an appropriate dehydrating and condensing agent, for example, trifluoroacetic anhydride, in an inert solvent such as methylene chloride, chloroform, etc., at a temperature of from 0° C. to room temperature for 1 to 24 hours, then adding 1 to 5 molar equivalents of Compound (IV) or acid addition salts thereof (for example, hydrochloride, hydrobromide, acetate, trifluoroacetate and p-toluenesulfonate; in the following description, the acid addition salts also mean these salts) to this reaction solution and carrying out the reaction at between 0° C. and a boiling point of the solvent, if necessary and desired, in the presence of an appropriate acid catalyst, for example, boron trifluoride diethyl ether complex, for 1 to 24 hours, according to the method disclosed in Japanese Published Unexamined Patent Application No. 152676/1986.

Compound (Va) or acid addition salts thereof can also be obtained by reacting Compound (IIIb) with 1 to 5 molar equivalents of Compound (IV) or acid addition salts thereof in an inert solvent such as methylene chloride, chloroform, etc., at between 0° C. and a boiling point of the solvent, if necessary and desired, in the presence of an appropriate acid catalyst, for example, boron trifluoride diethyl ether complex, for 1 to 24 hours.

Compound (Va) or acid addition salts thereof can also be obtained by reacting Compound (IIIc) with 1 to 10 molar equivalents of Compound (IV) or acid addition salts thereof in an inert solvent such as methylene chloride, chloroform, etc., between at 0° C. and a boiling point of the solvent, if necessary and desired, in the presence of a base such as triethylamine, etc. for 1 to 24 hours.

Then, Compound (Va) is converted into Compound (Ia) according to the following reaction step.

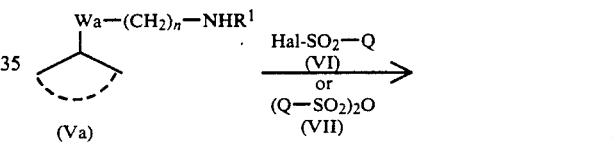

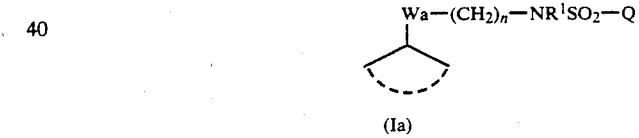

(Ia)

wherein

$W_a$, n, $R^1$, Hal and Q have the same significances as described above.

Compound (Ia) can be obtained by reacting Compound (Va) or acid addition salts thereof with 1 to 5 molar equivalents of a sulfonyl halide (VI) or a sulfonic anhydride (VII) in an inert solvent such as methylene chloride, chloroform, etc., in the presence of a base such as pyridine, etc. or in a basic organic solvent such as pyridine, triethylamine, etc., at a temperature of from 0° C. to room temperature for 1 to 24 hours.

Method 1-2

Synthesis of Compound (Ia) (part 2)

Compound (IXb) or (IXc) can be obtained from (IIIa), (IIIb) and (IIIc) shown in Method 1-1 according to the following reaction steps.

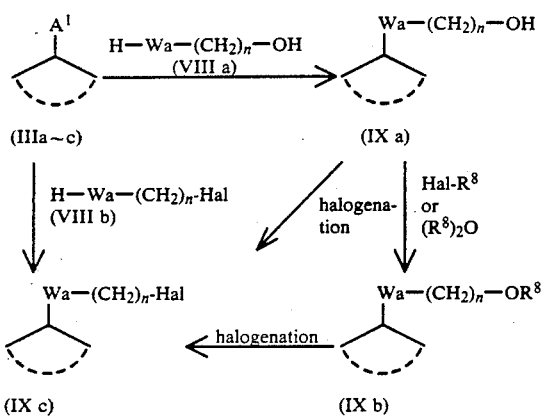

wherein

$A^1$, $W_a$, Hal and n have the same significances as described above; and $R^8$ represents a group capable of being split as $OR^8$.

Herein, $R^8$ means alkylsulfonyl such as methanesulfonyl, trifluoromethanesulfonyl, etc. and arylsulfonyl such as phenylsulfonyl, p-toluenesulfonyl, etc.

The corresponding Compound (IXa) or (IXc) can be obtained by reacting Compound (IIIa) with 1 to 5 molar equivalents of an appropriate dehydrating and condensing agent, for example, trifluoroacetic anhydride, in an inert solvent such as methylene chloride, chloroform, etc., at a temperature of from 0° C. to room temperature for 1 to 24 hours, then adding 1 to 10 molar equivalents of an alcohol (VIIIa) or its halide (VIIIb) to this reaction solution and carrying out the reaction at between room temperature and a boiling point of the solvent, if necessary and desired, in the presence of an appropriate acid catalyst, for example, boron trifluoride diethyl ether complex, for 1 to 24 hours.

Compound (IXa) or (IXc) can also be obtained by reacting Compound (IIIb) or (IIIc) with 1 to 10 molar equivalents of an alcohol (VIIIa) or its halide (VIIIb) in an inert solvent such as methylene chloride, chloroform, etc., at between room temperature and a boiling point of the solvent, if necessary and desired, in the presence of an appropriate acid catalyst, for example, boron trifluoride diethyl ether complex, for 1 to 24 hours.

Further the thus obtained Compound (IXa) may be reacted with 1 to 5 molar equivalents of Hal—$R^8$ or $(R^8)_2$O (wherein $R^8$ has the same significance as described above) in an inert solvent such as methylene chloride, chloroform, etc. if necessary and desired, in the presence of a base such as pyridine, etc. at a temperature of from −50° C. to room temperature for 1 to 24 hours to give Compound (IXb).

Furthermore, Compound (IXa) may be reacted either with 1 to 5 molar equivalents of a halogenating agent, for example, thionyl chloride, in an inert solvent such as methylene chloride, chloroform, etc., if necessary and desired, in the presence of a base such as pyridine, etc., at a temperature of from 0° C. to room temperature for 1 to 24 hours to give Compound (IXc), or with 1 to 10 molar equivalents of a halogenating agent such as methanesulfonyl chloride, etc. in dimethylformamide in the presence of 1 to 10 molar equivalents of a salt such as lithium chloride at a temperature of from −20° C. to 100° C. for 1 to 24 hours.

Where Compound (IXc) is the chloride (Hal=Cl) or bromide (Hal=Br), the compound may be reacted further with an iodide, for example, sodium iodide, in a polar solvent such as acetonitrile to give the iodide (Hal=I). Compound (IXb) can be converted into Compound (IXc) under similar conditions.

The thus obtained Compound (IXb) or Compound (IXc) can be converted into Compound (Va), wherein routes for the conversion are different depending upon the species of $R^1$. That is, in case that $R^1$ is H, Route A [Gariel synthesis: Merk Index, 10th edition, page ONR-34 (1983)] is advantageously applied; in case that $R^1$ is not H, Route B is applied.

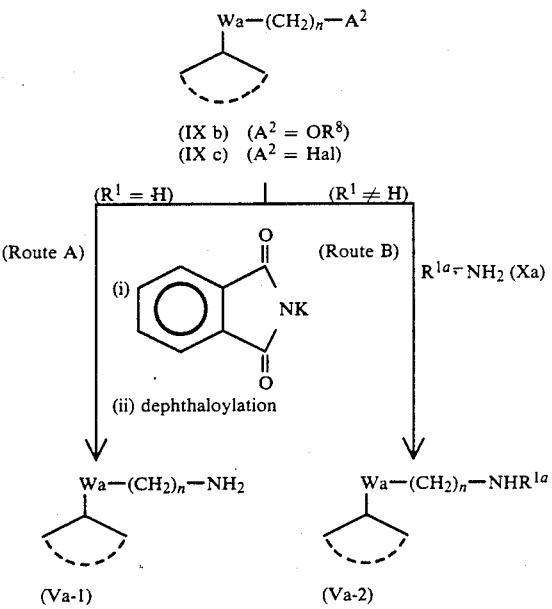

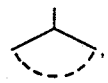

Wa and n have also the same significances as described above.

Route A

Compound (IXb) or Compound (IXc) is reacted with 1 to 10 molar equivalents of potassium phthalimide in a polar solvent, for example, N,N-dimethylformamide, between at room temperature and a boiling point of the solvent for 1 to 48 hours, followed by dephthaloylation. The reaction may be completed by reacting with hydrazine in an alcoholic solvent such as methanol, at between room temperature and a boiling point of the solvent for 1 to 48 hours to give dephthaloyled Compound (Va-1).

Route B

Compound (Va-2) can be obtained by reacting Compound (IXb) or Compound (IXc) with 1 molar equivalent to a largely excessive amount of an amine (Xa) or acid addition salts thereof in an inert solvent such as ethanol, dioxane, etc., at a temperature of from 0° C. to a boiling point of the solvent, for 1 to 48 hours.

Compound (Va) [(Va-1) and/or (Va-2)] or acid addition salts thereof can be converted into Compound (Ia) in a manner similar to Method 1-1.

Method 2

Synthesis of Compound (Ib) in Compound (I), wherein W is —NHCO— and Z is —NR$^1$SO$_2$

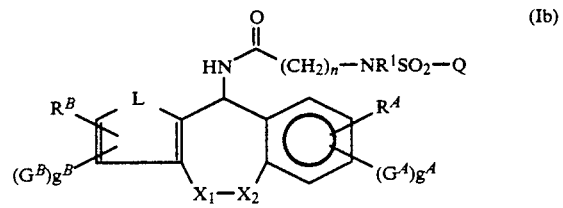

wherein $X_1$—$X_2$, L, $R^A$, $R^B$, $G^A$, $G^B$, $R^1$, Q, n, $g^A$ and $g^B$ have the same significances as described above.

Compound (IIIc) described in Method 1-1 is converted into Compound (Vb) according to the following reaction steps:

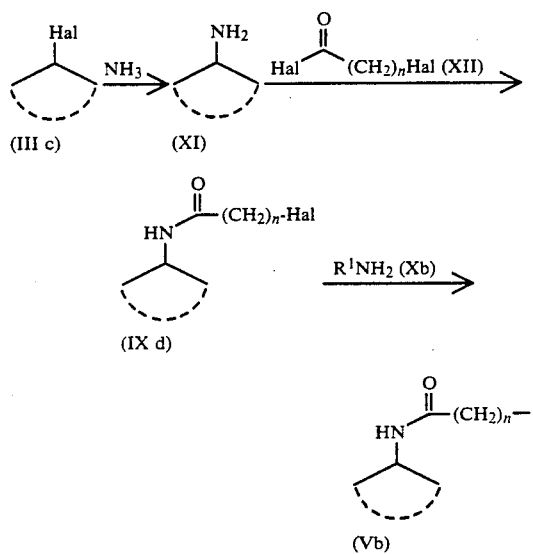

wherein

$R^1$, n and Hal have the same significances as described above.

Compound (XI) can be obtained by reacting Compound (IIIc) with a molar equivalent to a largely excessive amount of ammonia in an inert solvent such as methylene chloride, chloroform, etc., at a temperature from −78° C. to room temperature, for 1 to 24 hours.

Next, Compound (XI) or acid addition salts thereof are reacted with 1 to 5 molar equivalents of an acid halide (XII) in an inert solvent such as methylene chloride, chloroform, etc., if necessary and desired, in the presence of a base such as pyridine, etc., at a temperature of from 0° C. to room temperature for 1 to 24 hours to give Compound (IXd).

The thus obtained Compound (IXd) is reacted with a molar equivalent to a largely excessive amount of an amine (Xb) or acid addition salts thereof in an inert solvent such as methylene chloride, chloroform, etc , if necessary and desired, in the presence of a base such as triethylamine, etc., between at 0° C. and a boiling point of the solvent for 1 to 24 hours to give Compound (Vb).

Compound (Ib) can be obtained from Compound (Vb) or acid addition salts thereof according to the following reaction steps.

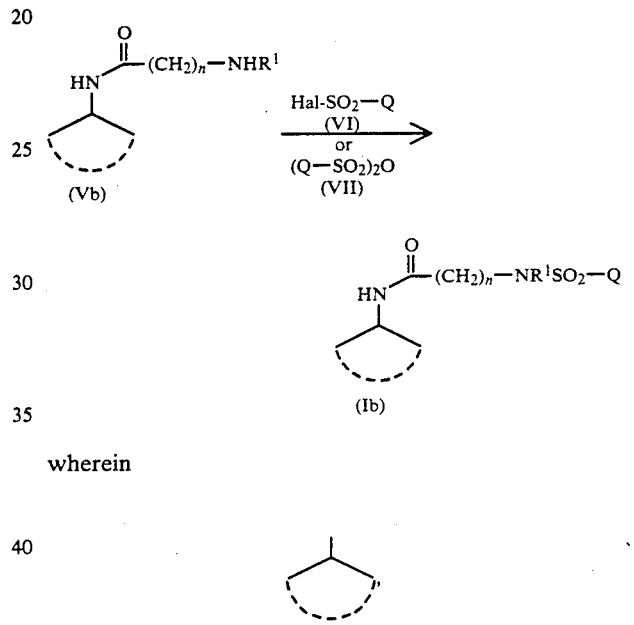

wherein

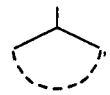

$R^1$, n, Hal and Q have the same significances as described above.

The reaction can be performed in a manner similar to the method for converting Compound (Va) into Compound (Ia) in Method 1-1.

Method 3-1

Synthesis of Compound (Ic) in Compound (I), wherein W is =CH— and Z is —NR$^1$SO$_2$—

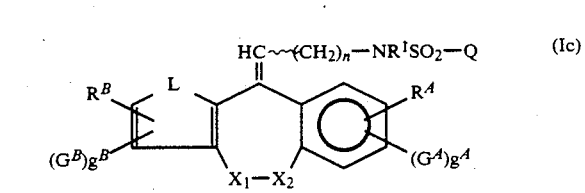

wherein $X_1$—$X_2$, L, $R^A$, $R^B$, $G^A$, $G^B$, $R^1$, Q, n, $g^A$ and $g^B$ have the same significances as described above.

Firstly, the carbonyl group of Compound (II) is converted into Compound (IXf) according to the following reaction steps:

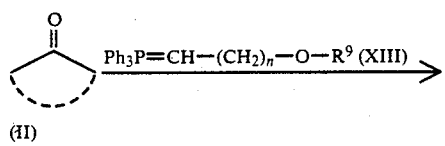

(II)

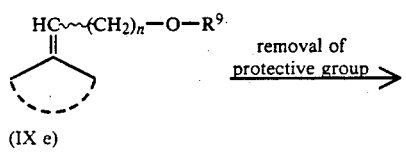

(IX e)

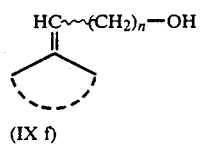

(IX f)

wherein

and n have the same significances as described above, $R^9$ represents a protective group of hydroxyl and Ph represents phenyl.

Herein, as the protective group for hydroxyl, groups generally used as protective groups for an alcoholic hydroxyl may be used; preferably used is, for example, tetrahydropyranyl or the like.

An ylide (XIII) in which hydroxyl is protected by an appropriate protective group (for example, tetrahydropyranyl, etc.) is formed in an inert solvent, for example, tetrahydrofuran [J. Org. Chem., 44, 3760 (1979)].

Then, the formed ylide (XIII) is reacted with 0.2 to 1 molar equivalent of Compound (II) based on Compound (XIII) at a temperature from $-78°$ C. to a boiling point of the solvent for 1 to 48 hours to give Compound (IXe).

The protective group is removed from Compound (IXe) to give Compound (IXf) The removal of protective group can be conducted in a conventional manner; in the case of using, for example, tetrahydropyranyl group as a protective group, Compound (IXe) is reacted in a suitable hydrated solvent such as hydrated dioxane, hydrated tetrahydrofuran, etc., in the presence of an acid catalyst such as p-toluenesulfonic acid, hydrochloric acid, etc., at between 0° C. and a boiling point of the solvent for 1 to 24 hours to give Compound (IXf).

Compound (IXf) can be led to Compound (IXg) or Compound (IXh) by the following reaction steps.

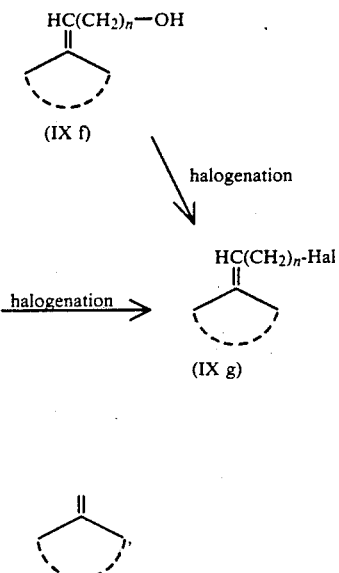

wherein $R^8$, Hal and n have the same significances as described above.

The reactions can be performed in a manner similar to the method for leading from Compound (IXa) to Compound (IXb) and Compound (IXc) and from Compound (IXb) to Compound (IXc), described in Method 1-2.

Compound (Vc) [Vc-1) and/or (Vc-2)] can be obtained from Compound (IXg) and Compound (IXh) according to the following reaction equation.

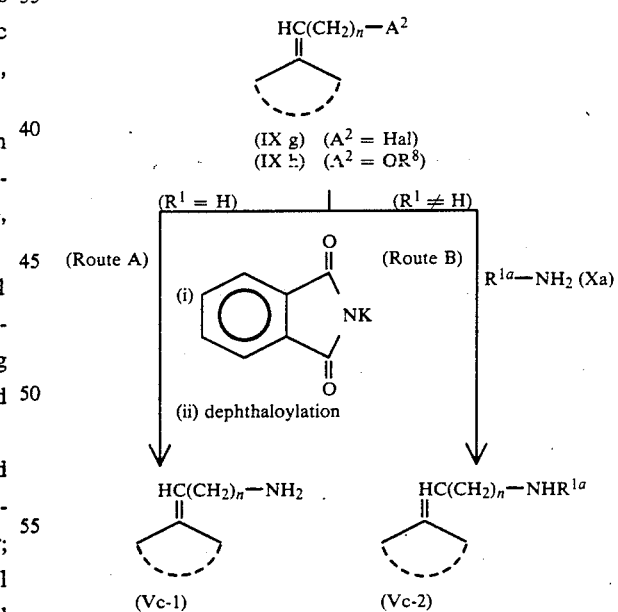

wherein

$A^2$, Hal, $R^8$, $R^1$, $R^{1a}$ and n have the same significances as described above.

The reactions can be performed in a manner similar to the method for converting Compound (IXb) and Compound (IXc) into Compound (Va) in Method 1-2.

Compound (Vc) or acid addition salts thereof can be converted into Compound (Ic) in a manner similar to the method for converting Compound (Va) into Compound (Ic) in Method 1-1.

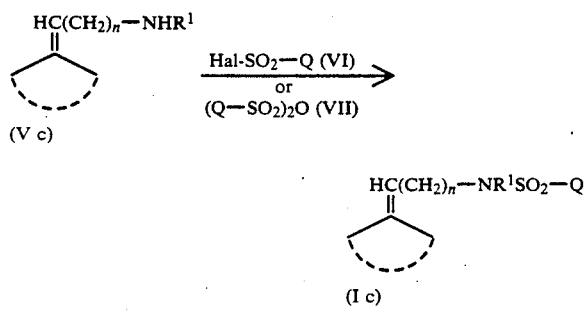

wherein $R^1$, Q, Hal and n have the same significances as described above.

Method 3-2

Synthesis of Compound (Ic-1) in Compound (Ic), wherein n is 1

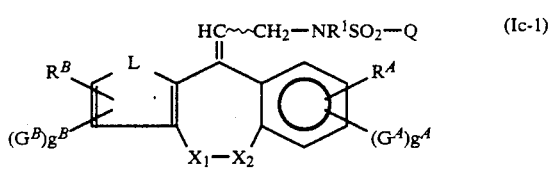

wherein $X_1-X_2$, L, $R^A$, $R^B$, $G^A$, $G^B$, $R^1$, Q, n, $g^A$ and $g^B$ have the same significances as described above.

Firstly, the carbonyl group of Compound (II) is converted into Compound (XV) according to the following reaction steps:

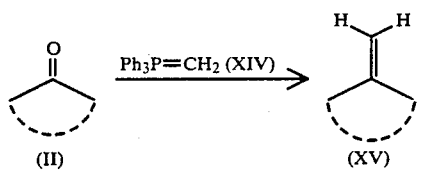

wherein and Ph have the same significances as described above.

Compound (II) is reacted with 1 to 5 molar equivalents of an ylide (XIV) in an inert solvent such as tetrahydrofuran, etc., at a temperature of from 0° C. to room temperature for 1-48 hours to give Compound (XV).

Compound (XV) can be converted into Compound (IXg-1) [in Compound (IXg), n is 1 and Hal is chlorine] according to the following reaction steps.

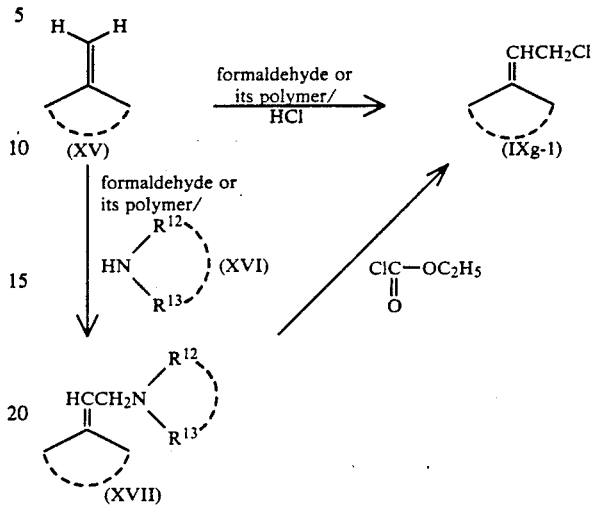

wherein has the same significance as described above; each of $R^{12}$ and $R^{13}$ independently represents lower alkyl or may be combined to nitrogen adjacent thereto to form a heterocyclic ring.

Herein, lower alkyl has the same significance as previously described for lower alkyl in formula (I). As the heterocyclic ring formed, mention may be made of pyrrolidine, piperdine, N-methylpiperazine, morpholine, N-methylhomopiperazine and the like.

Compound (XV) is reacted with 1 to 10 molar equivalents of formaldehyde and/or a formaldehyde polymer, for example, paraformaldehyde, in hydrochloric acid or an inert solvent, for example, dioxane, saturated with hydrogen chloride and, if necessary and desired, in the presence of a strong acid such as sulfuric acid or trifluoroacetic acid, between at room temperature and a boiling point of the solvent, for 1 to 24 hours to give Compound (IXg-1).

Further Compound (IXg-1) can also be obtained as follows. That is, Compound (XV) is reacted with 1 to 2 molar equivalents of formaldehyde and/or a formaldehyde polymer, for example, paraformaldehyde, and 1 to 3 molar equivalents of a secondary amine (XVI) and trifluoroacetic acid, in an inert solvent such as methylene chloride, dichloroethane, chloroform, etc , if necessary and desired, in the presence of acetic acid, between at room temperature and a boiling point of the solvent, for 1 to 48 hours to give Compound (XVII) This compound is reacted with 1 to 10 molar equivalents of ethyl chloroformate in an inert solvent such as methylene chloride, chloroform, etc., between at 0° C. and a boiling point of the solvent for 1 to 48 hours to give Compound (IXg-1).

The thus obtained Compound (IXg-1) can be converted into Compound (Ic-1) via Compound (Vc-3) according to the following reaction steps, in a manner similar to the method for converting Compound (IXg) into Compound (Ic) in Method 3-1.

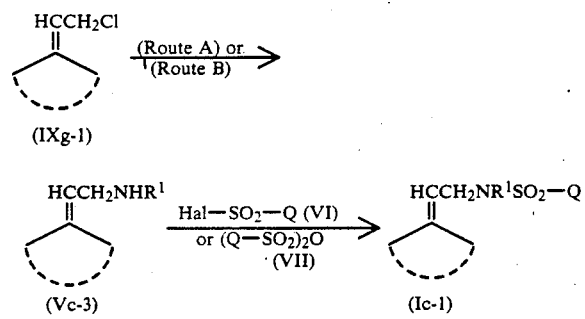

wherein

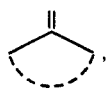

$R^1$, Q and Hal have the same significances as described above.

Herein, Route A and Route B can be carrier out according to Method 3-1.

Method 4

Synthesis of Compound (Id) in Compound (I), wherein W is Wb and Z —NR$^1$CO—

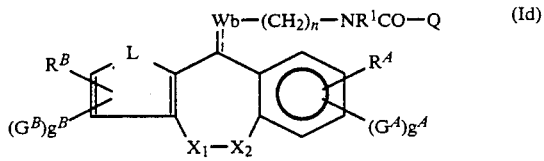

wherein Wb represents —S—, —O—, —NH—, —NHCO— or =CH—; and , X —X$_2$, L, R$^A$, R$^B$, G$^A$, G$^B$, R$^1$, Q, n, g$^A$ and g$^B$ have the same significances as described above.

Compound (Id) can be obtained from Compound (Va), (Vb) or (Vc) according to the following reaction steps.

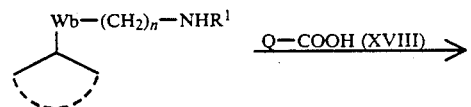

(Va) (Wb = Wa)
(Vb) (Wb = —NHCO—)
(Vc) (Wb = =CH—)

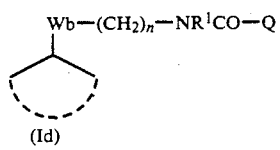

wherein

Wa, Wb, R$^1$, Q and n have the same significances as described above.

Compound (Id) can be obtained by reacting Compound (Va), (Vb) or (Vc) or acid addition salts thereof with 1 to 5 molar equivalents of a carboxylic acid (XVIII) or reactive derivatives thereof, either in an inert solvent such as methylene chloride, chloroform, etc., if necessary and desired, in the presence of a base such as pyridine, etc. or in a basic solvent such as pyridine, between at 0° C. and a boiling point of the solvent for 1 to 48 hours.

Herein, the carboxylic acid reactive derivative include an acid halide such as acid chloride, acid bromide, etc., an acid anhydride such as acid anhydride formed with a dehydrating condensing agent such as N,N'-dicyclohexylcarbodiimide, etc., in the reaction system, commercially available acid anhydrides, etc.), an activated ester such as p-nitrophenyl ester, N-hydroxysuccinimide ester), a mixed acid anhydride such as monoethyl carbonate, monoisobutyl carbonate, etc. and the like.

Method 5

Synthesis of Compound (Ie) in Compound (I), wherein W is Wb and Z is

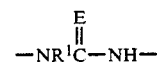

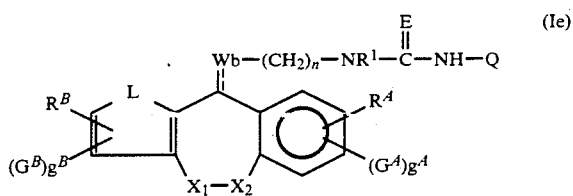

wherein ⁀, X$_1$—X$_2$, L, R$^A$, R$^B$, G$^A$, G$^B$, Wb, R$^1$, Q, n, g$^A$ and g$^B$ have the same significances as described above and E represents oxygen or sulfur.

Compound (Ie) can be obtained from Compound (Va), (Vb) or (Vc) according to the following reaction steps.

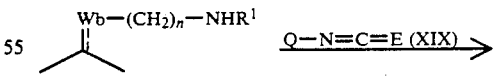

(Va) (Wb = Wa)
(Vb) (Wb = —NHCO—)
(Vb) (Wb = =CH—)

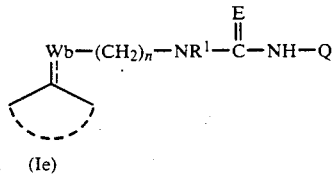

wherein

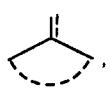

Wa, Wb, R¹, Q, E and n have the same significances as described above.

Compound (Ie) can be obtained by reacting Compound (Va), (Vb) or (Vc) or acid addition salts thereof with 1 to 5 molar equivalents of an isocyanate (XIX wherein E=O) or an isothiocyanate (XIX wherein E=S), in an inert solvent, for example, toluene, if necessary and desired, in the presence of a base such as pyridine, etc. between at 0° C. and a boiling point of the solvent for 1 to 24 hours.

Method 6

Synthesis of Compound (If) in Compound (I), wherein W is Wb and Z is $$-NR^1NHCNH-\atop\overset{E}{\|}$$

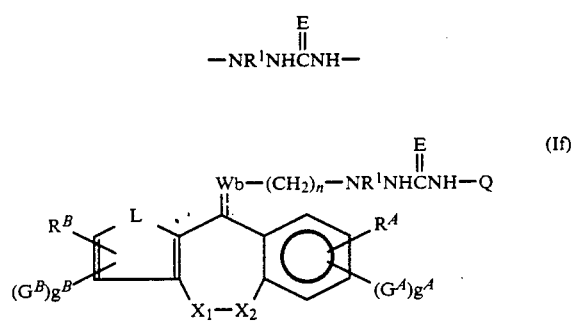

wherein ⋯, $X_1$—$X_2$, L, $R^A$, $R^B$, $G^A$, $G^B$, Wb, $R^1$, E, Q, n $g^A$ and $g^B$ have the same significances as described above.

Compound (If) can be obtained according to the following reaction steps.

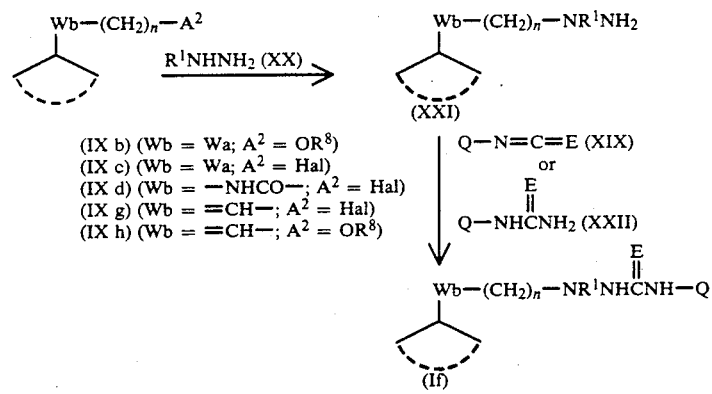

wherein

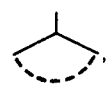

Wa, Wb, A₂, R¹, R⁸, Hal, Q, E and n have the same significances as described above.

Compound (XXI) can be obtained by reacting Compound (IXb), (IXc), (IXd), (IXg) or (IXh) with a molar equivalent to a largely excessive amount of a hydrazine (XX) or acid addition salts thereof, in an inert solvent such as ethanol, etc., if necessary and desired, in the presence of a base such as triethylamine, etc. between at 0° C. and a boiling point of the solvent for 1 to 24 hours.

Next, Compound (XXI) or acid addition salts thereof are reacted with 1 to 5 molar equivalents of an isocyanate (XIX wherein E=O) or an isothiocyanate (XIX wherein E=S), in an inert solvent, for example, tetrahydrofuran, etc., if necessary and desired, in the presence of a base such as pyridine, etc. between at 0° C. and a boiling point of the solvent for 1 to 24 hours to give Compound (If).

Alternatively, Compound (XXI) or acid addition salts thereof are reacted with 1 to 5 molar equivalents of an urea (XXII: E is 0) or a thiourea (XXII: E is S), in an inert solvent, for example, water, etc., if necessary and desired, in the presence of a base such as sodium bicarbonate, etc. between at 0° C. and a boiling point of the solvent for 1 to 24 hours to give Compound (If).

Method 7

Synthesis of Compound (Ig) in Compound (I), wherein W is Wb and Z is $$-NR^1C-E-]\atop\overset{O}{\|}$$

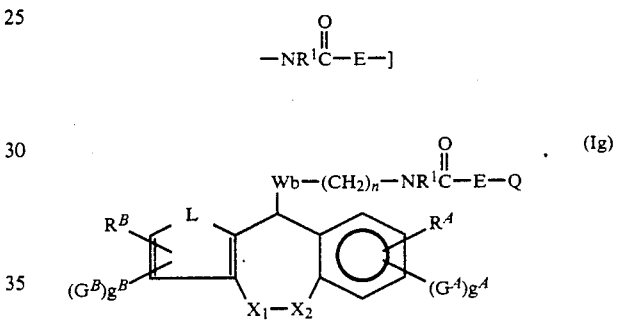

wherein ⋯, $X_1$—$X_2$, L, $R^A$, $R^B$, $G^A$, $G^B$, Wb, $R^1$, E, Q, n, $g^A$ and $g^B$ have the same significances as described above.

Compound (Ig) can be obtained according to the following reaction steps.

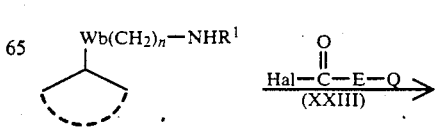

-continued

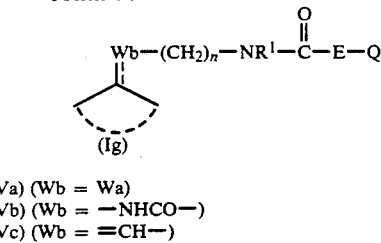

(Va) (Wb = Wa)
(Vb) (Wb = —NHCO—)
(Vc) (Wb = =CH—)

wherein

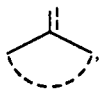

Wa, Wb, $R^1$, E, Q, Hal and n have the same significances as described above. Compound (Ig) can be obtained by reacting Compound (Va), (Vb) or (Vc) or acid addition salts thereof with 1 to 5 molar equivalents of a haloformate (XXIII), in an inert solvent, for example, pyridine, between at 0° C. and a boiling point of the solvent for 1 to 24 hours.

Method 8

Synthesis of Compound (Ih) in Compound (I), wherein W is —CH$_2$—

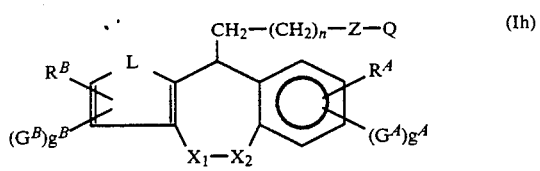

wherein $X_1$—$X_2$, L, $R^A$, $R^B$, $G^A$, $G^B$, Z, Q, n, $g^A$ and $g^B$ have the same significances as described above.

Compound (Ih) can be obtained according to the following reaction steps.

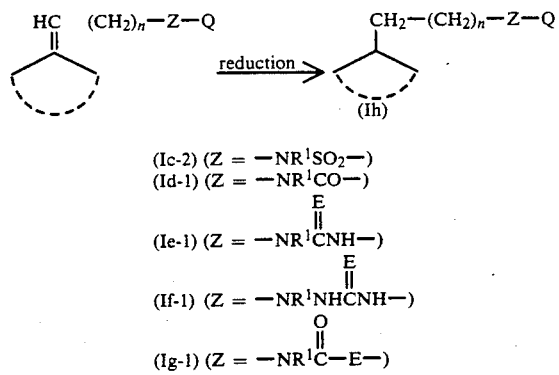

(Ic-2) (Z = —NR$^1$SO$_2$—)
(Id-1) (Z = —NR$^1$CO—)
(Ie-1) (Z = —NR$^1$C$\overset{\text{E}}{\underset{\|}{}}$NH—)
(If-1) (Z = —NR$^1$NHC$\overset{\text{E}}{\underset{\|}{}}$NH—)
(Ig-1) (Z = —NR$^1$C$\overset{\text{O}}{\underset{\|}{}}$—E—)

wherein

Z, Q, $R^1$, E and n have the same significances as described above.

Compound (Ih) wherein W is —CH$_2$— can be obtained by subjecting Compound (Ic-2), (Id-1), (Ie-1), (If-1) or (Ig-1) wherein W is =CH— to a suitable reduction process, for example, hydrogenation using as a catalyst, for example, palladium-carbon, platinum oxide, Raney nickel, nickel boride or cobalt boride, etc., if necessary and desired, in the co-presence of an acid such as hydrochloric acid, in an inert solvent, for example, ethanol, acetic acid, etc. between at 0° C. and a boiling point of the solvent for 1 to 48 hours, under from normal pressure to under pressure.

Method 9-1

In the methods for production shown by Methods 1 through 8, where groups defined in Compound (I) change under reaction conditions for practicing the method or are inappropriate for practicing the method, the groups may be subjected to conventional means used in organic synthesis chemistry, for example, means for protecting functional groups, removing protection, etc. [for example, cf., Protective Groups in Organic Synthesis, Green, John Wiley & Sons Incorporated (1981)], methods for oxidation, reduction, hydrolysis, etc. [for example, cf., SHIN-JIKKEN KAGAKU KOZA, vols. 14 & 15, Maruzen (1977)]. For example, in case that M is —COOH, a desired compound can be obtained either by hydrolyzing the corresponding ester (cf., Method 9-2 later described) or by hydrolyzing (removing protection of) a compound obtained according to Methods 1 through 8, etc. in which the group corresponding to —Y—M is —Y'—CH$_2$OD [wherein Y' represents a group obtained by removing CH from Y and D represents a protective group of hydroxyl (e.g., acetyl, etc.)] and oxidizing the resulting —Y'—CH$_2$OH.

Method 9-2

Synthesis of Compound (I-1) in Compound (I), wherein M is —COOH

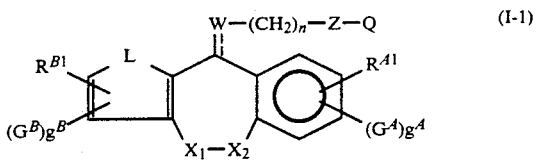

wherein one of $R^{A1}$ and $R^{B1}$ represents —Y—COOH and the other represents hydrogen; and ---, $X_1$—$X_2$, L, $G^A$, $G^B$, Y, W, Z, Q, n, $g^A$ and $g^B$ have the same significances as described above.

Compound (I-1) can be obtained according to the following reaction steps.

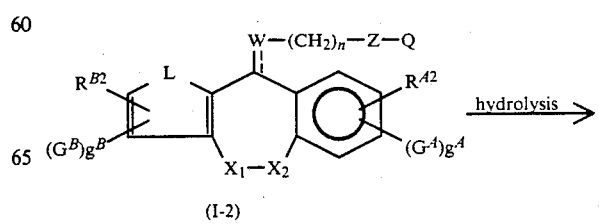

-continued

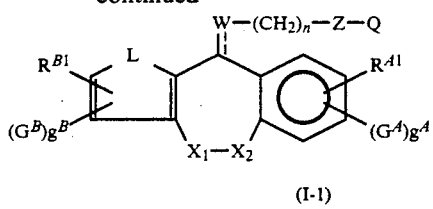

(I-1)

wherein one of $R^{A2}$ and $R^{B2}$ represents $-Y-COOR^{14}$ and the other represents hydrogen; and ---, $X_1-X_2$, L, $G^A$, $G^B$, Y, W, Z, Q, $R^{A1}$, $R^{B1}$n, $g^A$ and $g^B$ have the same significances as described above and $R^{14}$ represents lower alkyl.

Herein, the lower alkyl is the same as defined for the lower alkyl of each group in formula (I).

Compound (I-2) synthesized by applying Methods 1 to 8 is subjected to an appropriate hydrolysis, for example, reacted with a molar equivalent to a largely excessive amount of sodium hydroxide or potassium hydroxide, etc. in a solvent mixture of a lower alcohol such as methanol, ethanol, etc. and water, between at room temperature and a boiling point of the solvent, for 1 to 48 hours to give Compound (I-1).

The intermediates and desired compounds in the respective methods described above can be isolated and purified by purification methods conventionally used in organic synthesis chemistry, for example, filtration, extraction, washing, drying, concentration, recrystallization, various column chromatographies, etc. Further the intermediates may also be provided in the subsequent reaction, without being particularly purified.

In Compound (I) obtained by the foregoing methods, compounds wherein W is =CH— include geometrical isomers of E-form and Z-form with respect to stereochemistry. In general, the methods described above give a mixture of these isomers. Isolation and purification of these isomers can be made in a conventional manner used in organic synthesis chemistry, for example, column chromatography, recrystallization, etc.

It is also possible to isolate the isomers at stages of intermediates (IXe to IXh), (Vc) and (XVII), by the aforesaid various methods.

Further, if desired, E- and Z-forms may be isomerized from each other. This isomerization can be made by treating each isomer under reflux in e.g., acetic acid, for 1 to 24 hours, in the presence of an appropriate acid catalyst such as p-toluenesulfonic acid, etc.

In the present invention, Compound (I) includes not only the E/Z isomers described above but also all possible stereoisomers and a mixture thereof.

In case that salts of Compound (I) are desired to obtain, when Compound (I) is obtained in the form of a salt, Compound (I) may be purified as it is. Further in case that Compound (I) is obtained in a free form, salts may be formed in a conventional manner. Furthermore, Compound (I) and pharmaceutically acceptable salts thereof may also be present in the form of addition products to water or various solvents; in these adducts including the pharmaceutically acceptable salts are also included in the present invention.

Specific examples of Compound (I) obtained by various methods are shown in Table 1.

Numbering of substitution positions in Table 1 and Table 5 later described does not necessarily harmonize with the correct nomenclature [cf. see (NOTE) below]; but for purpose of simplicity, numbering of the substitution positions is systematically made as illustrated below, wherein positional numbering within parenthesis indicates the case where L is —S—.

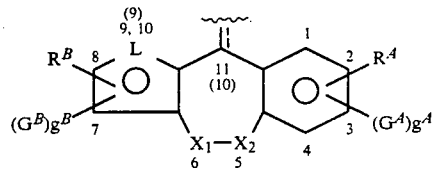

NOTE

In cycloheptene derivatives (wherein L is —CH=CH—; and $X_1-X_2$ is —CH$_2$CH$_2$—or —CH=CH—), despite the positional number in the general formula above, for example, a substituent on the carbon at the 2-position in the formula above is correctly given as a substituent at the 3-position. However, in the tables, according to the positional numbering in the formula described above, —COOH on the carbon at the 2-position is indicated to be 2—COOH (correctly 3-COOH).

Further in thienobenzo derivatives (wherein L is —S—), for example, —COOH which should correctly be a substituent on the 8-position is likewise indicated as 2-COOH in the tables.

TABLE 1

| L | $X_1-X_2$ | $(G^A)g^A/(G^B)g^B$ | $-W-(CH_2)_n-Z-$ | Q | $R^A/R^B$ | Compound No. |
|---|---|---|---|---|---|---|
| —CH=CH— | —CH$_2$—O— | none | -S⌒NHSO$_2$O— | ⟨phenyl⟩ | 2-COOCH$_3$ | 1a |
| " | " | " | " | " | 2-COOH | 1b |
| " | " | " | " | " | 2-CH$_2$COOCH$_3$ | 2a |
| " | " | " | " | " | 2-CH$_2$COOH | 2b |
| " | " | " | " | " | 3-COOCH$_3$ | 3a |
| " | " | " | " | " | 3-COOH | 3b |
| " | " | " | " | " | 9-COOCH$_3$ | 4a |
| " | " | " | " | " | 9-COOH | 4b |
| " | " | " | -S⌒CH$_3$\|NSO$_2$— | " | 2-COOCH$_3$ | 5a |

TABLE 1-continued

| L | $X_1$—$X_2$ | $(G^A)g^A/(G^B)g^B$ | —W—$(CH_2)_n$—Z— | Q | $R^A/R^B$ | Compound No. |
|---|---|---|---|---|---|---|
| " | " | " | " | " | 2-COOH | 5b |
| —CH=CH— | —CH$_2$—O— | 9-Br | —S~~~NHSO$_2$— | (phenyl) | 2-COOCH$_3$ | 6a |
| " | " | " | " | " | 2-COOH | 6b |
| " | " | none | " | (2-nitrophenyl, O$_2$N) | 2-COOCH$_3$ | 7a |
| " | " | " | " | " | 2-COOH | 7b |
| " | " | " | " | (3-nitrophenyl, NO$_2$) | 2-COOCH$_3$ | 8a |
| " | " | " | " | " | 2-COOH | 8b |
| " | " | " | " | (4-nitrophenyl, NO$_2$) | 2-COOCH$_3$ | 9a |
| " | " | " | " | " | 2-COOH | 9b |
| " | " | " | " | (4-fluorophenyl, F) | 2-COOCH$_3$ | 10a |
| " | " | " | " | " | 2-COOH | 10b |
| —CH=CH— | —CH$_2$—O— | none | —S~~~NHSO$_2$— | (4-chlorophenyl, Cl) | 2-COOCH$_3$ | 11a |
| " | " | " | " | " | 2-COOH | 11b |
| " | " | " | " | (4-methylphenyl, CH$_3$) | 2-COOCH$_3$ | 12a |
| " | " | " | " | " | 2-COOH | 12b |
| " | " | " | " | (4-methoxyphenyl, OCH$_3$) | 2-COOCH$_3$ | 13a |
| " | " | " | " | " | 2-COOH | 13b |
| " | " | " | " | (naphthyl) | 2-COOCH$_3$ | 14a |
| " | " | " | " | " | 2-COOH | 14b |

TABLE 1-continued
| L | $X_1-X_2$ | $(G^A)g^A/(G^B)g^B$ | $-W-(CH_2)_n-Z-$ | Q | $R^A/R^B$ | Compound No. |
|---|---|---|---|---|---|---|
| " | " | " | " | 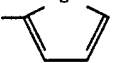 | 2-COOCH$_3$ | 15a |
| " | " | " | " | " | 2-COOH | 15b |
| $-CH=CH-$ | $-CH_2-O-$ | none |  | 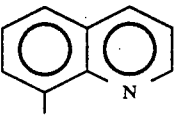 | 2-COOCH$_3$ | 16a |
| " | " | " | " | " | 2-COOH | 16b |
| " | " | " | " | 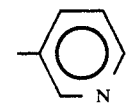 | 2-COOCH$_3$ | 17a |
| " | " | " | " | " | 2-COOH | 17b |
| " | " | " | " | 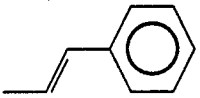 | 2-COOCH$_3$ | 18a |
| " | " | " | " | " | 2-COOH | 18b |
| " | " | " | " | 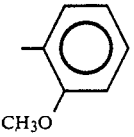 | 2-COOCH$_3$ | 19a |
| " | " | " | " | " | 2-COOH | 19b |
| " | " | " | " | 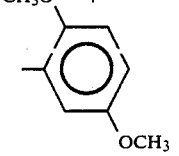 | 2-COOCH$_3$ | 20a |
| " | " | " | " | " | 2-COOH | 20b |
| $-CH=CH-$ | $-CH_2-O-$ | none | 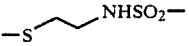 | 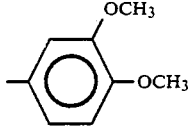 | 2-COOCH$_3$ | 21a |
| " | " | " | " | " | 2-COOH | 21b |
| " | " | " | " | 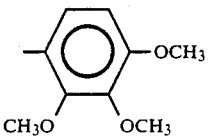 | 2-COOCH$_3$ | 22a |
| " | " | " | " | " | 2-COOH | 22b |
| " | " | " | " | 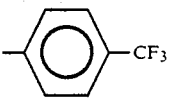 | 2-COOCH$_3$ | 23a |

TABLE 1-continued

| L | X₁—X₂ | $(G^A)g^A/(G^B)g^B$ | —W—(CH₂)ₙ—Z— | Q | $R^A/R^B$ | Compound No. |
|---|---|---|---|---|---|---|
| " | " | " | " | " | 2-COOH | 23b |
| " | " | " | —NH-CH₂CH₂-NHSO₂— | phenyl | 2-COOC₂H₅ | 24a |
| " | " | " | " | " | 2-COOH | 24b |
| " | " | " | —NH-(CH₂)₃-NHSO₂— | " | 2-COOCH₃ | 25a |
| " | " | " | " | " | 2-COOH | 25b |
| —CH=CH— | —CH₂—O— | none | —O-CH₂CH₂-NHSO₂— | phenyl | 2-COOCH₃ | 26a |
| " | " | " | " | " | 2-COOH | 26b |
| " | " | " | —NHCO-CH₂-NHSO₂— | " | 2-COOCH₃ | 27a |
| " | " | " | " | " | 2-COOH | 27b |
| " | " | " | =CH-CH₂CH₂-NHSO₂— | " | 2-COOCH₃ | 28a |
| " | " | " | " | " | 2-COOH | 28b |
| " | " | " | " | " | 2-CH₂COOCH₃ | 29a |
| " | " | " | " | " | 2-CH₂COOH | 29b |
| " | " | " | =CH-CH₂-NHSO₂— | " | 2-COOCH₃ | 30a |
| " | " | " | " | " | 2-COOH | 30b |
| —CH=CH— | —CH₂—O— | none | —CH₂-CH₂CH₂-NHSO₂— | phenyl | 2-COOCH₃ | 31a |
| " | " | " | " | " | 2-COOH | 31b |
| " | " | " | —S-CH₂CH₂-NHCO— | " | 2-COOCH₃ | 32a |
| " | " | " | " | " | 2-COOH | 32b |
| " | " | " | " | 3-methoxyphenyl | 2-COOCH₃ | 33a |
| " | " | " | " | " | 2-COOH | 33b |
| " | " | " | " | 3-hydroxyphenyl | 2-COOCH₃ | 34a |
| " | " | " | " | " | 2-COOH | 34b |

TABLE 1-continued

| L | $X_1-X_2$ | $(G^A)g^A/(G^B)g^B$ | $-W-(CH_2)_n-Z-$ | Q | $R^A/R^B$ | Compound No. |
|---|---|---|---|---|---|---|
| " | " | " | " | 2,6-dimethoxy-3-methylphenyl (CH₃O, CH₃O with CH₃) | 2-COOCH₃ | 35a |
| " | " | " | " | " | 2-COOH | 35b |
| —CH=CH— | —CH₂—O— | none | —S—CH₂CH₂—NHCO— | 2,3,4-trimethoxyphenyl (with methyl) | 2-COOCH₃ | 36a |
| " | " | " | " | " | 2-COOH | 36b |
| " | " | " | " | 2,3,4-trimethoxyphenyl (alternate) | 2-COOCH₃ | 37a |
| " | " | " | " | " | 2-COOH | 37b |
| " | " | " | " | 3-methylthien-2-yl | 2-COOCH₃ | 38a |
| " | " | " | " | " | 2-COOH | 38b |
| " | " | " | " | cyclohexyl (H) | 2-COOCH₃ | 39a |
| " | " | " | " | " | 2-COOH | 39b |
| " | " | " | " | —(CH₂)₅CH₃ | 2-COOCH₃ | 40a |
| " | " | " | " | " | 2-COOH | 40b |
| —CH=CH— | —CH₂—O— | none | —S—CH₂CH₂—NHCO— | styryl-phenyl (CH=CH—Ph) | 2-CH₂COOCH₃ | 41a |
| " | " | " | " | " | 2-CH₂COOH | 41b |
| " | " | " | " | coumarin-3-yl | 2-CH₂COOCH₃ | 42a |
| " | " | " | " | " | 2-CH₂COOH | 42b |
| " | " | " | =CH—CH₂—NHCO— | phenyl | 2-COOCH₃ | 43a |
| " | " | " | " | " | 2-COOH | 43b |

TABLE 1-continued

| L | $X_1-X_2$ | $(G^A)g^A/(G^B)g^B$ | $-W-(CH_2)_n-Z-$ | Q | $R^A/R^B$ | Compound No. |
|---|---|---|---|---|---|---|
| " | " | " | $-S\underset{}{\diagdown}\diagup^{NHCONH-}$ | " | 2-COOCH$_3$ | 44a |
| " | " | " | " | " | 2-COOH | 44b |
| " | " | " | " | " | 2-CH$_2$COOCH$_3$ | 45a |
| " | " | " | " | " | 2-CH$_2$COOH | 45b |
| $-CH=CH-$ | $-CH_2-O-$ | none | $-S\underset{}{\diagdown}\diagup^{NHCSNH-}$ | phenyl | 2-COOCH$_3$ | 46a |
| " | " | " | " | " | 2-COOH | 46b |
| " | " | " | $-S\underset{}{\diagdown}\diagup^{NHNHCONH-}$ | " | 2-COOCH$_3$ | 47a |
| " | " | " | " | " | 2-COOH | 47b |
| " | " | " | $-S\underset{}{\diagdown}\diagup^{NHNHCSNH-}$ | " | 2-COOCH$_3$ | 48a |
| " | " | " | " | " | 2-COOH | 48b |
| " | " | " | $=CH\underset{}{\diagdown}\diagup^{NHCONH-}$ | " | 2-COOCH$_3$ | 49a |
| " | " | " | " | " | 2-COOH | 49b |
| " | " | " | $=CH\underset{}{\diagdown}\diagup^{NHCONH-}$ | " | 2-COOCH$_3$ | 50a |
| " | " | " | " | " | 2-COOH | 50b |
| $-CH=CH-$ | $-CH_2-O-$ | none | $=CH\underset{}{\diagdown}\diagup^{NHNHCOHN-}$ | phenyl | 2-COOCH$_3$ | 51a |
| " | " | " | " | " | 2-COOH | 51b |
| " | " | " | $=CH\underset{}{\diagdown}\diagup^{NHNHCSHN-}$ | " | 2-COOCH$_3$ | 52a |
| " | " | " | " | " | 2-COOH | 52b |
| " | " | " | $-S\underset{}{\diagdown}\diagup^{NHCOO-}$ | " | 2-COOCH$_3$ | 53a |
| " | " | " | " | " | 2-COOH | 53b |
| " | " | " | $-S\underset{}{\diagdown}\diagup^{NHCOS-}$ | " | 2-COOCH$_3$ | 54a |
| " | " | " | " | " | 2-COOH | 54b |
| " | $-CH_2-S-$ | " | $-S\underset{}{\diagdown}\diagup^{NHSO_2-}$ | " | 2-COOCH$_3$ | 55a |
| " | " | " | " | " | 2-COOH | 55b |
| $-CH=CH-$ | $-CH_2-S-$ | none | $-NH\underset{}{\diagdown}\diagup^{NHSO_2-}$ | phenyl | 2-COOCH$_3$ | 56a |
| " | " | " | " | " | 2-COOH | 56b |

TABLE 1-continued

| L | $X_1$—$X_2$ | $(G^A)g^A/(G^B)g^B$ | —W—$(CH_2)_n$—Z— | Q | $R^A/R^B$ | Compound No. |
|---|---|---|---|---|---|---|
| " | " | " | —S~~NHSO$_2$— | (styryl-phenyl) | 2-COOCH$_3$ | 57a |
| " | " | " | " | " | 2-COOH | 57b |
| " | " | " | —S~~NHCONH— | (phenyl) | 2-COOCH$_3$ | 58a |
| " | " | " | " | " | 2-COOH | 58b |
| " | —CH$_2$—CH$_2$— | " | —S~~NHSO$_2$— | " | 2-COOCH$_3$ | 59a |
| " | " | " | " | " | 2-COOH | 59b |
| " | " | " | " | (styryl-phenyl) | 2-COOCH$_3$ | 60a |
| " | " | " | " | " | 2-COOH | 60b |
| —CH=CH— | —CH$_2$—CH$_2$— | none | —S~~NHCONH— | (phenyl) | 2-COOCH$_3$ | 61a |
| " | " | " | " | " | 2-COOH | 61b |
| " | " | " | —S~~NHNHCONH— | " | 2-COOCH$_3$ | 62a |
| " | " | " | " | " | 2-COOH | 62b |
| " | " | " | —CH$_2$~~NHSO$_2$— | " | 2-COOCH$_3$ | 63a |
| " | " | " | " | " | 2-COOH | 63b |
| " | —CH=CH— | " | —S~~NHSO$_2$— | " | 2-COOCH$_3$ | 64a |
| " | " | " | " | " | 2-COOH | 64b |
| " | " | " | " | (styryl-phenyl) | 2-COOCH$_3$ | 65a |
| " | " | " | " | " | 2-COOH | 65b |
| —CH=CH— | —CH=CH— | none | —S~~NHNHCONH— | (phenyl) | 2-COOCH$_3$ | 66a |
| " | " | " | " | " | 2-COOH | 66b |
| —S— | —CH$_2$—O— | " | —S~~NHSO$_2$— | " | 2-CH$_2$COOCH$_3$ | 67a |
| " | " | " | " | " | 2-CH$_2$COOH | 67b |

Chemical

The thus produced Compound (I) has a strongly antagonizing activity against TXA$_2$. Among Compound (I), Compound (I-1) having the following structure:

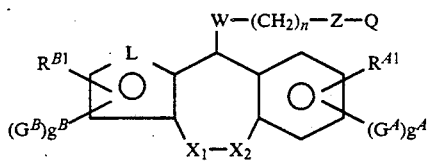

(I-1)

wherein ═, $X_1-X_2$, L, $R^A$, $R^B$, $G^A$, $G^B$, Wb, $R^1$, Q, n, $g^A$ and $g^B$ have the same significances as described above are particularly preferred.

Specific examples of Compound (I-1) are shown in Table 2.

Furthermore, specific examples of particularly preferred Compound (I-1) are shown in Table 3.

Names of the compounds in Table 2, Table 3, Reference Examples and Examples harmonize with the formal nomenclature.

TABLE 2

| Compound | Compound No. |
|---|---|
| 11-[2-[(Phenylsulfonyl)amino]ethyl]thio-6,11-dihydrodibenz[b,e]oxepin-2-carboxylic acid | 1b |
| 11-[2-[(Phenylsulfonyl)amino]ethyl]thio-6,11-dihydrodibenz[b,e]oxepin-2-acetic acid | 2b |
| 9-Bromo-11-[2-[(phenylsulfonyl)amino]ethyl]thio-6,11-dihydrodibenz[b,e]oxepin-2-carboxylic acid | 6b |
| 11-[2-[(2-Nitrophenylsulfonyl)amino]ethyl]thio-6,11-dihydrodibenz[b,e]oxepin-2-carboxylic acid | 7b |
| 11-[2-[(3-Nitrophenylsulfonyl)amino]ethyl]thio-6,11-dihydrodibenz[b,e]oxepin-2-carboxylic acid | 8b |
| 11-[2-[(4-Nitrophenylsulfonyl)amino]ethyl]thio-6,11-dihydrodibenz[b,e]oxepin-2-carboxylic acid | 9b |
| 11-[2-[(4-Fluorophenylsulfonyl)amino]ethyl]thio-6,11-dihydrodibenz[b,e]oxepin-2-carboxylic acid | 10b |
| 11-[2-[(4-Chlorophenylsulfonyl)amino]ethyl]thio-6,11-dihydrodibenz[b,e]oxepin-2-carboxylic acid | 11b |
| 11-[2-[(4-Methylphenylsulfonyl)amino]ethyl]thio-6,11-dihydrodibenz[b,e]oxepin-2-carboxylic acid | 12b |
| 11-[2-[(4-Methoxyphenylsulfonyl)amino]ethyl]thio-6,11-dihydrodibenz[b,e]oxepin-2-carboxylic acid | 13b |
| 11-[2-[(2-Thienylsulfonyl)amino]ethyl]thio-6,11-dihydrodibenz[b,e]oxepin-2-carboxylic acid | 15b |
| 11-[2-[(3-Pyridylsulfonyl)amino]ethyl]thio-6,11-dihydrodibenz[b,e]oxepin-2-carboxylic acid | 17b |
| 11-[2-[(Styrylsulfonyl)amino]ethyl]thio-6,11-dihydrodibenz[b,e]oxepin-2-carboxylic acid | 18b |
| 11-[2-[(2,5-Dimethoxyphenylsulfonyl)amino]ethyl]thio-6,11-dihydrodibenz[b,e]oxepin-2-carboxylic acid | 20b |
| 11-[2-[(3,4-Dimethoxyphenylsulfonyl)amino]ethyl]thio-6,11-dihydrodibenz[b,e]oxepin-2-carboxylic acid | 21b |
| 11-[2-[(4-Trifluoromethylphenylsulfonyl)amino]ethyl]thio-6,11-dihydrodibenz[b,e]oxepin-2-carboxylic acid | 23b |
| 11-[2-[(Phenylsulfonyl)amino]ethyl]amino-6,11-dihydrodibenz[b,e]oxepin-2-carboxylic acid | 24b |
| (E)-11-[3-(Phenylsulfonyl)amino]propylidene-6,11-dihydrodibenz[b,e]oxepin-2-carboxylic acid | E-28b |
| (E)-11-[2-(Phenylsulfonyl)amino]ethylidene-6,11-dihydrodibenz[b,e]oxepin-2-carboxylic acid | E-30b |
| 11-[2-[(Benzoyl)amino]ethyl]thio-6,11-dihydrodibenz[b,e]oxepin-2-carboxylic acid | 32b |
| 11-[2-[(2-Methoxybenzoyl)amino]ethyl]thio-6,11-dihydrodibenz[b,e]oxepin-2-carboxylic acid | 33b |
| 11-[2-[(2-Hydroxybenzoyl)amino]ethyl]thio-6,11-dihydrodibenz[b,e]oxepin-2-carboxylic acid | 34b |
| 11-[2-[(2,6-Dimethoxybenzoyl)amino]ethyl]thio-6,11-dihydrodibenz[b,e]oxepin-2-carboxylic acid | 35b |
| 11-[2-[(3,4,5-Trimethoxybenzoyl)amino]ethyl]thio-6,11-dihydrodibenz[b,e]oxepin-2-carboxylic acid | 36b |
| 11-[2-[(2,3,4-Trimethoxybenzoyl)amino]ethyl]thio-6,11-dihydrodibenz[b,e]oxepin-2-carboxylic acid | 37b |
| 11-[2-[(2-Methylthenoyl)amino]ethyl]thio-6,11-dihydrodibenz[b,e]oxepin-2-carboxylic acid | 38b |
| 11-[2-[(Cinnamoyl)amino]ethyl]thio-6,11-dihydrodibenz[b,e]oxepin-2-acetic acid | 41b |
| 11-[2-[[Coumarin-3-yl)carbonyl]amino]ethyl]thio-6,11-dihydrodibenz[b,e]oxepin-2-acetic acid | 42b |
| 11-[2-[(3-Phenylureido)ethyl]thio-6,11-dihydrodibenz[b,e]oxepin-2-carboxylic acid | 44b |
| 11-[2-[(3-Benzyl)thioureido)ethyl]thio-6,11-dihydrodibenz[b,e]oxepin-2-carboxylic acid | 46b |
| 11-[2-[(phenylsulfonyl)amino]ethyl]thio-6,11-dihydrodibenzo[b,e]thiepin-2-carboxylic acid | 55b |
| 5-[2-[(phenylsulfonyl)amino]ethyl]thio-10,11-dihydro-5H-dibenzo[a,d]cyclohepten-3-carboxylic acid | 59b |
| 5-[2-[(Styrylsulfonyl)amino]ethyl]thio-10,11-dihydro-5H-dibenzo[a,d]cyclohepten-3-carboxylic acid | 60b |
| 5-[2-[(phenylsulfonyl)amino]ethyl]thio-5H-dibenzo[a,d]cyclohepten-3-carboxylic acid | 64b |
| 5-[2-[(Styrylsulfonyl)amino]9 ethyl]thio-5H-dibenzo[a,d]cyclohepten-3-carboxylic acid | 65b |

TABLE 3

| Compound | Compound No. |
|---|---|
| 11-[2-[(Phenylsulfonyl)amino]ethyl]thio-6,11-dihydrodibenz[b,e]oxepin-2-carboxylic acid | 1b |
| 11-[2-[(Phenylsulfonyl)amino]ethyl]thio-6,11-dihydrodibenz[b,e]oxepin-2-acetic acid | 2b |
| 9-Bromo-11-[2-[(phenylsulfonyl)amino]ethyl]thio-6,11-dihydrodibenz[b,e]oxepin-2-carboxylic acid | 6b |
| 11-[2-[(2-Nitrophenylsulfonyl)amino]ethyl]thio-6,11-dihydrodibenz[b,e]oxepin-2-carboxylic acid | 7b |
| 11-[2-[(3-Nitrophenylsulfonyl)amino]ethyl]thio-6,11-dihydrodibenz[b,e]oxepin-2-carboxylic acid | 8b |
| 11-[2-[(4-Nitrophenylsulfonyl)amino]ethyl]thio-6,11-dihydrodibenz[b,e]oxepin-2-carboxylic acid | 9b |
| 11-[2-[(4-Fluorophenylsulfonyl)amino]ethyl]thio-6,11-dihydrodibenz[b,e]oxepin-2-carboxylic acid | 10b |
| 11-[2-[(4-Chlorophenylsulfonyl)amino]ethyl]thio-6,11-dihydrodibenz[b,e]oxepin-2-carboxylic acid | 11b |
| 11-[2-[(4-Methylphenylsulfonyl)amino]ethyl]thio-6,11-dihydrodibenz[b,e]oxepin-2-carboxylic acid | 12b |
| 11-[2-[(4-Methoxyphenylsulfonyl)amino]ethyl]thio-6,11-dihydrodibenz[b,e]oxepin-2-carboxylic acid | 13b |
| 11-[2-[(2-Thienylsulfonyl)amino]ethyl]thio-6,11-dihydrodibenz[b,e]oxepin-2-carboxylic acid | 15b |
| 11-[2-[(Styrylsulfonyl)amino]ethyl]thio-6,11-dihydrodibenz[b,e]oxepin-2-carboxylic acid | 18b |
| 11-[2-[(4-Trifluoromethylphenylsulfonyl)amino]ethyl]thio-6,11-dihydrodibenz[b,e]oxepin-2-carboxylic acid | 23b |
| (E)-11-[2-(Phenylsulfonyl)amino]ethylidene-6,11-dihydrodibenz[b,e]oxepin-2-carboxylic acid | E-30b |
| 11-[2-[(2-Methoxybenzoyl)amino]ethyl]thio-6,11-dihydrodibenz[b,e]oxepin-2-carboxylic acid | 33b |
| 11-[2-[(2-Hydroxybenzoyl)amino]ethyl]thio-6,11-dihydrodibenz[b,e]oxepin-2-carboxylic acid | 34b |
| 11-[2-[(Phenylsulfonyl)amino]ethyl]thio-6,11-dihydrodibenzo[b,e]thiepin-2-carboxylic acid | 55b |
| 5-[2-[(Phenylsulfonyl)amino]9 ethyl]thio-10,11-dihydro-5H-dibenzo[a,d]cyclohepten-3-carboxylic acid | 59b |
| 5-[2-[(Styrylsulfonyl)amino]ethyl]thio-10,11-dihydro-5H-dibenzo[a,d]cyclohepten-3-carboxylic acid | 60b |
| 5-[2-[(Phenylsulfonyl)amino]ethyl]thio-5H-dibenzo[a,d]cyclohepten-3-carboxylic acid | 64b |
| 5-[2-[(Styrylsulfonyl)amino]ethyl]thio-5H-dibenzo[a,d]cyclohepten-3-carboxylic acid | 65b |

Next, $TXA_2$ antagonizing activity of Compound (I) is described below.

Test on anti-platelet activity ($TXA_2$ antagonizing test)

Using guinea pig platelet, influence of the compounds in accordance with the present invention on platelet aggregation induced by U-46619 (9,11-dideoxy-9α,11α-methanoepoxyprostaglandin $F_2\alpha$; manufactured by Cayman Chemica Co., Ltd.) which was a $TXA_2$/prostaglandin $H_2$ receptor stimulant was examined.

Male guinea pig (Hartley strain; body weight, 300 to 600 g) was anesthesized by intraperitoneal administration of sodium pentobarbital (30 mg/kg) and blood was collected from the descending aorta of the abdomen with a 1/10 volume of sodium citrate. By centrifugation (KC-70: manufactured by Kubota Co., Ltd.) at 800 rpm for 10 minutes, platelet rich plasma (PRP) was collected. Platelet aggregation induced by U-46619 (0.5–1 $\mu$M) was determined by photometry [Born, G. V. R. et al., Nature (London), 194, 927–929 (1962)]. A test compound was pretreated before 3 minutes and an ability of inhibiting aggregation was measured. The minimum concentration of inhibiting platelet aggregation by 30% or more was defined as the minimum effective concentration (MEC) of the test compound.

The results are shown in Table 4.

Acute toxicity test

Using three dd strain male mice weighing 20±1 g, a test compound was orally (po; 300 mg/kg) or intraperitoneally (ip; 100 mg/kg) administered. MLD (the minimum lethal dose) was determined by observing the mortality for seven days after administration.

The results are shown in Table 4.

TABLE 4

| Compound No.** | Acute Toxicity (MLD) mg/kg | | TXA$_2$ Antagonizing Activity (MEC) $\mu$g/ml |
|---|---|---|---|
| | po | ip | |
| 1b | >300 | >100 | 0.3 |
| 1b' | >300 | >100 | 0.3 |
| 6b | >300 | >100 | 0.03 |
| 10b | >300 | >100 | 0.3 |
| 15b | >300 | >100 | 0.3 |
| 16b | >300 | >100 | 3 |
| 24b | >300 | >100 | 3 |
| E-29b | >300 | >100 | 1 |
| 33b | >300 | >100 | 0.3 |
| 55b | >300 | >100 | 3 |
| BM13177* (reference compound) | >300 | >100 | 3 |

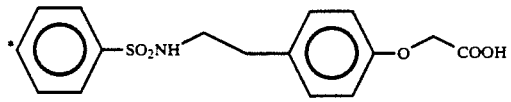

**In Compound No., symbol ' indicates an addition product of the corresponding compound in Tables 1 through 3 to a salt or solvent and, symbols E and Z represent E-form and Z-form, respectively (hereafter the symbols have the same significances).

As demonstrated in Table 4, Compound (I) and pharmaceutically acceptable salts thereof possess a TXA$_2$ antagonizing activity.

Compound (I) and pharmaceutically acceptable salts thereof may be administered singly as they are, but in general, it is preferably administered as various medical preparations. These medical preparations are used for animals and human beings.

The medical preparation in accordance with the present invention may contain, as an active ingredient, Compound (I) or pharmaceutically acceptable salts thereof singly or as admixture with other optional effective components for different treatment. Further these medical preparations can be produced by optional procedures well known in the pharmaceutical field, by mixing the active ingredient together with one or more pharmaceutically acceptable carriers.

Herein, as the optional effective components for different treatment contained togethwer with Compound (I) or pharmaceutically acceptable salts thereof, mention may be made of, for example, a steroid, a nonsteroid antiinflammatory agent, a peripheral analgesic, a leucotriene antagonist, a leucotriene biosynthesis inhibitor, an H$_2$ receptor antagonist, an antihistaminic agent, a histamine release inhibitor, a bronchodilator, an angiotensin converting enzyme inhibitor, a thromboxane A$_2$ biosynthesis inhibitor, an H+-K+ATPase inhibitor, a coronary dilator, a calcium antagonist, a diuretic, a xanthine oxidase inhibitor, a cerebral circulation improving agent, a celebral metabolism activator, a cerebral protecting agent, an antiplatelet agent, a thrombolytic agent, an adrenaline $\alpha$ receptor antagonist, an adrenergic $\beta$ receptor agent, an adrenaline $\beta$ receptor antagonist, a serotonine antagonist, a platelet activation factor (PAF) antagonist, adenosine receptor antagonist, antihyperlipidemic agent, cholesterol biosynthesis inhibitor, immunostimulating agent, immunosuppressive agent, anticancer agent, etc.

It is preferred that the most effective route for treatment be selected as a route for administration. Oral or parenteral administration such as intrarectal, topical, intranasal, intraocular, intrabuccal, subcutaneous, intramuscular and intravenous routes, etc. are mentioned.

As the form of administration, there are a capsule, a tablet, a granule, a powder, a syrup, an emulsion, a suppository, an ointment, an eyedrop, a nosedrop, a troche, an aerosol, an injection, etc.

A liquid preparation suited for oral administration, for example, an emulsion and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as a p-hydroxybenzoic acid ester, etc.; flavors such as strawberry flavor, pepper mint, etc. Further a capsule, a tablet, a powder and a granule, etc. can be prepared using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as an aliphatic ester, etc.; a plasticizer such as glyceiine, etc.

A preparation suited for parenteral administration is composed of a sterile aqueous preparation containing active compounds which are preferably isotonic to blood of recipient. For example, with an injection, a solution for injection is prepared using carriers composed of a saline solution, a glucose solution or a mixture of saline water and glucose solution.

A nasal spray preparation is comprised of a purified aqueous solution of the active compounds which contains an antiseptic and an isotonic agent. Such a preparation is adjusted to pH compatible with nasal membrane and to an isotonic state.

An ocular preparation is prepared in a manner similar to the nasal spray, except that pH and isotonic factors are controlled so as to fit those of eyes.

A topical preparation is prepared by dissolving or suspending the active compound in one or more media, for example, a mineral oil, petroleum, a polyvalent alcohol or other bases used for topical medical preparations.

A preparation for rectal administration is provided as a suppository using conventional carriers, for example, cacao fat, hydrogenated fat or hydrogenated fat carboxylic acid, etc.

Further these parenteral preparations may also be added with one or more auxiliary components such as a diluent, a fragrance, an antiseptic (including an antioxidant), an excipient, a disintegrator, a lubricant, a binder, a surfactant, a plasticizer and the like.

Effective dose and number of administration of Compound (I) or pharmaceutically acceptable salts thereof vary depending upon mode of administration, age and body weight of the patient and properties or severity of conditions to be treated. In general, daily dose is 0.01 to 1000 mg/person and number in administration is once a day, or the dosage may be divided into several ones.

Hereafter, the present invention is described by referring to Reference Examples and Examples below.

Intermediates obtained in the following Reference Examples are shown in Table 5.

room temperature for an hour, 19.4 g of boron trifluoride ethyl ether complex was added to the mixture followed by stirring at room temperature for 2 hours. The reaction solution was poured into ice water. The organic layer was washed with a diluted sodium hydoxide aqueous solution and then with water and dried over anhydrous magnesium sulfate. Concentration under reduced pressure gave 335.3 g of the desired compound as white crystals.

Melting point:128–129° C.

Elemental analysis: as $C_{16}H_{12}O_4$

TABLE 5

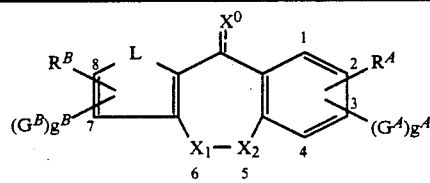

| Compound (Reference Example) | L | $X_1-X_2$ | $(G^A)g^A/(G^B)g^B$ | $R^A/R^B$ | $-X^0$ |
|---|---|---|---|---|---|
| a (1) | —CH=CH— | —CH$_2$—O— | none | 2-COOCH$_3$ | =O |
| b (2) | " | " | " | " | —OH |
| c (3) | " | " | " | 2-COOC$_2$H$_5$ | " |
| d (4) | " | " | " | 2-CH$_2$COOCH$_3$ | =O |
| e (5) | " | " | " | " | —OH |
| f (6) | " | " | " | 2-COOCH$_3$ | —SCH$_2$CH$_2$NH$_2$ |
| g (7) | " | " | " | 2-COOC$_2$H$_5$ | —NHCH$_2$CH$_2$NH$_2$ |
| h (8) | " | " | " | 2-COOCH$_3$ | —NH(CH$_2$)$_3$NH$_2$ |
| i (9) | " | " | " | " | =CHCH$_2$CH$_2$NH$_2$ |
| j (10) | —CH=CH— | —CH$_2$—O— | none | 2-CH$_2$COOCH$_3$ | =CHCH$_2$CH$_2$NH$_2$ |
| k (11) | " | " | " | 2-COOCH$_3$ | =CHCH$_2$NH$_2$ |
| l (12) | " | " | 9-Br | " | —SCH$_2$CH$_2$NH$_2$ |
| m (13) | " | " | none | 3-COOCH$_3$ | " |
| n (14) | " | " | " | 9-COOCH$_3$ | " |
| o (15) | " | " | " | 2-CH$_2$COOCH$_3$ | " |
| p (16) | " | " | " | 2-COOCH$_3$ | —SCH$_2$CH$_2$NHCH$_3$ |
| q (17) | " | —CH$_2$—S— | " | " | —OCH$_3$ |
| r (18) | " | " | " | " | —SCH$_2$CH$_2$NH$_2$ |
| s (19) | " | —CH$_2$CH$_2$— | " | " | " |
| t (20) | " | —CH—CH— | " | " | " |
| u (21) | —S— | —CH$_2$—O— | " | 2-CH$_2$COOCH$_3$ | " |

REFERENCE EXAMPLE 1

Methyl 11-oxo-6,11-dihydrodibenz[b,e]oxepin-2-carboxylate(-Compound a)

A mixture of 348.9 g of methyl p-hydroxybenzoate sodium salt, 402.4 g of phthalide and 200 g of sodium chloride was stirred at 150° C. for 6 hours. After completion of the reaction, the mixture was cooled to room temperature and 4 liters of 10% acetic acid aqueous solution were added thereto. The mixture was allowed to stand at room temperature overnight. After stirring at room temperature for 3 hours, crystals were filtered. To the crystals was added 6 liters of water. After stirring at room temperature for 30 minutes, the crystals were taken out by filtration. To the crystals was added 3 liters of toluene. The mixture was stirred at room temperature for an hour. The crystals were taken out by filtration and dried by heating under reduced pressure to give 393.9 g of 2-(4-methoxycarbonylphenoxy)-methyl benzoate.

IR(KBr tablet, cm-1):3400, 1700, 1610, 1260, 1235

In 5.0 liters of methylene chloride was suspended 392.7 g of the thus obtained 2-(4-methoxycarbonylphenoxy)methyl benzoate and, 266.0 g of trifluoroacetic anhydride was added to the suspension. After stirring at

|  | C | H |
|---|---|---|
| Found (%) | 71.55 | 4.48 |
| Calcd. (%) | 71.63 | 4.51 |

NMR (CDCl$_3$, δ, ppm): 3.84 (s, 3H), 5.14 (s, 2H), 6.87–8.93 (m, 7H)

IR (KBr tablet, cm-1): 1710, 1650, 1610, 1250, 1010

REFERENCE EXAMPLE 2

Methyl 11-hydroxy-6,11-dihydrodibenz[b,e]oxepin-2-carboxylate (Compound b):

Compound a, 50 g, obtained in Reference Example 1 was suspended in 300 ml of methanol and 6.3 g of sodium borohydride was added to the suspension. The mixture was stirred at room temperature for 2 hours. After completion of the reaction, 10 ml of acetic acid and 300 ml of water were added thereto followed by stirring for 30 minutes. Insoluble matters were taken out by filtration and washed with methanol and then with water. By drying with heating under reduced pressure, 40 g of the desired compound was obtained.

NMR (CDCl$_3$, δ, ppm): 2.16 (s, 6H), 2.30–2.76 (m, 4H), 3.83 (s, 3H), 4.83 and 6.40 (ABq, J=12.6Hz, 2H), 5.01 (s, 1H), 6.79–7.93 (m, 7H)

IR (neat, cm$^{-1}$) : 2950, 1710, 1240, 1015

REFERENCE EXAMPLE 3

Ethyl 11-hydroxy-6,11-dihydrodibenz[b,e]oxepin-2-carboxylate (Compound c)

The corresponding starting material was used and treated in a manner similar to Reference Example 1 and Reference Example 2 to give the desired compound as colorless oil.

NMR (CDCl$_3$, δ, ppm): 1.31 (t, J=7Hz, 3H), 3.60 (d, J=3Hz, 1H), 4.25 (q, J=7Hz, 2H), 4.91 and 5.95 (ABq, J=12.5Hz, 2H), 5.61 (d, J=3Hz, 1H), 6.69–8.12 (m, 7H)

IR (neat, cm$^{-1}$): 3430, 1675, 1610, 1480, 1250

REFERENCE EXAMPLE 4

Methyl 11-oxo-6,11-dihydrodibenz[b,e]oxepin-2-acetate (Compound d)

The corresponding starting material was used and treated in a manner similar to Reference Example 1 to give the objective compound as light yellow crystals (recrystallized from methanol).

Melting point: 75°–76° C.

REFERENCE EXAMPLE 5

Methyl 11-hydroxy-6,11-dihydrodibenz[b,e]oxepin-2-acetate (Compound e)

The objective compound was obtained as light yellow crystals (recrystallized from diethyl ether) from Compound d obtained in Reference Example 4 in a manner similar to Reference Example 2.

Melting point: 85–87° C.

NMR (CDCl$_3$, δ, ppm): 2.08 (s, 3H), 3.49 (s, 2H), 3.59 (s, 3H), 4.89 and 5.75 (ABq, J=13Hz, 2H), 5.54 (bs, 1H), 6.7–7.4 (m, 7H)

REFERENCE EXAMPLE 6

Methyl 11-(2-aminoethyl)thio-6,11-dihydrodibenz[b,e]oxepin-2-carboxylate (Compound f)

In 300 ml of methylene chloride was dissolved 30.0 g of Compound b obtained in Reference Example 2. Under ice cooling, 10 ml of thionyl chloride was dropwise added to the solution. After stirring for further 2 hours under ice cooling, the reaction mixture was concentrated under reduced pressure. To the resulting residue, 500 ml of methanol and 20 ml of triethylamine were added and the mixture was stirred at room temperature for an hour. The solvent was distilled off under reduced pressure and the residue was extracted with 1 liter of ethyl acetate. The extract was washed in sequence with saturated aqueous sodium bicarbonate solution and then saturated sodium chloride aqueous solution. After drying over anhydrous sodium sulfate, the solvent was distilled off under reduced pressure. The obtained crude product was recrystallized from isopropyl ether to give 19.0 g of white crystalline methyl 11-methoxy-6,11-dihydrodibenz[b,e]oxepin-2-carboxylate.

NMR (CDCl$_3$, δ, ppm): 3.27 (s, 3H), 3.82 (s, 3H), 4.84 and 6.08 (ABq, J=12.1 Hz, 2H), 4.99 (s, 1H), 6.73–8.16 (m, 7H)

The aforesaid compound, 18.6 g, and 8.92 g of 2-aminoethanethiol hydrochloride were suspended in 300 ml of methylene chloride and 5 ml of boron trifluoride diethyl ether complex was added to the suspension. The mixture was stirred at room temperature for a day. The solvent was distilled off under reduced pressure and 200 ml of water was added to the residue. Further 1N sodium hydroxide aqueous solution was added thereto to adjust pH to 13. Furthermore, 100 ml of ether was added and the mixture was stirred at room temperature for 10 minutes. Insoluble matters were taken out by filtration and washed with ether. By drying with heating under reduced pressure, 16.6 g of the objective compound was obtained as colorless syrup.

NMR (CDCl$_3$, δ, ppm): 1.30 (s, 2H), 2.23–2.97 (m, 4H), 3.79 (s, 3H), 4.79 and 6.32 (ABq, J=12.5Hz, 2H), 4.93 (s, 1H), 6.72–7.83 (m, 7H)

IR (neat, cm$^{-1}$): 3370, 1710, 1240, 1115

REFERENCE EXAMPLE 7

Ethyl 11-(2-aminoethyl)amino-6,11-dihydrodibenz[b,e]oxepin-2-carboxylate (Compound g):

In 200 ml of methylene chloride was dissolved 10.0 g of Compound c obtained in Reference Example 3. Under ice cooling, 4 ml of thionyl chloride was dropwise added to the solution. After stirring for further 2 hours under ice cooling, the solvent was distilled off under reduced pressure. The residue was dissolved in 200 ml of methylene chloride. The solution was dropwise added to a solution of 50 ml of ethylenediamine in 500 ml of methylene chloride under ice cooling. After stirring for further 5 hours under ice cooling, the solvent was distilled off under reduced pressure. The residue was extracted with 500 ml of ethyl acetate. The extract was washed with saturated sodium chloride aqueous solution. After drying over anhydrous sodium sulfate, the solvent was distilled off under reduced pressure to give 11.0 g of the objective compound.

NMR (CDCl$_3$, δ, ppm): 1.34 (t, J=7.8Hz, 3H), 2.37–2.87 (m, 4H), 4.27 (q, J=7.8Hz, 2H), 4.59 (s, 1H), 4.75 and 6.54 (ABq, J=12.2Hz, 2H), 6.64–8.01 (m, 7H)

REFERENCE EXAMPLE 8

Methyl 11-(2-aminopropyl)amino-6,11-dihydrodibenz-[b,e]oxepin-2-carboxylate (Compound h)

The corresponding starting material was used and treated in a manner similar to Reference Example 7 to give the objective compound as yellow syrup.

NMR (CDCl$_3$, δ, ppm): 1.37–1.86 (m, 2H), 2.28–2.92 (m, 4H), 2.93 (bs, 2H), 3.77 (s, 3H), 4.57 (s, 1H), 4.75 and 6.52 (ABq, J=11.8Hz, 2H), 6.76 (d, J=8.5Hz, 1H), 7.02–7.39 (m, 4H), 7.72 (dd, J=2.2, 8.5Hz, 1H), 7.87 (d, J=2.2Hz, 1H)

IR (CHCl$_3$, cm$^{-1}$): 3662, 3064, 2952, 1713, 1612, 1289, 1133, 1004

REFERENCE EXAMPLE 9

Methyl (E,Z)-11-(3-aminopropylidene)-6,11-dihydrodibenz-[b,e]oxepin-2-carboxylate (Compound i)

In 250 ml of tetrahydrofuran was suspended 40.0 g of [3-[(tetrahydro-2H-pyran-2-yl)oxy]propyl]triphenylphosphonium bromide. In a nitrogen atmosphere, the suspension was ice cooled and 50 ml of n-butyl lithium/ hexane solution (1.6 normal) was dropwise added thereto. After stirring at room temperature for further an hour, 15.0 g of Compound a obtained in Reference Example 1 was added thereto followed by stirring at room temperature for 12 hours. 50 ml of water was added to the reaction mixture followed by extraction with 1 liter of ethyl acetate. The extract was washed with saturated sodium chloride aqueous solution 3 times. After drying over anhydrous sodium sulfate, the obtained residue was dissolved in 500 ml of dioxane and, 200 ml of water and 1.0 g of p-toluenesulfonic acid were added to the solution. The mixture was heated under reflux for an hour. The reaction mixture was concentrated under reduced pressure and the resulting residue was extracted with 1 liter of ethyl acetate. The extract was washed in sequence with saturated sodium bicarbonate aqueous solution and saturated sodium chloride aqueous solution and then dried over anhydrous sodium sulfate. The solvent was distilled off under reduced pressure, and the resulting residue was subjected to silica gel column chromatography (eluting solvent; toluene:ethyl acetate=1:1) to give 9.8 g of methyl (E,Z)-11-(3-hydroxy)propylidene-6,11-dihydrodibenz-[b,e]oxepin-2-carboxylate. A ratio of E/Z was approximately 3:7 according to NMR analysis.

The thus obtained product, 4.8 g, mainly composed of the Z-form and 10.0 g of p-toluenesulfonic acid were stirred at 100° C. for 42 hours in 250 ml of acetic acid. After completion of the reaction, the solvent was distilled off under reduced pressure and 200 ml of methanol was added to the residue. The mixture was heated under reflux for 3 hours. The solvent was distilled off under reduced pressure and the residue was extracted with 500 ml of ethyl acetate. The extract was washed with saturated sodium bicarbonate aqueous solution. After drying over anhydrous sodium sulfate, the solvent was distilled off under reduced pressure. The resulting residue was subjected to silica gel column chromatography (eluting solvent; hexane:ethyl acetate=1:1) to give 4.5 g of the product having an E/Z ratio of about 7:3.

NMR (CDCl$_3$, δ, ppm): 2.17-2.72 (m, 2H), 3.37-3.76 (m, 2H), 3.77 (s, 3H), 4.68-5.43 (m, 1H), 5.70 (t, J=7.4Hz, 0.9H; Z-form), 6.40 (t, J=6.9Hz, 2.1H; E-form), 6.52-8.12 (m, 7H)

The aforesaid compound having the E/Z of about 7:3, 3.5 g, was dissolved in 50 ml of pyridine and 1.7 ml of methanesulfonyl chloride was dropwise added to the solution under ice cooling. After stirring for further an hour under ice cooling, the solvent was distilled off under reduced pressure. The residue was extracted with 200 ml of ethyl acetate and the extract was washed in sequence with 1N hydrochloric acid aqueous solution, saturated sodium bicarbonate aqueous solution and then saturated sodium chloride aqueous solution. After drying over anhydrous magnesium sulfate, the solvent was distilled off under reduced pressure thereby to give 4.3 g of methyl (E,Z)-11-[3-(methylsulfonyl)oxy]propylidene-6,11-dihydrodibenz[b,e]oxepin- 2-carboxylate as colorless oil.

NMR (CDCl$_3$, δ, ppm): —SO$_2$CH$_3$; 2.93 (s, 2.1H; E-form), 3.00 (s, 0.9H; Z-form)

The aforesaid compound, 4.3 g, having an E/Z ratio of approximately 7:3 and 2.5 g of potassium phthalimide were stirred at room temperature for 2 days in 100 ml of dimethylformamide. The solvent was distilled off under reduced pressure and the residue was extracted with 300 ml of methylene chloride. The extract was washed with saturated sodium chloride aqueous solution. After drying over anhydrous magnesium sulfate, the solvent was distilled off under reduced pressure The obtained crude product was recrystallized from toluene to give 1.6 g of (E,Z)-N-[3-(2-methoxycarbonyl-6,11-dihydrodibenz-[b,e]oxepin-11-ylidene)propyl]-phthalimide. A ratio of E/Z was approximately 7:3.

Elemental analysis: as C$_{27}$H$_{21}$NO$_5$

|  | C | H | N |
|---|---|---|---|
| Found (%) | 73.66 | 4.91 | 3.25 |
| Calcd. (%) | 73.79 | 4.82 | 3.19 |

The aforesaid compound, 1.5 g, having an E/Z ratio of approximately 7:3 was heated under reflux for 7 hours in 100 ml of methanol, together with 0.2 ml of anhydrous hydrazine. The solvent was distilled off under reduced pressure to give 1.0 g of the crude desired compound as colorless oil. The compound was used for the subsequent reaction without further purification.

REFERENCE EXAMPLE 10

Methyl (E,Z)-11-(3-aminopropylidene)-6,11-dihydrodibenz-[b,e]oxepin-2-acetate (Compound j)

The corresponding starting material was used and treated in a manner similar to Reference Example 9 to give the desired compound as white solid (E/Z ratio: about 3:7).

NMR (CDCl$_3$, δ, ppm): 2.30-3.19 (m, 4H), 3.52 (s, 2H), 3.65 (s, 3H), 5.18 (bs, 2H), 5.70 (t, J=7.5Hz, 1H; Z-form), 6.75 (t, J=7.5Hz, 1H; E-form), 6.67-7.51 (m, 7H)

REFERENCE EXAMPLE 11

Methyl (E)-11-(2-aminoethylidene)-6,11-dihydrodibenz-[b,e]oxepin-2-acetate (Compound k)

The corresponding starting material was used and treated in a manner similar to Reference Example 9 to give the desired compound.

This compound was difficult to purify so that after the reaction solution was concentrated under reduced pressure, the concentrate was used for the next step, without performing purification.

MS (m/Z): 176 (M+)

REFERENCE EXAMPLE 12

Methyl 9-bromo-11-(2-aminoethyl)thio-6,11-dihydrodibenz[b,e]oxepin-2-carboxylate (Compound l)

The corresponding starting material was used and treated in a manner similar to Reference Example 6 to give the objective compound as yellow oil.

NMR (CDCl$_3$, δ, ppm): 1.42 (s, 2H), 2.5-2.7 (m, 2H), 2.7-2.95 (m, 2H), 3.88 (s, 3H), 4.86 and 6.36 (ABq, J=13.0Hz, 2H), 4.95 (s, 3H), 6.85 (d, J=8.6Hz, 1H), 7.1-7.5 (m, 3H), 7.81 (dd, J=8.6, 2.2Hz, 1H), 7.93 (d, J=2.2Hz, 1H)

MS (m/Z): 408 (M+)

REFERENCE EXAMPLE 13

Methyl 11-(2-aminoethyl)thio-6,11-dihydrodibenz-[b,e]oxepin-3-carboxylate (Compound m)

The corresponding starting material was used and treated in a manner similar to Reference Example 6 to give the objective compound as yellow brown oil.

NMR (CDCl$_3$, δ, ppm): 1.69 (bs, 2H), 2.31–3.00 (m, 4H), 3.82 (s, 3H), 4.84 and 6.23 (ABq, J=12.9Hz, 2H), 4.94 (s, 1H), 6.92–7.64 (m, 7H)

IR (CHCl$_3$, Cm$^{-1}$): 2954, 1720, 1282, 1097, 1033

REFERENCE EXAMPLE 14

Methyl 11-(2-aminoethyl)thio-6,11-dihydrodibenz-[b,e]oxepin-9-carboxylate (Compound n)

The corresponding starting material was used and treated in a manner similar to Reference Example 6 to give the yellow amorphous desired compound.

MS (m/Z): 329 (M+)

REFERENCE EXAMPLE 15

Methyl 11-(2-aminoethyl)thio-6,11-dihydrodibenz-[b,e]oxepin-2-acetate (Compound o)

Compound e obtained in Reference Example 5 was used and treated in a manner similar to Reference Example 6 to give the desired compound as light red oil.

NMR (CDCl$_3$, δ, ppm): 2.6–3.1 (m, 4H), 3.55 (s, 2H), 3.65 (s, 3H), 4.86 and 6.17 (ABq, J=13.1 Hz, 2H), 5.12 (s, 1H), 6.77 (d, J=8.4Hz, 1H), 6.95–7.40 (m, 7H)

REFERENCE EXAMPLE 16

Methyl 11-[2-(methylamino)ethyl]thio-6,11-dihydrodibenz-[b,e]oxepin-2-carboxylate (Compound p)

The corresponding starting material was used and treated in a manner similar to Reference Example 6 to give the desired compound.

NMR (CDCl$_3$, δ, ppm): 2.15 (bs, 3H), 2.38–2.78 (m, 4H), 3.86 (s, 3H), 4.86 and 6.42 (ABq, J=12.7Hz, 2H), 5.00 (s, 1H), 6.81 (d, J=8.5Hz, 1H), 7.20–7.39 (m, 4H), 7.75 (dd, J=2.2, 8.5Hz, 1H), 7.93 (d, J=2.2Hz, 1H)

REFERENCE EXAMPLE 17

Methyl 11-methoxy-6,11-dihydrodibenzo[b,e]thiepin-2-carboxolate.

(Compound q)

In 150 ml of methanol was suspended 50.0 g of p-bromothiophenol and, 14.9 g of sodium methoxide was added to the suspension. The mixture was stirred at 50° C. for an hour. The solvent was distilled off under reduced pressure and 35.5 g of phthalide was added to the residue followed by stirring at 180° C. for 3 hours. After cooling to room temperature, 200 ml of water was added to the reaction mixture, and dissolution was carried out by heating. After allowing to cool, pH was adjusted to 1.5 with conc. hydrochloric acid. The crystallized crude product was taken out by filtration. After drying, the crystals were recrystallized from toluene to give 56.3 g of 2-[(4-bromophenyl)thio]methylbenzoic acid.

Melting point:139°–140° C.

The compound described above, 12.0 g, was stirred at 90° C. for 10 hours, together with 120.0 g of polyphosphoric acid. The reaction solution was poured into 1 liter of ice. The mixture was stirred for further an hour and the crystallized crude product was taken out by filtration. After drying, the crystals were recrystallized from toluene to give 9.0 g of 2-bromo-11-oxo-6,11-dihydrodibenzo[b,e]thiepine.

Melting point:151°–152° C.

The aforesaid compound, 20.0 g, was suspended in a solvent mixture of 500 ml of methanol and 300 ml of tetrahydrofuran and, 4.5 g of sodium borohydride was added to the suspension followed by stirring at room temperature for an hour. The solvent was distilled off under reduced pressure and the resulting residue was recrystallized from methanol to give 12.0 g of 2-bromo-11-hydroxy-6,11-dihydrodibenzo[b,e]thiepine.

Melting point:169°–170° C.

The aforesaid compound, 8.6 g, was suspended in 180 ml of methanol and, 0.5 g of p-toluenesulfonic acid was added to the suspension. The mixture was heated for an hour under reflux. The solvent was distilled off under reduced pressure and the residue was extracted with 200 ml of ethyl acetate. The extract was washed in sequence with saturated sodium chloride aqueous solution and then with saturated sodium bicarbonate aqueous solution. After drying over anhydrous sodium sulfate, the solvent was distilled off under reduced pressure, and the obtained crude product was recrystallized from hexane to give 7.8 g of 2-bromo-11-methoxy-6,11-dihydrodibenzo[b,e]thiepine.

Melting point:68°–71° C.

The aforesaid compound, 19.0 g, and 8.0 g of cuprous cyanide were heated in 100 ml of dimethylformamide for 8 hours under reflux. After allowing to cool, 25 ml of ethylenediamine was added to the mixture. The mixture was stirred at 60° C. for 30 minutes and 100 ml of water was further added thereto followed by stirring at 60° C. for 30 minutes. After allowing to cool, the reaction mixture was extracted with 500 ml of ethyl acetate Insoluble matters were filtered off followed by washing 3 times with saturated sodium chloride aqueous solution. After drying over anhydrous sodium sulfate, the solvent was distilled off under reduced pressure. The resulting residue was subjected to silica gel column chromatography (eluting solvent; hexane:ethyl acetate=1:1). Further recrystallization from ethanol gave 11.3 g of 11-methoxy-2-cyano-6,11-dihydrodibenzo[b,e]thiepine.

Melting point:117°–118° C.

The aforesaid compound, 7.3 g, was heated in a solvent mixture of 300 ml of conc. hydrochloric acid and 200 ml of acetic acid under reflux for 8 hours. The solvent was distilled off under reduced pressure and 200 ml of methanol and 0.5 g of p-toluenesulfonic acid were added to the resulting residue. The mixture was heated under reflux for 3 hours. After allowing to cool, the solvent was distilled off under reduced pressure The resulting residue was extracted with 500 ml of ethyl acetate. The extract was washed in sequence with saturated sodium chloride aqueous solution and then with saturated sodium bicarbonate aqueous solution. After drying over anhydrous sodium sulfate, the solvent was distilled off under reduced pressure. The resulting residue was subjected to silica gel column chromatography (eluting solvent; hexane:ethyl acetate =5:1) to give 4.5 g of the light yellow amorphous desired compound.

IR (CHCl$_3$, cm$^{-1}$): 2994, 2952, 1715, 1437, 1301, 1120

REFERENCE EXAMPLE 18

Methyl 11-(2-aminoethyl)thio-6,11-dihydrodibenzo[b,e]-thiepin-2-carboxylate (Compound r)

Compound q obtained in Reference Example 17 was used and treated in a manner similar to Reference Example 6 to give the colorless amorphous desired compound.

IR (CHCl$_3$, cm$^{-1}$): 2998, 1715, 1596, 1299, 1275, 1122

REFERENCE EXAMPLE 19

Methyl 5-(2-aminoethyl)thio-10,11-dihydro-5H-dibenz-[a,d]-cyclohepten-3-carboxylate (Compound s)

In 1.0 liter of tetrahydrofuran was suspended 60 g of (2-methoxycarbonylbenzyl)triphenylphosphonium bromide and, 3.2 g of sodium hydride was added to the suspension followed by stirring at room temperature for 3 hours. Then, 18 g of 4-bromobenzaldehyde was added and the mixture was stirred at room temperature for 2 hours. After completion of the reaction, 500 ml of water, 200 ml of methanol and 100 ml of 0.1N hydrochloric acid aqueous solution were added thereto and the solvent was distilled off under reduced pressure. The residue was extracted with 500 ml of ethyl acetate. After washing in sequence with saturated sodium bicarbonate aqueous solution and then with saturated sodium chloride aqueous solution, the extract was dried over anhydrous magnesium sulfate and the solvent was distilled off under reduced pressure The resulting residue was recrystallized from methanol to give 17 g of methyl 2-(4-bromostyryl)benzoate as white needles.

Melting point:104°-106° C.

The aforesaid compound, 23 g, was dissolved in a solvent mixture of 470 ml of ethanol and 160 ml of acetic acid, 0.39 g of platinum dioxide was suspended therein. The suspension was stirred at 50° C. for 4 hours under hydrogen atmosphere. After completion of the reaction, the reaction solution was filtered through Celite and the solvent was distilled off under reduced pressure to give 24 g of light yellow amorphous methyl [2-(4-bromophenyl)ethyl]benzoate.

NMR (CDCl$_3$, δ, ppm): 2.7-3.0 (m, 2H), 3.1-3.4 (m, 2H), 3.84 (s, 3H), 6.9-7.4 (m, 7H), 7.86 (dd, 1H)

The aforesaid compound, 24 g, was dissolved in 490 ml of isopropanol, 160 ml of water and 160 ml of dioxane and, 19 ml of 10N sodium hydroxide aqueous solution was added to the solution followed by stirring at 70° C. for an hour. After allowing to cool, pH was adjusted to 7.0 with 4N hydrochloric acid aqueous solution. The solvent was distilled off under reduced pressure, and the aqueous layer was extracted with 200 ml of ethyl acetate. After washing with saturated sodium chloride aqueous solution, the extract was dried over anhydrous magnesium sulfate. The solvent was distilled off under reduced pressure to give 23 g of [2-(4-bromophenyl)ethyl]benzoic acid as white crystals.

Melting point:103°-107° C. acetate=

A mixture of 27 g of the aforesaid compound, 270 g of polyphosphoric acid and 130 ml of sulfolane was stirred at 160° C. for 2 hours. The reaction solution was poured into 500 ml of ice water and extracted with 500 ml of ethyl acetate. After washing in sequence with saturated sodium bicarbonate aqueous solution and then with saturated sodium chloride aqueous solution, the extract was dried over anhydrous magnesium sulfate. The solvent was distilled off under reduced pressure. The residue was subjected to silica gel column chromatography (eluting solvent; hexane:ethyl acetate =4:1) to give 9.6 g of brown amorphous 3-bromo-5-oxo-10,11-dihydro-5H-dibenzo[a,d]cycloheptane.

NMR (CDCl$_3$, δ, ppm): 3.15 (s, 4H), 7.0-7.6 (m, 5H), 7.9-8.1 (m, 1H), 8.10 (d, 1H)

The aforesaid compound, 9.0 g, and 5.6 g of cuprous cyanide were heated under reflux for 6 hours in 90 ml of dimethylformamide. After cooling to 50° C., 42 ml of anhydrous ethylenediamine was added to the reaction mixture followed by stirring at 50° C. for 30 minutes. Water, 200 ml, was added to the mixture and extracted with 200 ml of ethyl acetate. After washing with saturated sodium chloride aqueous solution, the extract was dried over anhydrous magnesium sulfate. The solvent was distilled off under reduced pressure. The residue was subjected to silica gel column chromatography (eluting solvent; hexane:ethyl acetate=4:1) to give 3.8 g of 3-cyano-5-oxo-10,11-dihydro-5H-dibenzo[a,d]cycloheptane.

IR (CHCl$_3$, cm$^{-1}$): 2232, 1644

The aforesaid compound, 2.0 g, was heated under reflux for 16 hours in a solvent mixture of 12 ml of conc. hydrochloric acid and 20 ml of acetic acid. The solvent was distilled off under reduced pressure and 20 ml of methanol and 1.7 ml of 10N sodium hydroxide aqueous solution were added to the resulting residue. The mixture was heated under reflux for 30 minutes. After allowing to cool, pH was adjusted to 6.9 with 4N hydrochloric acid aqueous solution and the solvent was distilled off under reduced pressure The resulting residue was recrystallized from isopropanol to give 1.8 g of 5-oxo-10,11-dihydro-5H-dibenzo[a,d]cycloheptan-3-carboxylic acid as yellow crystals.

Melting point:211°-215° C.

To a solution of 4.5 g of the compound described above in 90 ml of methanol was added 5.0 ml of conc. sulfuric acid. The mixture was heated under reflux for 3 hours. After allowing to cool, the solvent was distilled off under reduced pressure and 100 ml of water wa added thereto. The mixture was extracted with 100 ml of ethyl acetate. After washing in sequence with saturated sodium bicarbonate aqueous solution and then with saturated sodium chloride aqueous solution, the extract was dried over anhydrous magnesium sulfate. The solvent was distilled off under reduced pressure to give 4.5 g of colorless amorphous methyl 5-oxo-10,11-dihydro-5H-dibenzo[a,d]cycloheptan-3-carboxylate.

NMR (CDCl$_3$, δ, ppm): 3.18 (s 4H) 3.90 (s. 3H), 7.1-7.6 (m, 4H), 7.9-8.2 (m, 2H), 8.61 (d, 1H)

IR (CHCl$_3$, cm$^{-1}$):1714, 1651

The compound described above was used and treated in a manner similar to Example 2 to give methyl 5-hydroxy-10,11-dihydro-5H-dibenzo[a,d]cyclohepten-3-carboxylate as colorless oil.

NMR (CDCl$_3$, δ, ppm): 2.82-2.93 (m, 1H), 3.02-3.42 (m, 4H), 3.85 (s, 3H), 5.96 (bs, 1H), 7.09-7.42 (m, 5H), 7.80 (dd, J=1.8, 7.9Hz, 1H), 8.12 (d, J=1.5 Hz, 1H)

The compound described above was used and treated in a manner similar to Reference Example 6 to give the desired compound as light yellow oil.

NMR (CDCl$_3$, δ, ppm): 1.27 (s, 2H), 2.59 (dd, 2H, J=5.4, 17.7Hz), 2.4-3.1 (m, 4H), 3.6-4.0 (m, 2H), 3.86 (s, 3H), 5.10 (s, 1H), 7.0-7.4 (m, 5H), 7.81 (dd, 1H, J=1.9, 7.8Hz), 7.92 (d, 1H, J=1.8Hz)

REFERENCE EXAMPLE 20

Methyl 5-(2-aminoethyl)thio-5H-dibenzo[a,d]cyclohepten-3-carboxylate (Compound t)

In 100 ml of carbon tetrachloride was dissolved 3.30 g of methyl 5-oxo-10,11-dihydro-5H-dibenzo[a,d]cyclohepten-3-carboxylate obtained in Reference Example 19, 1.21 g of N-bromosuccinimide and 10 mg of benzoyl peroxide were added to the solution. The mixture was heated under reflux for an hour. To the reaction mixture was added 1.21 g of N-bromosuccinimide. The mixture was heated under reflux for further an hour. After allowing to cool to room temperature, the reaction mixture was filtered and the solvent was distilled off under reduced pressure. The resulting residue was dissolved in 60 ml of dimethylformamide and 2.4 ml of 1,8-diazabicyclo[5.4.0]-7-undecene was added to the solution. The mixture was stirred at 80° C. for an hour. After allowing to cool to room temperature, 100 ml of water was added and the precipitated crystals were filtered to give 3.16 g of methyl 5-oxo-5H-dibenz-[a,d]cyclohepten-3-carboxylate as white crystals.

Melting point:118°–120° C.

NMR (CDCl$_3$, δ, ppm): 3.96 (s, 3H), 7.09 (s, 1H), 7.11 (s, 1H), 7.5–7.7 (m, 4H), 8.1–8.3 (m, 2H), 8.85 (d, 1H, J=17Hz)

The compound described above was used and treated in a manner similar to Reference Example 2 to give methyl 5-hydroxy-5H-dibenz-[a,d]cyclohepten-3-carboxylate as colorless oil.

NMR (CDCl$_3$, δ, ppm): 2.76–2.93 (m, 1H), 3.86 (s, 3H), 5.31 (s, 1H), 7.05 (s, 1H), 7.08 (s, 1H), 7.15–7.48 (m, 4H), 7.67 (d, J=7.0Hz, 1H), 7.84 (dd, J=1.8, 7.9Hz, 1H), 8.31 (d, J=1.5Hz, 1H)

The compound described above was used and treated in a manner similar to Reference Example 6 to give the desired compound as light yellow oil.

NMR (CDCl$_3$, δ, ppm): 1.25 (s, 2H), 2.1–2.8 (m, 4H), 3.87 (s, 3H), 5.20 (s, 1H), 6.97 (s, 2H), 7.0–7.5 (m, 5H), 7.8–8.0 (m, 2H)

REFERENCE EXAMPLE 21

Methyl 10-(2-aminoethyl)thio-4,10-dihydrothieno[3,2-c][1]benzoxepin-8-acetate (Compound u)

4,10-Dihydro-10-oxothieno[3,2-c][1]benzoxepin-8-acetic acid, 25.5 g, synthesized according to the method of D.E. Aultz, et al. [J. Med. Chem., 20, 456 (1977)] and 0.9 g of p-toluenesulfonic acid monohydrate were heated under reflux for 3 hours in 600 ml of methanol. The solvent was distilled off under reduced pressure and the resulting residue was extracted with 500 ml of ethyl acetate. After washing in sequence with saturated sodium bicarbonate aqueous solution and then with saturated sodium chloride aqueous solution, the extract was dried over anhydrous magnesium sulfate. The solvent was then distilled off under reduced pressure. The resulting residue was subjected to silica gel column chromatography (eluting solvent; hexane:ethyl acetate=3:1) to give 24.9 g of methyl 4,10-dihydro-10-oxothieno[3,2-c][1]benzoxepin-8-acetate as light yellow solids.

NMR (CDCl$_3$, δ, ppm): 3.59 (s, 2H), 3.62 (s, 3H), 5.12 (s, 2H), 6.91 (d, J=5.2Hz, 1H), 7.01 (d, J=8.3Hz, 1H), 7.36 (dd, J=2.4, 8.3Hz, 1H), 7.55 (d, J=5.2Hz, 1H), 7.95 (d, J=2.4Hz, 1H)

The compound described above was used and treated in a manner similar to Reference Example 2 to give methyl 10-hydroxy-4,10-dihydrothieno[3,2-c][1]benzoxepin-8-acetate as colorless syrup.

NMR (CDCl$_3$, δ, ppm): 3.48 (s, 2H), 3.56 (s, 3H), 5.02 (s, 2H), 5.86 (d, J=7.6Hz, 1H), 6.57 (d, J=4.8Hz, 1H), 6.95–7.4 (m, 4H)

The compound described above was used and treated in a manner similar to Reference Example 6 to give the desired compound as light yellow oil.

MS (m/Z):329 (M+)

EXAMPLE 1

Methyl 11-[2-[(phenylsulfonyl)amino]ethyl]thio-6,11-dihydrodibenz-[b,e]oxepin-2-carboxylate (Compound 1a)

In 100 ml of pyridine was dissolved 9.00 g of methyl 11-(2-aminoethyl)thio-6,11-dihydrodibenz-[b,e]oxepin-2-carboxylate (Compound f) obtained in Reference Example 6. Under ice cooling, 4.2 ml of benzenesulfonyl chloride was dropwise added to the solution and the mixture was stirred at room temperature overnight. Pieces of ice were added to the mixture. After stirring for further an hour, the solvent was distilled off under reduced pressure. The residue was extracted with 500 ml of ethyl acetate and the extract was washed in sequence with saturated sodium bicarbonate aqueous solution and then with saturated sodium chloride aqueous solution. After drying over anhydrous sodium sulfate, the solvent was distilled off under reduced pressure. The resulting residue was subjected to silica gel column chromatography (eluting solvent; hexane:ethyl acetate=7:3) to give 9.90 g of the desired compound.

In Examples 2 through 5 described below, the desired compound was prepared in a manner similar to Example 1, using the corresponding 11-(2-aminoethyl)thio-6,11-dihydrodibenz-[b,e]oxepine derivative (Compound l, m, n or o).

EXAMPLE 2

Methyl 11-[2-[(phenylsulfonyl)amino]ethyl]thio-6,11-dihydrodibenz-[b,e]oxepin-2-acetate (Compound 2a)

EXAMPLE 3

Methyl 11-[2-[(phenylsulfonyl)amino]ethyl]thio-6,11-dihydrodibenz-[b,e]oxepin-3-carboxylate (Compound 3a)

EXAMPLE 4

Methyl 11-[2-[(phenylsulfonyl)amino]ethyl]thio-6,11-dihydrodibenz-[b,e]oxepin-9-carboxylate (Compound 4a)

EXAMPLE 5

Methyl 9-bromo-11-[2-[(phenylsulfonyl)amino]ethyl]thio-6,11-dihydrodibenz-[b,e]oxepin-2-carboxylate (Compound 6a):

In Examples 6 through 20 described below, the objective compound was prepared in a manner similar to Example 1 except that benzenesulfonyl chloride in Example 1 was changed to the corresponding sulfonyl chloride compound.

EXAMPLE 6

EXAMPLE 6

Methyl 11-[2-[(2-nitrophenylsulfonyl)amino]ethyl]thio-6,11-dihydrodibenz[b,e]oxepin-2-acetate (Compound 7a)

EXAMPLE 7

Methyl 11-[2-[(3-nitrophenylsulfonyl)amino]ethyl]thio-6,11-dihydrodibenz-[b,e]oxepin-2-acetate (Compound 8a)

EXAMPLE 8

Methyl 11-[2-[(4-nitrophenylsulfonyl)amino]ethyl]thio-6,11-dihydrodibenz-[b,e]oxepin-2-acetate (Compound 9a)

EXAMPLE 9

Methyl 11-[2-[(4-fluorophenylsulfonyl)amino]ethyl]thio-6,11-dihydrodibenz-[b,e]oxepin-2-acetate (Compound 10a)

EXAMPLE 10

Methyl 11-[2-[(4-chlorophenylsulfonyl)amino]ethyl]thio-6,11-dihydrodibenz-[b,e]oxepin-2-acetate (Compound 11a)

EXAMPLE 11

Methyl 11-[2-[(4-methylphenylsulfonyl)amino]ethyl]thio-6,11-dihydrodibenz-[b,e]oxepin-2-acetate (Compound 12a)

EXAMPLE 12

Methyl 11-[2-[(4-methoxyphenylsulfonyl)amino]ethyl]thio-6,11-dihydrodibenz-[b,e]oxepin-2-acetate (Compound 13a)

EXAMPLE 13

Methyl 11-[2-[(2-naphthylsulfonyl)amino]ethyl]thio-6,11-dihydrodibenz-[b,e]oxepin-2-acetate (Compound 14a)

EXAMPLE 14

Methyl 11-[2-[(2-thienylsulfonyl)amino]ethyl]thio-6,11-dihydrodibenz-[b,e]oxepin-2-acetate (Compound 15a)

EXAMPLE 15

Methyl 11-[2-[(8-quinolylsulfonyl)amino]ethyl]thio-6,11-dihydrodibenz-[b,e]oxepin-2-acetate (Compound 16a)

EXAMPLE 16

Methyl 11-[2-[(3-pyridylsulfonyl)amino]ethyl]thio-6,11-dihydrodibenz-[b,e]oxepin-2-acetate (Compound 17a)

EXAMPLE 17

Methyl 11-[2-[(styrylsulfonyl)amino]ethyl]thio-6,11-dihydrodibenz-[b,e]oxepin-2-acetate (Compound 18a)

EXAMPLE 18

Methyl 11-[2-[(2,5-dimethoxysulfonyl)amino]ethyl]thio-6,11-dihydrodibenz-[b,e]oxepin-2-acetate (Compound 20a)

EXAMPLE 19

Methyl 11-[2-[(3,4-dimethoxysulfonyl)amino]ethyl]thio-6,11-dihydrodibenz-[b,e]oxepin-2-acetate (Compound 21a)

EXAMPLE 20

Methyl 11-[2-[(4-trifluoromethylphenylsulfonyl)amino]ethyl]-thio-6,11-dihydrodibenz-[b,e]oxepin-2-acetate (Compound 23a)

Physicochemical properties of the compounds obtained in Examples 1 through 20 are shown in Table 6-1.

In Tables 6-1 through 6-11, * at the shoulder of solvent for recrystallization means solidification by trituration.

TABLE 6-1

| Example No. (Compound No.) | Appearance | mp (°C.) [solvent for recrystallization] | NMR (solvent) δ, ppm | IR (method) cm$^{-1}$ | MS m/z | Elemental Analysis (%) upper column: found lower column: calcd. | | |
|---|---|---|---|---|---|---|---|---|
| 1 (1a) | Colorless oil | — | (CDCl$_3$) 2.28–2.71 (m,2H), 2.73–3.12 (m,2H), 3.81 (s,3H), 4.88 (s,1H), 5.28 (t,J = 6.3 Hz,1H), 4.79 and 6.28 (ABq,J = 12.5 Hz,2H) 6.67–8.03 (m,12H) | (CHCl$_3$) 3275, 1710, 1612, 1324, 1162, 1118 | — | | | |
| 2 (2a) | Pale yellow amorphous | — | (CDCl$_3$) 2.31–2.74 (m,2H), 2.72–3.14 (m,2H), 3.49 (s,2H), 3.65 (s,3H), 4.76 and 6.11 (ABq,J = 13.3 Hz,2H), 5.04–5.45 (m,1H), 6.65–7.96 (m,12H) | (CHCl$_3$) 3280, 1732, 1328, 1161, 585 | — | | | |
| 3 (3a) | Yellow amorphous | — | (CDCl$_3$) 2.33–2.75 (m,2H), 2.76–3.20 (m,2H), 3.80 (s,3H), 4.79 and 6.10 (ABq,J = 12.7 Hz,2H), 5.44 (m,1H), 6.92–7.99 (m,12H) | (CHCl$_3$) 3250, 1719, 1615, 1322, 1297, 1161, 1097 | — | | | |
| 4 (4a) | Colorless oil | — | (CDCl$_3$) 2.29–2.68 (m,2H), 2.76–3.16 (m,2H), 3.85 (s,3H), 4.86 and 6.07 (ABq,J = 13.6 Hz,2H), 4.91 (s,1H), 5.21 (t,J = 5.4 Hz, 1H), 6.65–8.08 (m,12H) | (neat) 3496, 3296, 1719, 1157, 1013 | 469 (M$^+$) | | | |
| 5 (6a) | Colorless oil | — | (CDCl$_3$) 2.36–2.70 (m,2H), 2.80–3.21 (m,2H), 3.82 (s,3H), 4.78 and 6.21 (ABq,J = 12.9 Hz,2H), 4.82 (s,1H), 5.25 (t, J = 6.2 Hz, 1H), 6.67–8.07 (m,11H) | (neat) 1705, 1609, 1313, 1157 | — | | | |
| 6 (7a) | Colorless amorphous | Unclear [ether]* | (CDCl$_3$) 2.32–2.78 (m,2H), 2.83–3.36 (m,2H), 3.81 (s,3H), 4.87 and 6.26 (ABq,J = 13.2 Hz,2H), 5.18 (s,1H), 6.78 (d,J = 9.0 Hz, 1H), 7.13–7.42 (m,4H), 7.53–8.13 (m,6H) | (KBr tablet) 3312, 1719, 1612, 1531, 1323, 1250, 1168, 1119 | 514 (M$^+$) | | | |
| 7 (8a) | Pale yellow oil | — | (CDCl$_3$) 2.41–2.79 (m,2H), 2.83–3.23 (m,2H), 3.85 (s,3H), 4.85 and 6.29 (ABq,J = 12.8 Hz,2H), 5.47–5.83 (m,1H), 6.81 (d,J = 8.5 Hz,1H), 7.10–8.70 (m,10H) | (KBr tablet) 1710, 1610, 1533, 1353, 1250, 1163, 1127 | 514 (M$^+$) | | | |
| 8 (9a) | Light yellow crystal | 144.5–145.5 [isopropanol] | (CDCl$_3$ + DMSO-d$_6$) 2.30–2.71 (m,2H), 2.70–3.15 (m,2H), 3.84 (s,3H), 4.84 and 6.30 (ABq,J = 13.3 Hz,2H), 5.02 (s,1H), 6.78 (d,J = 8.5 Hz,1H), 7.00–8.45 (m, 10H) | (KBr tablet) 3260, 1712, 1611, 1524, 1351, 1242, 1159 | — | | | |
| 9 (10a) | Colorless oil | — | (CDCl$_3$) 2.38–2.71 (m,2H), 2.80–3.12 (m,2H), 3.83 (s,3H), 4.83 and 6.28 (ABq,J = 12.9 Hz,2H), 4.94 (s,1H), 5.29 (t,J = 6.5 Hz,1H), 6.72–7.99 (m,11H) | (neat) 3278, 1716, 1609, 1329, 1229 | — | | | |
| 10 (11a) | White solid [isopropyl ether] | 133.5–134 | (CDCl$_3$) 2.3–2.71 (m,2H), 2.76–3.14 (m,2H), 3.82 (s,3H), 4.81 and 6.24 (ABq,J = 12.2 Hz,2H), 4.91 (s,1H), 5.27 (t,J = 5.9 Hz, 1H), 6.77 (d,J = 8.6 Hz,1H), 6.97–7.95 (m,10H) | (KBr tablet) 3296, 1716, 1332, 1251, 1159, 1119, 1003 | 504 (M$^+$) | C$_{24}$H$_{22}$ClNO$_5$S$_2$ | | |
| | | | | | | C | H | N |
| | | | | | | 57.10 | 4.55 | 2.86 |
| | | | | | | 57.19 | 4.40 | 2.78 |
| 11 (12a) | White solid [isopropyl ether]* | 127–128 | (CDCl$_3$) 2.39 (s,3H), 2.26–2.27 (m,2H), 2.76–3.21 (m,2H) 3.84 (s,3H), 4.83 and 6.30 (ABq,J = 12.7 Hz,2H), 4.91 (s,1H) 5.18 (t,J = 6.5 Hz,1H), 6.80 (d, J = 8.0 Hz,1H), 6.93–7.97 (m,10H) | (KBr tablet) 3292, 1714, 1609, 1326, 1250, 1156, 1119, 1005 | 483 (M$^+$) | C$_{25}$H$_{25}$NO$_5$S$_2$ | | |
| | | | | | | C | H | N |
| | | | | | | 62.01 | 5.35 | 3.10 |
| | | | | | | 62.09 | 5.21 | 2.90 |
| 12 (13a) | White solid [toluene] | 132–133 | (CDCl$_3$) 2.34–2.75 (m,2H), 2.75–3.17 (m,2H), 3.82 (s,3H) 3.86 (s,3H), 4.84 and 6.32 (ABq, J = 13.3 Hz,2H), 4.94 (s,1H), 4.93–5.25 (m,1H), 6.73–7.99 (m,11H) | (KBr tablet) 3272, 1707, 1498, 1327, 1253, 1155, 1120, 1010 | 499 (M$^+$) | C$_{25}$H$_{25}$NO$_6$S$_2$ | | |
| | | | | | | C | H | N |
| | | | | | | 60.15 | 5.30 | 2.55 |
| | | | | | | 60.10 | 5.04 | 2.80 |
| 13 (14a) | Colorless amorphous | — | (CDCl$_3$) 2.30–2.71 (m,2H), 2.71–3.22 (m,2H), 3.78 (s,3H), 4.73 and 6.2 (ABq,J = 12.9 Hz,2H), 4.87 (s,1H), 5.46 (t,J = 6.3 Hz,1H), 6.72 (d,J = 8.0 Hz,1H), 6.80–8.03 (m,12H), 8.32 (bs,1H) | (KBr tablet) 3258, 1715, 1610, 1435, 1324, 1244, 1156, 1131, 1007 | 487 (M$^+$) | | | |
| 14 (15a) | White crystal [isopropyl ether] | 115–116 | (CDCl$_3$) 2.38–2.74 (m,2H), 2.84–3.30 (m,2H), 3.86 (s,3H), 4.85 and 6.32 (ABq,J = 12.1 Hz,2H) 4.95 (s,1H), 5.29 (t,J = 6.2 Hz, 1H), 6.71–8.03 (m,10H) | (KBr tablet) 3270, 1717, 1611, 1330, 1295, 1249, 1149, 1008 | — | C$_{22}$H$_{21}$NO$_5$S$_3$ | | |
| | | | | | | C | H | N |
| | | | | | | 55.49 | 4.50 | 3.00 |
| | | | | | | 55.56 | 4.45 | 2.95 |

TABLE 6-1-continued

| Example No. (Compound No.) | Appearance | mp (°C.) [solvent for recrystallization] | NMR (solvent) δ, ppm | IR (method) cm$^{-1}$ | MS m/z | Elemental Analysis (%) upper column: found lower column: calcd. |
|---|---|---|---|---|---|---|
| 15 (16a) | White crystal | 135–136 [ethyl acetate] | (CDCl$_3$) 2.37–2.75 (m,2H), 2.82–3.19 (m,2H), 3.94 (s,3H), 4.81 and 6.33 (ABq,J = 13.4 Hz, 2H), 4.97 (s,1H), 6.65–9.27 (m,13H) | (KBr tablet) 3252, 1704, 1328, 1251, 1163, 1006 | 520 (M$^+$) | C$_{27}$H$_{24}$N$_2$O$_5$S$_2$<br>C   H   N<br>62.00  4.78  5.18<br>62.29  4.65  5.38 |
| 16 (17a) | White amorphous | — | (CDCl$_3$) 2.4–3.8 (m,4H), 3.88 (s,3H), 4.89 and 6.36 (ABq,J = 13.0 Hz,2H), 5.05 (s,1H), 6.83 (d,J = 8.6 Hz,1H), 7.2–8.3 (m,10H) | KBr tablet) 3068, 1713, 1610, 1327, 1257, 1165, 1111, 1011 | 470 (M$^+$) | — |
| 17 (18a) | Colorless oil | — | (CDCl$_3$) 2.50–2.90 (m,2H), 2.95–3.39 (m,2H), 3.85 (s,3H), 4.88 and 6.37 (ABq,J = 12.8 Hz,2H), 5.05 (s,1H), 5.13 (t,J = 7.4 Hz, 1H), 6.70 (d,J = 8.6 Hz,1H), 6.86–7.66 (m,11H), 7.78 (dd,J = 2.4, 8.6 Hz,1H), 7.98 (d,J = 2.4 Hz, 1H) | (KBr tablet) 3256, 1704, 1610, 1434, 1322, 1244, 1143 | 495 (M$^+$) | — |
| 18 (20a) | Colorless oil | — | (CDCl$_3$) 2.30–2.71 (m,2H), 2.80–3.22 (m,2H), 3.82 (s,3H), 3.89 (s,6H), 4.84 and 6.31 (ABq,J = 12.4 Hz,2H), 4.94 (s,1H), 5.45 (t,J = 6.1 Hz,1H), 6.81 (d,J = 8.4 Hz,1H), 6.99–7.48 (m,8H), 7.65–7.98 (m,2H) | (KBr tablet) 2836, 1714, 1610, 1496, 1325, 1275, 1244, 1156, 1007 | 529 (M$^+$) | — |
| 19 (21a) | White solid | 153–154 [toluene] | (CDCl$_3$) 2.26–3.16 (m,4H), 3.82 (s,3H), 3.84 (s,3H), 3.86 (s, 3H), 4.90 and 6.31 (ABq,J = 11.9 Hz,2H), 5.25 (s,1H), 6.82 (d,J = 8.5 Hz,1H), 6.99–7.56 (m, 7H), 7.73 (dd,J = 1.9,8.5 Hz,1H), 7.99 (d,J = 1.9 Hz,1H) | (KBr tablet) 3240, 1714, 1610, 1574, 1325, 1296, 1275, 1244, 1156, 1131, 1007 | 529 (M$^+$) | C$_{26}$H$_{27}$NO$_7$S$_2$<br>C   H   N<br>58.81  5.40  2.50<br>58.96  5.14  2.64 |
| 20 (23a) | Colorless oil | — | (CDCl$_3$) 2.39–2.83 (m,2H), 2.84–3.25 (m,2H), 3.86 (s,3H), 4.84 and 6.30 (ABq,J = 12.8 Hz, 2H), 4.97 (s,1H), 5.59 (t,J = 6.0 Hz,1H), 6.82 (d,J = 8.6 Hz, 1H), 7.58–8.25 (m,10H) | — | 537 (M$^+$) | — |

EXAMPLE 21

11-[2-[(Phenylsulfonyl)amino]ethyl]thio-6,11-(dihydrodibenz-[b,e]oxepin-2-carboxylic acid (Compound 1b)

Compound 1a, 9.90 g, obtained in Example 1 was dissolved in a solvent mixture of 200 ml of methanol and 20 ml of water and 2.70 g of sodium hydroxide was added to the solution. The mixture was heated under reflux for 2 hours. The solvent was distilled off under reduced pressure and the resulting residue was dissolved in 200 ml of water. A pH was adjusted to 1.5 with 4N hydrochloric acid aqueous solution. The crystallized crude product was taken out by filtration and dried. The crude product was recrystallized from 300 ml of isopropanol to give 6.44 g of the desired compound.

In Examples 22 through 40 described below, the desired compound was obtained in a manner similar to Example 21, by hydrolyzing an ester of the corresponding oxepine derivative.

EXAMPLE 22

11-[2-[(Phenylsulfonyl)amino]ethyl]thio-6,11-dihydrodibenz-[b,e]oxepin-2-acetic acid (Compound 2b)

EXAMPLE 23

11-[2-[(Phenylsulfonyl)amino]ethyl]thio-6,11-dihydrodibenz-[b,e]oxepin-3-carboxylic acid (Compound 3b)

EXAMPLE 24

11-[2-[(Phenylsulfonyl)amino]ethyl]thio-6,11-dihydrodibenz-[b,e]oxepin-9-carboxylic acid (Compound 4b)

EXAMPLE 25

9-Bromo-11-[2-[(phenylsulfonyl)amino]ethyl]thio-6,11-dihydrodibenz-[b,e]oxepin-2-carboxylic acid (Compound 6b)

EXAMPLE 26

11-[2-[(2-Nitrophenylsulfonyl)amino]ethyl]thio-6,11-dihydrodibenz-[b,e]oxepin-2-carboxylic acid.0.2 hydrate (Compound 7b′)

EXAMPLE 27

11-2-{3-Nitrophenylsulfonyl)amino]ethyl]thio-6,11-dihydrodibenz-[b,e]oxepin-2-carboxylic acid.0.5 isopropanol.0.5 hydrate (Compound 8b′)

EXAMPLE 28

11-[2-[(4-Nitrophenylsulfonyl)amino]ethyl]thio-6,11-dihydrodibenz-[b,e]oxepin-2-carboxylic acid (Compound 9b)

EXAMPLE 29

11-[2-[(4-Fluorophenylsulfonyl)amino]ethyl]thio-6,11-dihydrodibenz-[b,e]oxepin-2-carboxylic acid (Compound 10b)

EXAMPLE 30

11-[2-[(4-Chlorophenylsulfonyl)amino]ethyl]thio-6,11-dihydrodibenz-[b,e]oxepin-2-carboxylic acid (Compound 11b)

EXAMPLE 31

11-[2-[(4-Methylphenylsulfonyl)amino]ethyl]thio-6,11-dihydrodibenz-[b,e]oxepin-2-carboxylic acid (Compound 12b)

EXAMPLE 32

11-[2-[(4-Methoxyphenylsulfonyl)amino]ethyl]thio-6,11-dihydrodibenz-[b,e]oxepin-2-carboxylic acid (Compound 13b)

EXAMPLE 33

11-[2-[(2-Naphthylsulfonyl)amino]ethyl]thio-6,11-dihydrodibenz-[b,e]oxepin-2-carboxylic acid.0.3 hydrate (Compound 14b′)

EXAMPLE 34

11-[2-[(2-Thienylsulfonyl)amino]ethyl]thio-6,11-dihydrodibenz[b,e]oxepin-2-carboxylic acid (Compound 15b)

EXAMPLE 35

11-[2-[(8-Quinolylsulfonyl)amino]ethyl]thio-6,11-dihydrodibenz-[b,e]oxepin-2-carboxylic acid (Compound 16b)

EXAMPLE 36

11-[2-[(3-Pyridylsulfonyl)amino]ethyl]thio-6,11-dihydrodibenz-[b,e]oxepin-2-carboxylic acid.monohydrate (Compound 17b′)

EXAMPLE 37

11-[2-[(Styrylsulfonyl)amino]ethyl]thio-6,11-dihydrodibenz-[b,e]oxepin-2-carboxylic acid 0.2 hydrate (Compound 18b′)

EXAMPLE 38

11-[2-[(2,5-Dimethoxyphenylsulfonyl)amino]ethyl]thio-6,11-dihydrodibenz-[b,e]oxepin-2-carboxylic acid (Compound 20b)

EXAMPLE 39

11-[2-[(3,4-Dimethoxyphenylsulfonyl)amino]ethyl]thio-6,11 -dihydrodibenz-[b,e]oxepin-2-carboxylic acid 0.2 hydrate (Compound 21b′)

EXAMPLE 40

11-[2-[(4-Trifluoromethylphenylsulfonyl)amino]ethyl]thio-6,11-dihydrodibenz-[b,e]oxepin-2-carboxylic acid (Compound 23b)

EXAMPLE 41

Sodium 11-[2-[(phenylsulfonyl)amino]ethyl]thio-6,11-dihydrobenzo[b,e]oxepin-2-carboxylate monohydrate (Compound 1b′)

Compound 1b, 3.3 g, obtained in Example 21 was suspended in 100 ml of methanol and sodium methoxide was added to the solution followed by stirring for about an hour. The solvent was distilled off under reduced pressure and the resulting crude product was solidified by isopropyl ether to give 2.3 g of the desired compound.

EXAMPLE 42

Sodium 11-[2-[(phenylsulfonyl)amino]ethyl]thio-6,11-dihydrodibenz-[b,e]oxepin-2-acetate (Compound 2b')

The desired compound was prepared in a manner similar to Example 41, using Compound 2b obtained in Example 22.

Physicochemical properties of the compounds obtained in Examples 21 through 42 are shown in Table 6-2.

TABLE 6-2

| Example No. (Compound No.) | Appearance | mp (°C.) [solvent for recrystallization] | NMR (solvent) δ, ppm | IR (method) cm$^{-1}$ | MS m/z | Elemental Analysis (%) upper column: found lower column: calcd. |
|---|---|---|---|---|---|---|
| 21 (1b) | White crystal | 184–186 [isopropanol] | (DMSO-$d_6$) 2.46–2.51 (m, 2H), 2.71–2.94 (m, 2H), 5.42 (s, 1H), 5.02 and 6.20 (ABq, J=12.8Hz, 2H), 6.84–7.98 (m, 12H), 12.76 (bs, 1H) | (KBr tablet) 3274, 1680, 1610, 1324, 1243, 1158 | — | $C_{23}H_{21}NO_5S_2$<br>C  H  N<br>60.65  4.62  2.99<br>60.64  4.65  3.07 |
| 22 (2b) | Colorless oil | — | (DMSO-$d_6$) 2.42–2.51 (m, 2H), 2.58–2.87 (m, 2H), 3.13 (s, 1H), 4.83 and 6.04 (ABq, J=13.0Hz, 2H), 5.19 (s, 1H), 6.61–7.82 m, 12H) | — | 469 ($M^+$) | — |
| 23 (3b) | Yellow amorphous | 85 (unclear) [isopropyl ether] | (DMSO-$d_6$) 2.46–2.52 (m, 2H), 2.81–2.92 (m, 2H), 4.98 and 6.03 (ABq, J=12.9Hz, 2H), 5.33 (s, 1H), 7.31–7.87 (m, 12H), 12.89 (bs, 1H) | (KBr tablet) 1685, 1566, 1423, 1322, 1156, 1092, 1028, 751 | — | $C_{28}H_{21}NO_5S_2 \cdot 0.2C_6H_{14}O$<br>C  H  N<br>60.87  5.00  2.61<br>61.07  5.04  2.94 |
| 24 (4b) | White crystal | 156–160 [toluene] | (DMSO-$d_6$) 2.45–2.55 (m, 2H), 2.75–2.90 (m, 2H), 4.99 and 6.07 (ABq, J=13.4Hz, 1H), 5.32 (s, 1H), 6.84 (d, J=8.1Hz, 1H), 6.95 (t, J=7.3Hz, 1H), 7.15–7.35 (m, 2H), 7.48 (d, J=7.7Hz, 1H), 7.6–7.95 (m, 8H) | (KBr tablet) 3450, 3275, 1693, 1310, 1154, 753 | 455 ($M^+$) | $C_{23}H_{21}NO_5S_2$<br>C  H  N<br>60.97  4.56  2.74<br>60.64  4.65  3.07 |
| 25 (6b) | White crystal | 183–185 [toluene] | (DMSO-$d_6$) 2.30–2.58 (m, 2H), 2.80–2.94 (m, 2H), 5.04 and 6.13 (ABq, J=12.8Hz, 2H), 5.44 (s, 1H), 6.85–7.93 (m, 1H) | (KBr tablet) 3298, 1682, 1607, 1328, 1254, 1158 | — | $C_{23}H_{20}BrNO_5S_2$<br>C  H  N<br>51.78  3.64  2.58<br>51.69  3.77  2.62 |
| 26 (7b') | Light yellow crystal | 211–212.5 [isopropanol] | (DMSO-$d_6$) 2.5–2.6 (m, 2H), 2.85–3.20 (m, 2H), 5.01 and 6.19 (ABq, J=12.7Hz, 1H), 5.43 (s, 1H) 6.86 (d, J=8.5H, 1H), 7.3–7.45 (m, 4H), 7.71 (dd, J=2.2, 8.5Hz, 1H), 7.83–8.0 (m, 5H), 8.23 (t, J=5.6Hz, 1H), 12.75 (bs, 1H) | (KBr tablet) 3328, 1682, 1609, 1537, 1346, 1255, 1176 | 500 ($M^+$) | $C_{23}H_{20}N_2O_7S_2 \cdot 0.2H_2O$<br>C  H  N<br>54.74  3.68  5.35<br>54.80  4.08  5.56 |
| 27 (8b') | White crystal | 190–191 (decomposed) [isopropanol-isopropyl ether] | (DMSO-$d_6$) 2.45–2.6 (m, 2H), 2.75–3.05 (m, 2H), 4.98 and 6.16 (ABq, J=12.6Hz, 2H), 5.41 (s, 1H), 6.82 (d, J=8.6Hz, 1H), 7.3–7.45 (m, 4H), 7.68 (dd, J=2.2, 8.6Hz, 1H), 7.85–7.95 (m, 2H), 8.15–8.35 (m, 2H), 8.45–8.50 (m, 2H) | (KBr tablet) 3450, 1685, 1609, 1532, 1352, 1234, 1166 | 500 ($M^+$) | $C_{23}H_{20}N_2O_7S_2 \cdot 0.5C_3H_8O \cdot 0.5H_2O$<br>C  H  N<br>54.78  4.35  5.06<br>54.53  4.67  5.19 |
| 28 (9b) | White crystal | 235–237 [ethyl acetate] | (DMSO-$d_6$) 2.45–2.55 (m, 2H), 2.75–3.1 (m, 2H), 5.01 and 6.18 (ABq, J=12.7Hz, 2H), 5.43 (s, 1H), 6.85 (d, J=8.5Hz, 1H), 7.35–7.45 (m, 4H), 7.70 (dd, J=2.2, 8.5Hz, 1H), 7.97 (d, J=2.2Hz, 1H), 8.01 (d, J=9.0Hz, 2H), 8.24 (t, J=5.7Hz, 1H), 8.41 (d, J=9.0Hz, 2H), 12.7 (bs, 1H), | (KBr tablet) 3348, 1683, 1607, 1527, 1348, 1247, 1157 | 500 ($M^+$) | $C_{23}H_{20}N_2O_7S_2$<br>C  H  N<br>55.02  3.98  5.42<br>55.19  4.03  5.60 |
| 29 (10b) | White crystal | 100 (unclear) [isopropanol] | (DMSO-$d_6$) 2.43–2.52 (m, 2H), 2.71–2.96 (m, 2H), 4.91 and 6.10 (ABq, J=12.7Hz, 2H), 5.27 (s, 1H), 6.66–8.32 (m, 1H) | (KBr tablet) 1612, 1560, 1387 | — | $C_{23}H_{20}FNO_5S_2$<br>C  H  N<br>58.06  3.99  2.91<br>58.34  4.26  2.96 |
| 30 (11b) | White crystal | 188–189 [isopropanol] | (DMSO-$d_6$) 2.45–2.55 (m, 2H), 2.70–3.00 (m, 2H), 5.01 and 6.20 (ABq, J=12.7Hz, 2H), 5.42 (s, 1H) 6.86 (d, J=8.5H, 1H), 7.3–7.5 (m, 4H), 7.6–7.8 (m, 5H), 7.93 (t, J=5.6Hz, 1H), 7.98 (d, J=1.9 Hz, 1H) | (KBr tablet) 3300, 1679, 1609, 1427, 1233, 1155, 1091 | — | $C_{23}H_{20}ClNO_5S_2$<br>C  H  N<br>56.30  4.03  2.63<br>56.38  4.11  2.86 |
| 31 (12b) | White crystal | 181.5–182 [isopropanol] | (DMSO-$d_6$) 2.4–2.55 (m, 2H), 2.70–2.95 (m, 2H), 5.01 and 6.20 (ABq, J=12.7Hz, 2H), 5.40 (s, | (KBr tablet) 3256, 1680, 1610, 1323, | 469 ($M^+$) | $C_{24}H_{23}NO_5S_2$<br>C  H  N<br>61.19  4.90  2.77 |

TABLE 6-2-continued

| Example No. (Compound No.) | Appearance | mp (°C.) [solvent for recrystallization] | NMR (solvent) δ, ppm | IR (method) cm$^{-1}$ | MS m/z | Elemental Analysis (%) upper column: found lower column: calcd. |
|---|---|---|---|---|---|---|
| | | | 1H), 6.86 (d, J=8.5Hz, 1H), 7.3–7.5 (m, 6H), 7.6–7.8 (m, 4H), 7.97 (d, J=1.9Hz, 1H) | 1254, 1156 | | 61.39  4.94  2.98 |
| 32 (13b) | White crystal | 189–190 [acetonitrile] | (DMSO-d$_6$) 2.4–2.55 (m, 2H), 2.65–2.90 (m, 2H), 3.85 (s, 3H), 5.01 and 6.20 (ABq, J=12.8Hz, 2H), 5.41 (s, 1H), 6.86 (d, J=8.5 Hz, 1H), 7.10 (d, J=8.8Hz, 2H), 7.3–7.45 (m, 4H), 7.65–7.75 (m, 4H), 7.97 (d, J=1.9Hz, 1H) | (KBr tablet) 3284, 1679, 1599, 1324, 1254, 1152 | 485 (M$^+$) | C$_{24}$H$_{23}$NO$_6$S$_2$<br>C      H      N<br>59.07  4.63  2.57<br>59.37  4.77  2.88 |
| 33 (14b') | White crystal | 150 (decomposed) [isopropyl ether] | (DMSO-d$_6$) 2.4–2.6 (m, 2H), 2.7–3.0 (m, 2H), 4.93 and 6.13 (ABq, J=12.6Hz, 2H), 5.37 (s, 1H), 6.80 (d, J=8.6Hz, 1H), 7.15 7.35 (m, 4H), 6.5–7.8 (m, 4H), 7.95 (bs, 1H), 8.05–8.2 (m, 4H), 8.40 (bs, 1H) | (KBr tablet) 3450, 1684, 1608, 1322, 1155 | — | C$_{27}$H$_{23}$NO$_5$S$_2$·0.3H$_2$O<br>C      H      N<br>63.39  4.64  2.71<br>63.46  4.65  2.74 |
| 34 (15b) | White crystal | 100 (unclear) [isopropanol] | (DMSO-d$_6$) 2.49–2.54 (m, 2H), 2.84–2.99 (m, 2H), 5.02 and 6.21 (ABq, J=12.7Hz, 2H), 5.43 (s, 1H), 6.84–8.02 (m, 10H) | (KBr tablet) 3240, 1683, 1609, 1325, 1234, 1154 | — | C$_{21}$H$_{19}$NO$_5$S$_3$<br>C      H      N<br>54.52  3.81  2.96<br>54.65  4.15  3.03 |
| 35 (16b) | White crystal | 191–193 [isopropanol] | (DMSO-d$_6$) 2.41–2.51 (m, 2H), 2.85–2.96 (m, 2H), 4.89 and 6.03 (ABq, J=12.7Hz, 2H), 5.30 (s, 1H), 6.80–9.07 (m, 13H) | (KBr tablet) 3258, 1694, 1604, 1317, 1231 | 506 (M$^+$) | C$_{26}$H$_{22}$N$_2$O$_5$S$_2$<br>C      H      N<br>61.55  4.46  5.16<br>61.64  4.38  5.53 |
| 36 (17b') | White crystal | 172–174 [isopropanol-water] | (DMSO-d$_6$) 2.4–2.6 (m, 2H), 2.75–3.05 (m, 2H), 5.01 and 6.19 (ABq, J=12.8Hz, 2H), 5.44 (s, 1H), 6.86 (d, J=8.5Hz, 1H), 7.4–7.5 (m, 3H), 7.6–7.75 (m, 2H), 8.05–8.20 (m, 2H), 7.98 (bs, 1H), 8.83 (bs, 1H), 8.93 (bs, 1H) | (KBr tablet) 3450, 3278, 1699, 1610, 1322, 1251, 1165 | 442 (M$^+$) | C$_{22}$H$_{20}$N$_2$O$_5$S$_2$·H$_2$O<br>C      H      N<br>57.52  4.50  6.09<br>57.38  4.82  6.08 |
| 37 (18b') | White crystal | 176–178 [toluene] | (DMSO-d$_6$) 2.5–2.65 (m, 2H), 2.85–3.20 (m, 2H), 5.01 and 6.22 (ABq, J=12.7Hz, 2H), 5.45 (s, 1H), 6.86 (d, J=8.5Hz, 1H), 7.15 7.55 (m, 11H), 7.65–7.75 (m, 2H), 8.01 (d, J=1.8Hz, 1H), 12.75 (bs, 1H) | (KBr tablet) 3475, 1696, 1611, 1321, 1254, 1142 | — | C$_{25}$H$_{23}$NO$_5$S$_2$·0.2H$_2$O<br>C      H      N<br>61.93  4.76  2.86<br>61.89  4.86  2.89 |
| 38 (20b) | White crystal | 168–172 [isopropanol] | (DMSO-d$_6$) 2.4–2.55 (m, 2H), 2.75–3.05 (m, 2H), 3.76 (s, 3H), 3.80 (s, 3H), 5.00 and 6.17 (ABq, J=12.7Hz, 2H), 5.37 (s, 1H), 6.85 (d, J=8.6Hz, 1H), 7.15–7.45 (m, 8H), 7.70 (dd, J=2.0, 8.6Hz, 1H), 7.96 (d, J=2.0Hz, 1H) | (KBr tablet) 3450, 1674, 1609, 1496, 1324, 1235, 1158 | 515 (M$^+$) | C$_{25}$H$_{25}$NO$_7$S$_2$<br>C      H      N<br>58.23  4.95  2.44<br>58.24  4.89  2.72 |
| 39 (21b') | White crystal | 136–138 [acetonitrile] | (DMSO-d$_6$) 2.4–2.55 (m, 2H), 2.65–2.95 (m, 2H), 3.80 (s, 3H), 3.85 (s, 3H), 5.00 and 6.19 (ABq, J=12.7Hz, 2H), 5.40 (s, 1H), 6.85 (d, J=8.5Hz, 1H), 7.11 (d, J=8.5) Hz, 1H), 7.25–7.45 (m, 6H), 7.63 (t, J=5.7Hz, 1H), 7.70 (dd, J=2.0, 8.5Hz, 1H), 7.97 (d, J=2.0Hz, 1H) | (KBr tablet) 3450, 3270, 1700, 1508, 1314, 1263, 1237, 1138 | 515 (M$^+$) | C$_{25}$H$_{25}$NO$_7$S$_2$·0.2H$_2$O<br>C      H      N<br>57.77  4.91  2.48<br>57.83  4.93  2.70 |
| 40 (23b) | White crystal | 207–208 [toluene]* | (DMSO-d$_6$) 2.4–2.6 (m, 2H), 2.75–3.05 (m, 2H), 5.00 and 6.19 (ABq, J=12.7Hz, 2H), 5.43 (s, 1H), 6.85 (d, J=8.5Hz, 1H), 7.30–7.45 (m, 4H), 7.70 (dd, J=2.2, 8.5Hz, 1H), 7.95–8.05 (m, 5H), 8.12 (t, J=5.5 Hz, 1H) | (KBr tablet) 3450, 3280, 1684, 1608, 1323, 1161, 1131 | — | C$_{24}$H$_{20}$F$_3$NO$_5$S$_2$<br>C      H      N<br>55.20  3.99  2.50<br>55.06  3.85  2.68 |
| 41 (1b') | Pale yellow amorphous | Impossible to measure due to hygroscopic nature [isopropyl ether]* | — | — | — | C$_{23}$H$_{20}$NO$_5$S$_2$Na·H$_2$O<br>C      H      N<br>55.32  4.25  2.88<br>55.47  4.48  2.83 |
| 42 (2b') | Pale yellow amorphous | Impossible to measure due to hygroscopic nature [isopropyl ether]* | — | — | 491 (M$^+$) | C$_{24}$H$_{22}$NO$_5$S$_2$Na<br>C      H      N<br>58.40  4.57  2.56<br>58.64  4.51  2.85 |

EXAMPLE 43

Methyl N-methyl-11-[2-[(phenylsulfonyl)amino]ethyl]thio-6,11-dihydrodibenz-[b,e]oxepin-2-carboxylate (Compound 5a)

The desired compound was prepared in a manner similar to Example 1, using Compound p obtained in Reference Example 16.

EXAMPLE 44

N-Methyl-11-[2-[(phenylsulfonyl)amino]ethyl]thio-6,11-dihydrodibenz-[b,e]oxepin-2-carboxylic acid (Compound 5b)

The desired compound was prepared by hydrolyzing Compound 5a obtained in Reference Example 43 in a manner similar to Example 21.

Physicochemical properties of the compounds obtained in Examples 43 and 44 are shown in Table 6-3.

EXAMPLE 46

Methyl 11-[2-[(phenylsulfonyl)amino]propyl]amino-6,11-dihydrodibenz-[b,e]oxepin-2-carboxylate (Compound 25a)

The desired compound was prepared in a manner similar to Example 1, using Compound h obtained in Reference Example 8.

In Examples 47 and 48 described below, the desired compound was obtained by hydrolyzing an ester of the corresponding oxepine derivative in a manner similar to Example 21.

EXAMPLE 47

11-[2-[(Phenylsulfonyl)amino]ethyl]amino-6,11-dihydrodibenz-[b,e]oxepin-2-carboxylic acid.0.25 hydrate (Compound 24b')

EXAMPLE 48

11-[2-[(Phenylsulfonyl)amino]propyl]amino-6,11-dihydrodibenz-[b,e]oxepin-2-carboxylic acid.0.5 hydrate (Compound 25b')

TABLE 6-3

| Example No. (Compound No.) | Appearance | mp (°C.) [solvent for recrystallization] | NMR (solvent) δ, ppm | IR (method) cm$^{-1}$ | MS m/z | Elemental Analysis (%) upper column: found lower column: calcd. |
|---|---|---|---|---|---|---|
| 43 (5a) | Colorless oil | — | (CDCl$_3$) 2.68 (s, 3H), 2.27–3.39 (m, 4H), 3.85 (s, 3H), 4.88 and 6.39 (ABq, J=13.1Hz, 2H), 5.07 (s, 1H), 6.83 (d, J=8.5Hz, 1H), 7.14–8.06 (m, 11H) | (CHCl$_3$) 3066, 1712, 1611, 1342, 1244, 1163, 1119, 1007 | 483 (M$^+$) | — |
| 44 (5b) | White crystal | 180–181 [isopropanol] | (DMSO-d$_6$) 2.49–2.52 (m, 2H), 2.63 (s, 3H), 2.85–3.20 (m, 2H), 5.04 and 6.25 (ABq, J=12.8Hz, 2H), 5.49 (s, 1H), 6.87 (d, J=8.5Hz, 1H), 7.36–7.58 (m, 4H), 7.60–7.75 (m, 6H), 8.00 (d, J=2.2Hz, 1H), 12.73 (bs, 1H) | (KBr tablet) 3372, 1680, 1607, 1336, 1236, 1163, 996 | 469 (M$^+$) | C$_{24}$H$_{23}$NO$_5$S$_2$<br>C  H  N<br>61.00  4.94  2.90<br>61.39  4.94  2.98 |

EXAMPLE 45

Ethyl 11-[2-[(phenylsulfonyl)amino]ethyl]thio-6,11-dihydrodibenz-[b,e]oxepin-2-carboxylate (Compound 24a)

The desired compound was prepared in a manner similar to Example 1, using Compound g obtained in Reference Example 7.

Physicochemical properties of the compounds obtained in Examples 45 through 48 are shown in Table 6-4.

TABLE 6-4

| Example No. (Compound No.) | Appearance | mp (°C.) [solvent for recrystallization] | NMR (solvent) δ, ppm | IR (method) cm$^{-1}$ | MS m/z | Elemental Analysis (%) upper column: found lower column: calcd. |
|---|---|---|---|---|---|---|
| 45 (24a) | White crystal | 118–119 [isopropyl ether] | (CDCl$_3$) 1.38 (t, J=7.1Hz, 3H), 1.87 (bs, 1H), 2.51–2.60 (m, 1H), 2.69–2.78 (m, 1H), 2.95 (bs, 2H), 4.33 (q, J=7.1Hz, 2H), 4.54 (s, 1H), 4.81 and 6.39 (ABq, J=12.4 Hz, 2H), 5.01 (bs, 1H), 6.84–7.87 (m, 12H) | (KBr tablet) 3264, 1705, 1570, 1243 | 466 (M$^+$) | C$_{25}$H$_{26}$N$_2$O$_5$S<br>C  H  N<br>64.21  5.65  5.94<br>64.36  5.62  6.00 |
| 46 (25a) | White crystal | 126–128 [methanol] | (CDCl$_3$) 1.22–1.77 (m, 2H), 2.24–3.06 (m, 5H), 3.80 (s, 3H), 4.52 (s, 1H), 4.79 and 6.36 (ABq, J=12.6, 2H), 6.80 (d, J=9.4Hz, 1H), 6.98–7.95 (m, 11H) | (CHCl$_3$) 3280, 1708, 1613, 1311, 1159, 1121, 1094, 1005 | 466 (M$^+$) | C$_{25}$H$_{26}$N$_2$O$_5$S<br>C  H  N<br>64.38  5.62  5.62<br>64.36  5.62  6.00 |
| 47 (24b') | White crystal | 130 (unclear) [ethyl acetate-hexane] | (DMSO-d$_6$) 2.30–2.57 (m, 2H), 2.79–2.83 (m, 2H), 4.65 (s, 1H), 4.90 and 6.45 (ABq, J=11.7Hz, 2H), 6.77–7.86 (m, 12H) | (KBr tablet) 1610, 1378, 1324, 1158 | — (M$^+$) | C$_{23}$H$_{22}$N$_2$O$_5$S.0.5H$_2$O<br>C  H  N<br>62.10  5.04  6.20<br>61.98  5.16  6.28 |
| 48 (25b') | White crystal | 251–254 (decomposed) [isopropanol] | (DMSO-d$_6$) 1.46–1.52 (m, 2H), 2.25–2.8 (m, 5H), 4.69 (s, 1H) 4.93 and 6.48 (ABq, J=11.8Hz, 2H), 6.81 (d, J=8.5Hz, 1H), 7.3–718 (m, 11H), 7.89 (d, J=2.2Hz, 1H) | (KBr tablet) 3050, 1619, 1538, 1384, 1322, 1159, 1006 | 452 (M$^+$) | C$_{24}$H$_{24}$N$_2$O$_5$S.0.5H$_2$O<br>C  H  N<br>62.78  5.27  5.68<br>62.46  5.46  6.07 |

EXAMPLE 49

Methyl (E,Z)-11-[3-(phenylsulfonyl)amino]propylidene-6,11-dihydrodibenz-[b,e]oxepin-2-carboxylate (Compound E/Z-28a)

The desired compound was obtained in a manner similar to Example 1, using Compound i obtained in Reference Example 9. The ratio of E/Z was approximately 7:3.

EXAMPLE 50

Methyl (E,Z)-11-[3-(phenylsulfonyl)amino]propylidene-6,11-dihydrodibenz-[b,e]oxepin-2-acetate (Compound E/Z-29a)

The desired compound was prepared in a manner similar to Example 1, using Compound j obtained in Reference Example 10. The ratio of E/Z was approximately 3:7.

EXAMPLE 51

Methyl (E)-11-[2-(phenylsulfonyl)amino]ethylidene-6,11-dihydrodibenz-[b,e]oxepin-2-carboxylate (Compound E-30a)

The desired compound was prepared in a manner similar to Example 1, using Compound k obtained in Reference Example 11.

EXAMPLE 52

(E)-11-[3-(Phenylsulfonyl)amino]propylidene-6,11-dihydrodibenz-[b,e]oxepin-2-carboxylic acid (Compound E-28b) and
(Z)-11-[3-(phenylsulfonyl)amino]propylidene-6,11-dihydrodibenz-[b,e]oxepin-2-carboxylic acid.0.5 isopropanol (Compound Z-28b')

Compound E/Z-28a (1.0 g) obtained in Example 49 was hydrolyzed in a manner similar to Example 21 to prepare Compound E/Z-28b. The obtained crude product rich in E-form was recrystallized from isopropanol-isopropyl ether to obtain 0.2 g of E-form (Compound E-28b). Further Z-form (Compound Z-28b') solidified with isopropyl ether was obtained from the filtrate rich in Z-form.

EXAMPLE 53

(Z)-11-[3-(Phenylsulfonyl)amino]propylidene-6,11-dihydrodibenz-[b,e]oxepin-2-acetic acid.0.5 methanol.0.25 hydrate (Compound Z-29b')

Compound E/Z-29a obtained in Example 50 was hydrolyzed in a manner similar to Example 21 to prepare (Z)-11-[3-(phenylsulfonyl)amino]propylidene-6,11-dihydrodibenz-[b,e]oxepin-2-acetic acid (Compound Z-29b) which contained 93% of Z-form. This compound was treated in a manner similar to Example 41 to give the sodium salt.

EXAMPLE 54

(E)-11-[2-(Phenylsulfonyl)amino]ethylidene-6,11-dihydrodibenz-[b,e]oxepin-2-carboxylic acid.0.25 hydrate (Compound E-30b')

Compound E-30a obtained in Example 51 was hydrolyzed in a manner similar to Example 21 to prepare the desired compound.

Physicochemical properties of the compounds obtained in Examples 49 through 54 are shown in Table 6-5.

TABLE 6-5

| Example No. (Compound No.) | Appearance | mp (°C.) [solvent for recrystallization] | NMR (solvent) δ, ppm | IR (method) cm$^{-1}$ | MS m/z | Elemental Analysis (%) upper column: found lower column: calcd. |
|---|---|---|---|---|---|---|
| 49 (E/Z-28a) | Colorless oil | — | (CDCl$_3$) 2.22-2.62 (m, 2H), 2.82-3.26 (m, 2H), 3.81 (s, 3H), 4.95-5.57 (m, 2H), 5.91 (t, J=6.9 Hz, 1H), 6.71 (d, J=9.0Hz, 1H), 7.05-8.05 (m, 12H) (E-form) | — | 449 (M$^+$) | — |
| 50 (E/Z-29a) | Colorless oil | — | (CDCl$_3$) 2.26-2.70 (m, 2H), 2.89-3.23 (m, 2H), 3.45 (s, 2H), 3.61 (s, 3H), 5.07 (s, 2H), 5.49 (t, J=7.7Hz, 1H), 6.63-7.29 (m, 13H) (Z-form) | (neat) 3282, 1735, 1488, 1327, 1226, 1159, 1010 | 463 (M$^+$) | |
| 51 (E-30a) | Colorless oil | — | (CDCl$_3$) 3.40-3.57 (m, 2H), 3.78 (s, 3H), 5.11 (bs, 2H), 5.91 (t, J=7.4Hz, 1H), 6.65 (d, J=9.6 Hz, 1H), 6.90-7.98 (m, 12H) | — | 435 (M$^+$) | — |
| 52 (E-28b) | White crystal | 211-212 [isopropanol] [isopropyl ether] | (DMSO-d$_6$) 2.25-2.50 (m, 2H), 2.88-2.95 (m, 2H), 4.95 (bs, 1H), 5.50 (bs, 1H), 6.00 (t, J=7.2Hz, 1H), 6.78-7.87 (m, 12H), 12.71 (bs, 1H) | (KBr tablet) 3278, 1682, 1604, 1313, 1247, 1154 | 435 (M$^+$) | C$_{24}$H$_{21}$NO$_5$S<br>C  H  N<br>66.03  4.76  3.16<br>66.19  4.86  3.22 |
| 52 (Z-28b') | Colorless amorphous | 130 (unclear) [isopropyl ether]* | (DMSO-d$_6$) 2.42-2.50 (m, 2H), 2.92-2.97 (m, 2H), 5.26 (bs, 2H), 5.59 (t, J=7.0Hz, 1H), 6.87 (d, J=8.5Hz, 1H), 7.30-7.80 (m, 11H), 12.70 (bs, 1H) | (KBr tablet) 3228, 1674, 1607, 1409, 1308, 1249, 1157, 1094, 1005 | 435 (M$^+$) | C$_{24}$H$_{21}$NO$_5$S.0.5C$_3$H$_8$O<br>C  H  N<br>65.84  5.55  2.87<br>65.79  5.41  3.01 |
| 53 (Z-29b') | White | Impossible | — | (KBr tablet) | — | C$_{25}$H$_{22}$NO$_5$SNa.0.5CH$_4$O. |

TABLE 6-5-continued

| Example No. (Compound No.) | Appearance | mp (°C.) [solvent for re-crystal-lization] | NMR (solvent) δ, ppm | IR (method) cm$^{-1}$ | MS m/z | Elemental Analysis (%) upper column: found lower column: calcd. | | |
|---|---|---|---|---|---|---|---|---|
| | solid | to measure due to hygroscopic nature [isopropyl ether]* | | 3400, 1574, 1487, 1389, 1307, 1159, 1093, 1012 | | 0.25H$_2$O | | |
| | | | | | | C | H | N |
| | | | | | | 62.39 | 5.36 | 2.67 |
| | | | | | | 62.25 | 5.02 | 2.85 |
| 54 (E-30b') | White solid | 254–257 (decom-posed) [aceto-nitrile] | (DMSO-d$_6$) 3.5 (bs, 2H), 4.96 (bs, 1H), 5.39 (bs, 1H), 5.91 (t, J=7.2Hz, 1H), 6.80 (d, J=8.5Hz, 1H), 7.14 (d, J=7.3Hz, 1H), 7.25–7.75 (m, 9H), 7.80 (d, J=2.2Hz, 1H), 7.93 (t, J=5.2Hz, 1H) | (KBr tablet) 3270, 1680, 1605, 1311, 1247, 1154 | 421 (M$^+$) | C$_{23}$H$_{19}$NO$_5$S.0.25H$_2$O | | |
| | | | | | | C | H | N |
| | | | | | | 64.92 | 4.40 | 3.52 |
| | | | | | | 64.85 | 4.61 | 3.29 |

In Examples 55 through 60 described below, the desired compound was prepared in a manner similar to Example 1, using the corresponding starting material (Compound r, s, t or u) and sulfonyl compounds.

EXAMPLE 55

Methyl 11-[2-[(phenylsulfonyl)amino]ethyl]thio-6,11-dihy-drodibenzo[b,e]thiepin-2-carboxylate (Compound 55a)

EXAMPLE 56

Methyl 5-[2-[(phenylsulfonyl)amino]ethyl]thio-10,11-dihydro-5H-dibenzo[a,d]cyclohepten-3-carboxylate (Compound 59a)

EXAMPLE 57

Methyl 5-[2-[(styrylsulfonyl)amino]ethyl]thio-10,11-dihydro-5H-dibenzo[a,d]cyclohepten-3-carboxylate (Compound 60a)

EXAMPLE 58

Methyl 5-[2-[(phenylsulfonyl)amino]ethyl]thio-5H-dibenzo-[a,d]cyclohepten-3-carboxylate (Compound 64a)

EXAMPLE 59

Methyl 5-[2-[(styrylsulfonyl)amino]ethyl]thio-5H-dibenzo-[a,d-]cyclohepten-3-carboxylate (Compound 65a)

EXAMPLE 60

Methyl 10-[2-[(phenylsulfonyl)amino]ethyl]thio-4,10-dihydro-thieno[3,2-c][1]benzoxepin-8-acetate (Compound 67a)

Physicochemical properties of the compounds obtained in Examples 55 through 60 are shown in Table 6-6.

EXAMPLE
b)
64
b)
65
b)
66
4,10

TABLE 6-6

| Ex. No. (Compound No.) | Appearance | M. P. (°C.) (solvent for recrystallization) | NMR (solvent) δ, ppm | IR (method) cm$^{-1}$ | MS m/z | Elemental Analysis (%) upper column: found lower column: calcd. |
|---|---|---|---|---|---|---|
| 55 (55a) | Pale yellow amorphous | — | (CDCl$_3$) 2.38–2.73(m, 2H), 2.82–3.22(m, 2H), 3.63 and 5.62(ABq, J=15Hz, 2H), 3.86(s, 3H), 5.11 (s, 1H), 7.01–8.10(m, 12H) | (CHCl$_3$) 1715, 1591, 1328, 1299, 1160 | — | — |
| 56 (59a) | Colorless oil | — | (CDCl$_3$) 2.30–2.60(m, 2H), 2.70–3.10(m, 4H), 3.60–4.00(m, 2H), 3.89(s, 3H), 4.98(s, 1H), 4.90–5.24(m, 1H), 6.92–7.92(m, 12H) | (CHCl$_3$) 1712, 1636, 1280, 1105 | — | — |
| 57 | Colorless | — | (CDCl$_3$) 2.61(t, 2H, J=6.48Hz), | — | — | — |

TABLE 6-6-continued

| Ex. No. (Compound No.) | Appearance | M. P. (°C.) (solvent for recrystallization) | NMR (solvent) δ, ppm | IR (method) cm$^{-1}$ | MS m/z | Elemental Analysis (%) upper column: found lower column: calcd. |
|---|---|---|---|---|---|---|
| (60a) | oil | — | 2.70–3.22(m, 4H), 3.60–4.00(m, 2H), 3.88(s, 3H), 4.86(t, 1H, J=6.04Hz), 5.11(s, 1H), 6.70(d, 1H, J=15.4Hz), 6.90–7.54(m, 11H), 7.81(dd, 1H, J=1.54, 7.91Hz), 7.90(s, 1H) | | | |
| 58 (64a) | Colorless oil | — | (CDCl$_3$) 2.30–2.50(m, 2H), 2.72–3.00(m, 2H), 3.92(s, 3H), 4.74–4.96(m, 1H), 5.14(s, 1H), 6.99 (s, 1H), 7.00(s, 1H), 6.98–7.58 (m, 10H), 7.80(dd, 1H, J=2.20, 7.50Hz), 7.94(d, 1H, J=2.20Hz) | (CHCl$_3$) 1716, 1601, 1280, 1162 | — | — |
| 59 (65a) | Colorless oil | — | (CDCl$_3$) 2.28–2.62(m, 2H), 2.80–3.06(m, 2H), 3.91(s, 3H), 3.50–3.80(m, 1H), 5.26(s, 1H), 6.64 (d, 1H, J=15.4Hz), 7.01(s, 1H), 7.03(s, 1H), 7.10–7.48(m, 11H), 7.80–8.00(m, 2H) | (CHCl$_3$) 1716, 1602, 1279, 1142, 971 | — | — |
| 60 (67a) | Colorless oil | — | (CDCl$_3$) 2.35–3.06(m, 4H), 3.49 (s, 2H), 3.61(s, 3H), 4.75 and 5.31(ABq, J=15.0Hz, 2H), 4.92 (s, 1H), 5.14–5.34(m, 1H), 6.53 (d, J=5.8Hz, 1H), 6.91–7.87(m, 9H) | — | 489 (M$^+$) | — |

In Examples 61 through 66 described below, the desired compound was prepared in a manner similar to Example 21, using the corresponding ester.

EXAMPLE 61

11-[2-[(Phenylsulfonyl)amino]ethyl]thio-6,11-dihydrodibenzo-[b,e]thiepin-2-carboxylic acid (Compound 55b)

EXAMPLE 62

5-[2-[(Phenylsulfonyl)amino]ethyl]thio-10,11-dihydro-5H-dibenzo[a,d]cyclohepten-3-carboxylic acid (Compound 59b) Example 63

5-[2-[(Styrylsulfonyl)amino]ethyl]thio-10,11-dihydro-5H-dibenzo[a,d]cyclohepten-3-carboxylic acid (Compound 60b)

EXAMPLE 64

5-[2-[(Phenylsulfonyl)amino]ethyl]thio-5H-dibenzo[a,d]-cyclohepten-3-carboxylic acid (Compound 64b)

EXAMPLE 65

5-[2-[(Styrylsulfonyl)amino]ethyl]thio-5H-dibenzo[a,d]-cyclohepten-3-carboxylic acid (Compound 65b)

EXAMPLE 66

10-[2-[(Phenylsulfonyl)amino]ethyl]thio-4,10-dihydrothieno-[3,2-c][1]benzoxepin-8-acetic acid (Compound 67b)

Physicochemical properties of the compounds obtained in Examples 61 through 66 are shown in Table 6-7.

TABLE 6-7

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. |
|---|---|---|---|---|---|---|
| 61 (55b) | Pale yellow crystal | 98 (decomposed) [isopropyl ether] | (DMSO-d$_6$) 2.46–2.51(m, 2H), 2.83–2.91(m, 2H), 3.32(bs, 1H), 5.55(bs, 1H), 5.74(bs, 1H), 7.13–8.01(m, 12H), 12.89(bs, 1H) | (KBr tablet) 3278, 1681, 1594, 1310, 1156 | — | C$_{23}$H$_{21}$NO$_4$S$_3$<br>C  H  N<br>58.42  4.86  2.91<br>58.58  4.49  2.97 |
| 62 (59b) | Pale yellow crystal | 141–144 [ethyl acetate-hexane] | (DMSO-d$_6$) 2.39–2.51(m, 2H), 2.77–2.92(m, 4H), 3.66–3.75(m, 2H), 5.38(s, 1H), 7.11–7.31(m, 4H), 7.54–7.64(m, 3H), 7.73–7.81(m, 4H), 7.93(s, 1H) | (KBr tablet) 3282, 1693, 1446, 1328, 1154 | — | C$_{24}$H$_{23}$NO$_4$S$_2$·0.2C$_3$H$_8$O<br>C  H  N<br>63.18  5.34  2.97<br>63.46  5.33  3.01 |

TABLE 6-7-continued

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. | | |
|---|---|---|---|---|---|---|---|---|
| 63 (60b) | Pale yellow crystal | 158–161 [isopropyl ether] | (DMSO-d$_6$) 2.53(t, 2H, J=7.53Hz), 2.84–3.02(m, 4H), 3.69–3.78(m, 2H), 5.44(s, 1H), 7.06–7.50(m, 10H), 7.67–7.77(m, 3H), 7.98 (d, 1H), J=1.71Hz) | (KBr tablet) 3278, 1690, 1419, 1318, 1285, 1142, 973 | — | C$_{26}$H$_{25}$NO$_4$S$_2$ | | |
| | | | | | | C | H | N |
| | | | | | | 64.98 | 5.19 | 2.90 |
| | | | | | | 65.11 | 5.25 | 2.92 |
| 64 (64b) | Pale yellow crystal | 167–170 [acetonitrile] | (DMSO-d$_6$) 2.20–2.27(m, 2H), 2.69–2.74(m, 2H), 5.57(s, 1H), 7.04 and 7.08(ABq, 2H, J=12.2Hz), 7.32–7.75(m, 10H), 7.85(dd, 1H, J=1.70, 7.82Hz), 8.07(d, 1H, J=1.51Hz) | (KBr tablet) 3270, 1635, 1446, 1309, 1155 | — | C$_{24}$H$_{21}$NO$_4$S$_2$·0.1C$_3$H$_8$O | | |
| | | | | | | C | H | N |
| | | | | | | 63.61 | 4.51 | 3.21 |
| | | | | | | 63.78 | 4.80 | 3.06 |
| 65 (65b) | Pale yellow crystal | 120 (decomposed) [isopropanol] | (DMSO-d$_6$) 2.32–2.40(m, 2H), 2.80–3.08(m, 2H), 5.47(s, 1H), 6.97 (s, 2H), 7.13(d, 1H, J=15.4Hz), 7.25–7.48(m, 8H), 7.67–7.72(m, 3H), 7.80(dd, 1H, J=1.46, 7.81 Hz), 8.00(d, 1H, J=1.22Hz) | (KBr tablet) 3400, 3058, 1584, 1537, 1404, 1382, 1143, 970 | — | C$_{26}$H$_{23}$NO$_4$S$_2$ | | |
| | | | | | | C | H | N |
| | | | | | | 65.64 | 4.69 | 2.92 |
| | | | | | | 65.39 | 4.85 | 2.93 |
| 66 (67b) | Pale yellow crystal | 186–187 (decomposed) [methanol] | (DMSO-d$_6$) 2.50–2.60(m, 2H), 2.75–2.95(m, 2H), 3.52(s, 2H), 4.80 and 5.40(ABq, J=15.4Hz, 2H), 5.30(s, 1H), 6.76(d, J=5.1Hz, 1H), 7.02(d, J=7.8Hz, 1H), 7.14–7.18(m, 2H), 7.39(d, J=5.1Hz, 1H), 7.56–7.80(m, 6H), 12.35 (bs, 1H) | (KBr tablet) 3450, 3240, 1709, 1499, 1327, 1160 | 475(M$^+$) | C$_{22}$H$_{21}$NO$_5$S$_3$ | | |
| | | | | | | C | H | N |
| | | | | | | 55.46 | 4.39 | 3.11 |
| | | | | | | 55.56 | 4.45 | 2.95 |

In Examples 67 through 76 described below, the desired compound was prepared, using the corresponding 11-(2-aminoethyl)thio-6,11-dihydrodibenz-[b,e]oxepine derivative (Compound f or o), either by changing the benzenesulfonyl chloride in Example 1 to the corresponding acid chloride or acid anhydride, or in a manner similar to Example 1.

EXAMPLE 67

Methyl 11-[2-[(benzoyl)amino]ethyl]thio-6,11-dihydrodibenz-[b,e]oxepin-2-carboxylate (Compound 32a)

EXAMPLE 68

Methyl 11-[2-[(2-methoxybenzoyl)amino]ethyl]thio-6,11-dihydro-dibenz[b,e]oxepin-2-carboxylate (Compound 33a)

EXAMPLE 69

Methyl 11-[2-[(2,6-dimethoxybenzoyl)amino]ethyl]thio-6,11-dihydrodibenz-[b,e]oxepin-2-carboxylate (Compound 35a)

EXAMPLE 70

Methyl 11-[2-[(3,4,5-trimethoxybenzoyl)amino]ethyl]thio-6,11-dihydrodibenz-[b,e]oxepin-2-carboxylate·0.3 hydrate (Compound 36a')

EXAMPLE 71

Methyl 11-[2-(2,3,4-trimethoxybenzoyl)amino]ethyl]thio-6,11-dihydrodibenz-[b,e]oxepin-2-carboxylate (Compound 37a)

EXAMPLE 72

Methyl 11-[2-[(2-methylthenoyl)amino]ethyl]thio-6,11-dihydrodibenz-[b,e]oxepin-2-carboxylate (Compound 38a)

EXAMPLE 73

Methyl 11-[2-[(cyclohexanecarbonyl)amino]ethyl]thio-6,11-dihydrodibenz-[b,e]oxepin-2-carboxylate (Compound 39a)

EXAMPLE 74

Methyl 11-[2-[(hexanoyl)amino]ethyl]thio-6,11-dihydrodibenz-[b,e]oxepin-2-carboxylate (Compound 40a)

EXAMPLE 75

Methyl 11-[2-[(cinnamoyl)amino]ethyl]thio-6,11-dihydrodibenz-[b,e]oxepin-2-carboxylate (Compound 41a)

EXAMPLE 76

Methyl 11-[2-[[(coumarin-3-yl)carbonyl]amino]ethyl]thio-6,11-dihydrodibenz-[b,e]oxepin-2-acetylate (Compound 42a)

EXAMPLE 77

Methyl 11-[2-[(2-hydroxybenzoyl)amino]ethyl]thio-6,11-dihydrodibenz-[b,e]oxepin-2-carboxylate (Compound 34a)

Compound 33a, 2.1 g, obtained in Example 68 was dissolved in 100 ml of methylene chloride and 0.6 ml of boron trifluoride was dropwise added to the solution at −78° C. under a nitrogen atmosphere. After stirring for further 2.5 hours, pieces of ice were added to the reaction mixture to decompose an excess of the reagent. Then, extraction was performed with 200 ml of methylene chloride. After washing with water, the extract was dried over anhydrous magnesium sulfate. The solvent was distilled off under reduced pressure. The resulting residue was subjected to silica gel column chromatography (eluting solvent; hexane:ethyl acetate = 1:1) to give 1.5 g of the desired compound.

Physicochemical properties of the compounds obtained in Examples 67 through 77 are shown in Table 6-8.

TABLE 6-8

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. | | |
|---|---|---|---|---|---|---|---|---|
| | | | | | | | | |
| 67 (32a) | White crystal | 150–151 [isopropyl ether] | (CDCl$_3$) 2.38–2.86(m, 2H), 3.34–3.75(m, 2H), 3.80(s, 3H), 4.84 and 6.36(ABq, J=12.6Hz, 2H), 5.06(s, 1H), 6.81(d, J=9.0Hz, 1H), 7.10–8.11(m, 12H) | (KBr tablet) 3336, 1718, 1635, 1527, 1295, 1253, 1120, 1009 | 433(M$^+$) | C$_{25}$H$_{23}$NO$_4$S C 69.21 69.26 | H 5.27 5.35 | N 3.33 3.23 |
| 68 (33a) | White crystal | 123–125 [isopropyl ether] | (CDCl$_3$) 2.50–2.89(m, 2H), 3.40–3.79(m, 2H), 3.76(s, 3H), 3.83 (s, 3H), 4.82 and 6.35(ABq, J=12.9Hz, 2H), 5.05(s, 1H), 6.67–8.47(m, 11H) | (KBr tablet) 3372, 1708, 1645, 1602, 1533, 1295, 1253, 768 | — | C$_{26}$H$_{25}$NO$_3$S C 67.37 67.42 | H 5.44 5.61 | N 3.02 3.03 |
| 69 (35a) | White crystal | 163–164 [toluene] | (CDCl$_3$ + DMSO-d$_6$) 2.41–2.83(m, 2H), 3.16–3.54(m, 2H), 3.66(s, 3H), 3.74(s, 6H), 4.90 and 6.33(ABq, J=12.4Hz, 2H), 5.23(s, 1H), 6.51 (d, J=8.0Hz, 2H), 6.78(d, J= 8.6Hz, 1H), 7.02–7.40(m, 5H), 7.67(dd, J=2.5, 8.6Hz, 1H), 7.82 (bs, 1H), 7.95(d, J=2.5Hz, 1H) | (KBr tablet) 3400, 2948, 1718, 1636, 1597, 1241, 1112 | 493(M$^+$) | C$_{27}$H$_{27}$NO$_6$S C 65.50 65.70 | H 5.80 5.51 | N 2.71 2.84 |
| 70 (36a') | Colorless amorphous | 78–81 (unclear) [isopropyl ether]* | (CDCl$_3$) 2.51–2.83(m, 2H), 3.27–3.78(m, 2H), 3.84(s, 12H), 4.85 and 6.34(ABq, J=12.8Hz, 2H), 5.04(s, 1H), 6.80(d, J=8.5Hz, 1H), 7.01(s, 2H), 7.12–7.37(m, 4H), 7.73(dd, J=2.4, 8.5Hz, 1H), 7.93(d, J=2.4Hz, 1H) | (KBr tablet) 3400, 2934, 1715, 1633, 1610, 1582, 1498, 1332, 1239, 1127, 1005 | 523(M$^+$) | — | | |
| 71 (37a) | Colorless amorphous | — | (CDCl$_3$) 2.51–2.87(m, 2H), 3.40–3.86(m, 2H), 3.78(s, 6H), 3.83 (s, 3H), 3.86(s, 3H), 4.87 and 6.41(ABq, J=12.9Hz, 2H), 5.11(s, 1H), 6.70(d, J=5.0Hz, 1H), 6.85 (d, J=5.4Hz, 1H), 7.12–7.40(m, 4H), 7.64–8.04(m, 3H), 8.12–8.45 (m, 1H) | (KBr tablet) 3380, 2940, 1711, 1655, 1596, 1279, 1093, 1006 | 523(M$^+$) | — | | |
| 72 (38a) | Colorless amorphous | — | (CDCl$_3$) 2.42(s, 3H), 2.42–2.88(m, 2H), 3.31–3.78(m, 2H), 3.81(s, 3H), 4.85 and 6.36(ABq, J=12.6Hz, 2H), 5.07(s, 1H), 6.35(bs, 1H), 6.71–6.98(m, 2H), 7.14–7.44(m, 5H), 7.74(dd, J=2.0, 8.8Hz, 1H), 7.95(d, J=2.0Hz, 1H) | (KBr tablet) 3300, 2946, 1720, 1617, 1234, 1118, 1009 | 453(M$^+$) | — | | |
| 73 (39a) | Colorless amorphous | — | (CDCl$_3$) 1.1–2.2(m, 11H), 2.4–2.7 (m, 2H), 3.25–3.55(m, 2H), 3.89 (s, 3H), 4.91 and 6.41(ABq, J= 12.9Hz, 2H), 5.05(s, 1H), 5.71 (bs, 1H), 6.86(d, J=8.4Hz, 1H), 7.1–7.5(m, 4H), 7.7–8.0(m, 2H) | (KBr tablet) 3312, 1717, 1641, 1530, 1250, 1117, 1007 | — | — | | |
| 74 (40a) | Colorless amorphous | — | (CDCl$_3$) 0.8–2.0(m, 9H), 2.4–2.9 (m, 4H), 3.3–3.5(m, 2H), 3.89(s, 3H), 4.91 and 6.40(ABq, J=12.7 Hz, 2H), 6.86(d, J=8.6Hz, 1H), 7.25–7.39(m, 4H), 7.80(dd, J= 2.2 and 8.6Hz, 1H), 7.96(d, J= 2.2Hz, 1H) | (KBr tablet) 3310, 1703, 1632, 1548, 1281, 1250, 1115, 1008 | — | — | | |
| 75 (41a) | Pale yellow amorphous | — | (CDCl$_3$) 2.43–2.83(m, 2H), 3.26–3.72(m, 2H), 3.49(s, 2H), 3.61 (s, 3H), 4.78 and 6.19(ABq, J= 13.1Hz, 2H), 4.97(s, 1H), 6.38 (d, J=15.6Hz, 1H), 6.61–7.56(m, 12H), 7.59(d, J=15.6Hz, 1H) | (CHCl$_3$) 3384, 1733, 1667, 1627, 1500, 1123, 1014 | 473(M$^+$) | — | | |
| 76 | Light red | — | (CDCl$_3$) 2.47–2.90(m, 2H), 3.22– | (CHCl$_3$) | 515(M$^+$) | — | | |

TABLE 6-8-continued

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. |
|---|---|---|---|---|---|---|
| (42a) | amorphous | | 3.69(m, 2H), 3.52(s, 2H), 3.61 (s, 3H), 4.80 and 6.25(ABq, J=12.6Hz, 2H), 5.04(s, 1H), 6.74 (d, J=8.0Hz, 1H), 6.91–7.71(m, 10H), 8.80(s, 1H), 8.73–9.09 (m, 1H) | 3344, 1720, 1710, 1655, 1611, 1570, 1540, 1161, 1122, 1011 | | |
| 77 (34a) | Colorless amorphous | 149–151 [isopropyl ether]* | (CDCl$_3$) 2.47–2.86(m, 2H), 3.32–3.71(m, 2H), 3.83(s, 3H), 4.84 and 6.34(ABq, J=13.1Hz, 2H), 5.03 (s, 1H), 6.81(d, J=8.4Hz, 1H), 6.83–7.55(m, 8H), 7.76(dd, J=2.2, 8.4Hz, 1H), 7.98(d, J=2.2Hz, 1H), 12.22(bs, 1H) | (CHCl$_3$) 1716, 1646, 1599, 1297, 1252, 1120, 1008 | 449(M$^+$) | — |

In Examples 78 through 88 described below, the desired compound was prepared by hydrolyzing an ester of the corresponding oxepin derivative in a manner almost similar to Example 21.

EXAMPLE 78

11-[2-[(Benzoyl)amino]ethyl]thio-6,11-dihydrodibenz-[b,e]oxepin-2-carboxylic acid (Compound 32b)

EXAMPLE 79

11-[2-[(2-Methoxybenzoyl)amino]ethyl]thio-6,11-dihydrodibenz-[b,e]oxepin-2-carboxylic acid (Compound 33b)

EXAMPLE 80

11-[2-[(2,6-Dimethoxybenzoyl)amino]ethyl]thio-6,11-dihydrodibenz-[b,e]oxepin-2-carboxylic acid.0.2 hydrate (Compound 35b')

EXAMPLE 81

11-[2-[(3,4,5-Trimethoxybenzoyl)amino]ethyl]thio-6,11-dihydrodibenz-[b,e]oxepin-2-carboxylic acid (Compound 36b)

EXAMPLE 82

11-[2-[(2,3,4-Trimethoxybenzoyl)amino]ethyl]thio-6,11-dihydrodibenz-[b,e]oxepin-2-carboxylic acid (Compound 37b)

EXAMPLE 83

11-[2-[(2-Methylthenoyl)amino]ethyl]thio-6,11-dihydrodibenz-[b,e]oxepin-2-carboxylic acid (Compound 38b)

EXAMPLE 84

11-[2-[(Cyclohexanecarbonyl)amino]ethyl]thio-6,11-dihydrodibenz-[b,e]oxepin-2-carboxylic acid (Compound 39b)

EXAMPLE 85

11-[2-[(Hexanoyl)amino]ethyl]thio-6,11-dihydrodibenz-[b,e]-oxepin-2-carboxylic acid (Compound 40b)

EXAMPLE 86

11-[2-[(Cinnamoyl)amino]ethyl]thio-6,11-dihydrodibenz-[b,e]-oxepin-2-carboxylic acid.0.25 hydrate (Compound 41b')

EXAMPLE 87

11-[2-[[(Coumarin-3-yl)carbonyl]amino]ethyl]thio-6,11-dihydrodibenz-[b,e]oxepin-2-acetic acid.0.5 hydrate (Compound 42b')

EXAMPLE 88

11-[2-[(2-Hydroxybenzoyl)amino]ethyl]thio-6,11-dihydrodibenz-[b,e]oxepin-2-carboxylic acid.0.5 hydrate (Compound 34b')

Physicochemical properties of the compounds obtained in Examples 78 through 88 are shown in Table 6-9.

TABLE 6-9

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. |
|---|---|---|---|---|---|---|
| 78 (32b) | White crystal | 193-194 [isopropanol] | (DMSO-d$_6$) 2.5-2.75(m, 2H), 3.2-3.6(m, 2H), 5.00 and 6.25(ABq, J=12.4Hz, 2H), 5.44(s, 1H), 6.83 (d, J=8.6Hz, 1H), 7.2-7.9(m, 11H), 8.5(m, 1H) | (KBr tablet) 3322, 1683, 1630, 1607, 1537, 1254, 1112, 1012 | 419(M$^+$) | C$_{24}$H$_{21}$NO$_4$S<br>C  H  N<br>68.67  5.23  3.36<br>68.72  5.05  3.34 |
| 79 (33b) | White crystal | 198-200 [isopropanol] | (DMSO-d$_6$) 2.50-2.62(m, 2H), 3.46-3.54(m, 2H), 3.88(s, 3H), 5.06 and 6.27(ABq, J=12.7Hz, 2H), 5.49(s, 1H), 6.86-8.42(m, 11H), 12.8(bs, 1H) | (KBr tablet 3340, 1699, 1608, 1553, 1232, 1120, 759 | — | C$_{25}$H$_{23}$NO$_5$S<br>C  H  N<br>66.85  5.12  3.21<br>66.80  5.16  3.12 |
| 80 (35b′) | White crystal | 232-234 [isopropanol] | (DMSO-d$_6$) 2.45-2.7(m, 2H), 3.2-3.4(m, 2H), 3.68(s, 6H), 5.06 and 6.28(ABq, J=12.7Hz, 2H), 5.47(s, 1H), 6.65(d, J=8.4Hz, 2H), 6.88 (d, J=8.5Hz, 1H), 7.27(t, J=8.4 Hz, 1H), 7.35-7.5(m, 4H), 7.72 (dd, J=2.2, 8.5Hz, 1H), 8.02(d, J=2.2Hz), 8.20(t, J=5.6Hz, 1H), 12.75(bs, 1H) | (KBr tablet) 3388, 3262, 1701, 1607, 1474, 1254, 1231, 1115, 1005 | 479(M$^+$) | C$_{26}$H$_{25}$NO$_6$S.0.2H$_2$O<br>C  H  N<br>64.67  5.36  2.83<br>64.64  5.30  2.90 |
| 81 (36b) | White crystal | 215-217 [toluene] | (DMSO-d$_6$) 2.55-2.7(m, 2H), 3.4-3.55(m, 2H), 3.70(s, 3H), 3.83 (s, 6H), 5.05 and 6.28(ABq, J=12.6Hz, 2H), 5.47(s, 1H), 6.87 (d, J=8.6Hz, 1H), 7.19(s, 2H), 7.35-7.5(m, 4H), 7.71(dd, J=2.2, 8.6Hz, 1H), 8.05(d, J=2.2Hz, 1H), 8.59(t, J=5.6Hz, 1H), 12.75(bs, 1H) | (KBr tablet) 3320, 2932, 1686, 1639, 1613, 1580, 1498, 1335, 1232, 1133, 1001 | 509(M$^+$) | C$_{27}$H$_{27}$NO$_7$S<br>C  H  N<br>63.60  5.36  2.68<br>63.64  5.34  2.75 |
| 82 (37b) | White crystal | 214-215.5 [isopropanol] | (DMSO-d$_6$) 2.64(t, J=6.6Hz, 2H), 3.3-3.6(m, 2H), 3.76(s, 3H), 3.83(s, 3H), 3.84(s, 3H), 5.06 and 6.26(ABq, J=12.7Hz, 2H), 5.50(s, 1H), 6.88(8, J=8.5Hz, 1H), 6.90(d, J=8.9Hz, 1H), 7.35-7.50(m, 4H), 7.55(d, J=8.9Hz, 1H), 7.71(dd, J=2.2, 8.5Hz, 1H), 8.05(d, J=2.2Hz, 1H), 8.33(t, J=5.9Hz, 1H) | (KBr tablet) 3354, 1679, 1646, 1613, 1525, 1234, 1091, 1001 | 509(M$^+$) | C$_{27}$H$_{27}$NO$_7$S<br>C  H  N<br>63.45  5.39  2.65<br>63.64  5.34  2.75 |
| 83 (38b) | White crystal | 170-172 [isopropanol] | (DMSO-d$_6$) 2.40(s, 3H), 2.5-2.7(m, 2H), 3.3-3.5(m, 2H), 5.05 and 6.27(ABq, J=12.7Hz, 2H), 5.45(s, 1H), 6.87(d, J=8.5Hz, 1H), 6.95 (d, J=4.9Hz, 1H), 7.35-7.50(m, 4H), 7.55(d, J=4.9Hz, 1H), 7.71 (dd, J=2.2, 8.5Hz, 1H), 8.0-8.1 (m, 2H), 12.75(bs, 1H) | (KBr tablet) 3294, 1684, 1628, 1609, 1255, 1232, 1111, 1008 | 439(M$^+$) | C$_{23}$H$_{21}$NO$_4$S$_2$<br>C  H  N<br>62.99  4.92  3.19<br>62.85  4.82  3.19 |
| 84 (39b) | White crystal | 181-182 [Acetonitrile] | (DMSO-d$_6$) 1.14-1.67(m, 10H), 2.03-2.11(m, 1H), 2.41-2.50(m, 2H), 3.15-3.25(m, 2H), 5.04 and 6.26(ABq, J=12.6Hz, 2H), 5.39(s, 1H), 6.86(d, J=8.5Hz, 1H), 7.35-7.49(m, 4H), 7.70(dd, J=2.2 and 8.5Hz, 1H), 7.80(t, J=5.5Hz, 1H), 7.99(d, J=2.2Hz, 1H) | (KBr tablet) 3336, 1674, 1608, 1548, 1395, 1319, 1231, 1001 | — | C$_{24}$H$_{27}$NO$_4$S<br>C  H  N<br>67.51  6.32  3.26<br>67.74  6.40  3.29 |
| 85 (40b) | White crystal | 123-125 [Isopropanol] | (DMSO-d$_6$) 0.83(t, J=7.0Hz, 3H), 1.18-1.29(m, 4H), 1.43-1.54(m, 2H), 2.05(t, J=7.4Hz, 2H), 2.42-2.54(m, 2H), 3.15-3.33(m, 2H), 5.04 and 6.26(ABq, J=12.6Hz, 2H), 5.41(s, 1H), 6.87(d, J=8.5Hz, 1H), 7.33-7.47(m, 4H), 7.71(dd, J=2.2 and 8.5Hz, 1H), 7.91(t, J=5.7Hz, 1H), 7.99(d, J=2.2Hz, 1H) | (KBr tablet) 3344, 1671, 1606, 1540, 1226, 1204, 1109, 1004 | — | C$_{23}$H$_{27}$NO$_4$S<br>C  H  N<br>66.56  6.81  3.18<br>66.80  6.58  3.39 |
| 86 (41b′) | Pale yellow amorphous | Unclear [isopropyl ether] | — | (KBr tablet) 3400, 1700, 1652, 1608, 1498, 1228, 1013 | 459(M$^+$) | C$_{27}$H$_{25}$NO$_4$S.0.2H$_2$O<br>C  H  N<br>69.66  5.80  2.83<br>69.88  5.54  3.02 |
| 87 (42b′) | Colorless amorphous | 165 (decomposed) [Isopropyl ether] | (DMSO-d$_6$) 2.64(t, J=6.8Hz, 2H), 3.3-3.5(m, 2H), 3.49(s, 2H), 4.95 and 6.11(ABq, J=12.9Hz, 2H), 5.28(s, 1H), 6.75(d, J=8.3Hz, 1H), 7.06(dd, J=2.2, 8.3Hz, 1H), 7.26(d, J=2.2Hz, 1H), 7.3-7.55 (m, 7H), 7.73-7.79(m, 1H), 8.00 (dd, J=1.6, 7.8Hz, 1H), 8.91(s, 1H), 12.3(bs, 1H) | (KBr tablet) 2916, 1704, 1608, 1498, 1229, 1122, 1010 | 501(M$^+$) | C$_{28}$H$_{23}$NO$_6$S.0.5H$_2$O<br>C  H  N<br>65.95  4.54  2.72<br>65.87  4.74  2.74 |

TABLE 6-9-continued

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. | | |
|---|---|---|---|---|---|---|---|---|
| 88 (34b') | White crystal | 125 (unclear) [Isopropyl ether] | (DMSO-d$_6$) 2.6–2.8(m, 2H), 3.45–3.55(m, 2H), 5.04 and 6.25(ABq, J=12.6Hz, 2H), 5.46(s, 1H), 6.86 (d, J=8.5Hz, 1H), 6.92(d, J= 4.6Hz, 1H), 6.8–6.9(m, 1H), 7.3–7.5(m, 5H), 7.71(dd, J=2.0, 8.5 Hz, 1H), 7.84(dd, J=1.5, 7.8Hz, 1H), 8.05(d, J=2.0Hz, 1H), 8.99 (bs, 1H), 12.7(bs, 1H | (KBr tablet) 3350, 1682, 1635, 1597, 1538, 1493, 1235, 1112, 1007 | 435(M$^+$) | C$_{24}$H$_{21}$NO$_5$S.0.5H$_2$O | | |
| | | | | | | C | H | N |
| | | | | | | 64.78 | 4.74 | 3.02 |
| | | | | | | 64.85 | 4.99 | 3.15 |

EXAMPLE 89

Methyl 11-[2-(3-phenylureido)ethyl]thio-6,11-dihydrodibenz-[b,e]oxepin-2-carboxylate (Compound 44a)

Compound f, 2.0 g, obtained in Reference Example 6 was dissolved in 100 ml of methylene chloride and 0.7 ml of phenyl isocyanate was added to the solution. The mixture was stirred at room temperature for 2 hours. The solvent was distilled off under reduced pressure. The residue was extracted with 200 ml of ethyl acetate. The extract was washed with saturated sodium chloride aqueous solution and dried over anhydrous magnesium sulfate. Then, the solvent was distilled off under reduced pressure. The resulting residue was subjected to silica gel column chromatography (eluting solvent; hexane:ethyl acetate=2:1) to give 2.2 g of the desired compound.

In Examples 90 to 92 described below, the desired compound was prepared in a manner similar to Example 89 except for using the corresponding 11-(2-aminoethyl)thio-6,11-dihydrodibenz-[b,e]oxepin derivative (Compound f or o) and an isocyanate, isothiocyanate or chloroformate.

EXAMPLE 90

11-[2-(3-phenylureido)ethyl]thio-6,11-dihydrodibenz-[b,e]oxepin-2-acetate (Compound 45a)

EXAMPLE 91

Methyl 11-[2-[(3-benzyl)thioureido]ethyl]thio-6,11-dihydrodibenz-[b,e]oxepin-2-carboxylate (Compound 46a)

EXAMPLE 92

Methyl 11-[2[[(benzyloxy)carbonyl]amino]ethyl]thio-6,11-dihydrodibenz[b,e]oxepin-2-carboxylate (Compound 53a)

Physicochemical properties of the compounds obtained in Examples 89 through 92 are shown in Table 6-10.

TABLE 6-10

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. | | |
|---|---|---|---|---|---|---|---|---|
| 89 (44a) | Colorless amorphous | — | (CDCl$_3$) 2.33–2.70(m, 2H), 3.03–3.52(m, 2H), 3.81(s, 3H), 4.86 and 6.33(ABq, J=13.3Hz, 2H), 4.99 (s, 1H), 5.78–6.15(m, 1H), 6.80 (d, J=8.2Hz, 1H), 6.91–7.42(m, 9H), 7.65–7.84(m, 2H), 7.94(d, J=2.0Hz, 1H) | (KBr tablet) 1715, 1498, 1435, 1237 1117, 1007 | 448(M$^+$) | — | | |
| 90 (45a) | Colorless amorphous | — | (CDCl$_3$) 2.37–2.66(m, 2H), 3.12–3.34(m, 2H), 3.43(s, 2H), 3.56 (s, 3H), 4.74 and 6.17(ABq, J= 13.8Hz, 2H), 6.68(d, J=9.0Hz, 1H), 6.73–7.56(m, 11H), 8.13(bs, 1H) | (KBr tablet) 3340, 1731, 1647, 1597, 1550, 1498, 1309, 1230, 1163, 1011 | 462(M$^+$) | C$_{26}$H$_{26}$N$_2$O$_4$S | | |
| | | | | | | C | H | N |
| | | | | | | 67.76 | 5.80 | 5.89 |
| | | | | | | 67.51 | 5.67 | 6.06 |
| 91 (46a) | Colorless amorphous | — | (CDCl$_3$) 2.41–2.74(m, 2H), 3.43–3.78(m, 2H), 3.75(s, 3H), 4.56 (d, J=4.0Hz, 2H), 4.80 and 6.25 (ABq, J=12.8Hz, 2H), 5.02(s, 1H), 6.30–6.68(m, 1H), 6.76(d, J=8.6 Hz, 1H), 7.01–7.34(m, 9H), 7.69 (dd, J=2.2, 8.6Hz, 1H), 7.90(d, J=2.2Hz, 1H) | (KBr tablet) 3400, 1717, 1610, 1533, 1242, 1118, 1005 | 478(M$^+$) | — | | |
| 92 (53a) | Colorless amorphous | — | (CDCl$_3$) 2.34–2.73(m, 2H), 3.05–3.48(m, 2H), 3.83(s, 3H), 4.85 and 6.38(ABq, J=11.4Hz, 2H), 5.01 (s, 1H), 5.09(s, 2H), 6.83(d, J= 8.5Hz, 1H), 7.04–7.48(m, 9H), 7.77(dd, J=2.0, 8.5Hz, 1H), | (KBr tablet) 1700. 1609, 1567, 1532, 1431, 1300, 1121, 1013 | 463(M$^+$) | — | | |

TABLE 6-10-continued

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. |
|---|---|---|---|---|---|---|
| | | | 7.96(d, J=2.0Hz, 1H) | | | |

In Examples 93 through 96 described below, the desired compound was prepared by hydrolyzing an ester of the corresponding dibenzoxepine derivative in a manner similar to Example 21.

EXAMPLE 93

11-[2-(3-Phenylureido)ethyl]thio-6,11-dihydrodibenzo-[b,e]-oxepin-2-carboxylic acid (Compound 44b)

EXAMPLE 96

11-[2-[[(Benzyloxy)carbonyl]amino]ethyl]thio-6,11-dihydrodibenz[b,e]oxepin-2-carboxylic acid (Compound 53b)

Physicochemical properties of the compounds obtained in Examples 93 through 96 are shown in Table 6-11.

TABLE 6-11

| Ex. No. (Compound No.) | Appearance | M.P. (°C.) (solvent for recrystallization) | NMR (solvent) δ, ppm | IR (method) cm$^{-1}$ | MS m/z | Elemental Analysis (%) upper column: found lower column: calcd. |
|---|---|---|---|---|---|---|
| 93 (44b) | White crystal | 160–162 [toluene]* | (DMSO-d$_6$) 2.4–2.65(m, 2H), 3.2–3.35(m, 2H), 5.05 and 6.27(ABq, J=12.8Hz, 2H), 5.46(s, 1H), 6.41 (t, J=5.6Hz, 1H), 6.87(d, J=8.5 Hz, 1H), 7.21(t, J=7.8Hz, 2H), 7.35–7.50(m, 6H), 7.72(dd, J=2.0, 8.5Hz, 1H), 8.03(d, J=2.0Hz, 1H), 8.65(s, 1H) | (KBr tablet) 3398, 1693, 1668, 1610, 1553, 1498, 1299, 1254, 1232, 1112, 1010 | 434(M$^+$) | C$_{24}$H$_{22}$N$_2$O$_4$S<br>C  H  N<br>66.31  5.05  5.97<br>66.34  5.10  6.45 |
| 94 (45b′) | White crystal | 108–110 [water]* | (DMSO-d$_6$) 2.45–2.6(m, 2H), 3.3–3.4(m, 2H), 3.47(s, 2H), 4.94 and 6.12(ABq, J=12.8Hz, 2H), 5.25(s, 1H), 6.28(t, J=5.9Hz, 1H), 6.75 (d, J=8.5Hz, 1H), 6.89(t, J=7.3 Hz, 1H), 7.06(dd, J=2.2, 8.5Hz, 1H), 7.2–7.5(m, 9H), 8.58(s, 1H), 12.3(bs, 1H) | (KBr tablet) 3450, 1714, 1673, 1613, 1486, 1439, 1201, 1133, 1005 | 448(M$^+$) | C$_{25}$H$_{24}$N$_2$O$_4$S.0.25H$_2$O<br>C  H  N<br>66.13  5.36  6.21<br>66.28  5.56  6.18 |
| 95 (46b′) | White crystal | 135–136 [toluene] | (DMSO-d$_6$) 2.55–2.7(m, 2H), 3.5–3.8(m, 2H), 4.66(bs, 2H), 5.05 and 6.23(ABq, J=12.7Hz, 2H), 5.46 (s, 1H), 6.88(d, J=8.6Hz, 1H), 7.1–7.5(m, 10H), 7.66(bs, 1H), 7.72(dd, J=2.0, 8.6Hz, 1H), 8.02 (d, J=2.0Hz, 1H), | (KBr tablet) 3275, 1685, 1606, 1553, 1291, 1252, 1236, 1111, 1008 | 464(M$^+$) | C$_{25}$H$_{24}$N$_2$O$_3$S$_2$.0.6 C$_7$H$_8$.H$_2$O<br>C  H  N<br>65.21  5.50  6.25<br>65.20  5.77  5.21 |
| 96 (53b) | Colorless amorphous | — | (DMSO-d$_6$) 2.45–2.55(m, 2H), 3.1–3.25(m, 2H), 5.03 and 6.25(ABq, J=11.1Hz, 2H), 5.05(s, 2H), 5.42 (s, 1H), 6.87(d, J=8.6Hz, 1H), 7.15–7.5(m, 10H), 7.71(dd, J=2.0, 8.6Hz, 1H), 8.03(d, J=2.0Hz, 1H), 12.72(bs, 1H) | (KBr tablet) 3450, 1685, 1609, 1542 1272, 1254, 1231, 1111, 1009 | 449(M$^+$) | C$_{25}$H$_{23}$NO$_5$S<br>C  H  N<br>66.52  5.23  2.96<br>66.80  5.16  3.12 |

EXAMPLE 94

11-[2-(3-Phenylureido)ethyl]thio-6,11-dihydrodibenzo-[b,e]-oxepin-2-acetic acid.0.25 hydrate (Compound 45b′)

EXAMPLE 95

11-2-[(3-Benzyl)thioureido]ethyl]thio-6,11-dihydrodibenz-[b,e]oxepin-2-carboxylic acid.0.6 toluene monohydrate (Compound 46b′)

| Pharmaceutical Preparation 1 | Tablet |
|---|---|

A tablet having the following composition is prepared in a conventional manner.

| | |
|---|---|
| Compound 1b | 200 mg |
| Lactose | 60 mg |
| Potato starch | 30 mg |
| Polyvinyl alcohol | 2 mg |
| Magnesium stearate | 1 mg |
| Tar pigment | trace |
| Pharmaceutical Preparation 2 | Powder |

Powders having the following composition are prepared in a conventional manner.

| | |
|---|---|
| Compound E-28b | 200 mg |

-continued

| Lactose | 270 mg |
|---|---|
| Pharmaceutical Preparation 3 | Syrup |

Syrup having the following composition is prepared in a conventional manner.

| Compound Ib | 200 mg |
|---|---|
| Refined sugar | 40 g |
| Ethyl p-hydroxybenzoate | 40 mg |
| Propyl p-hydroxybenzoate | 10 mg |
| Strawberry flavor | 0.1 cc |

Water is added to make the whole volume 100 cc.

According to the present invention, Compound (I) and pharmaceutically acceptable salts thereof possess a thromboxane $A_2$ ($TXA_2$)-antagonizing activity and are expected to exhibit preventive and therapeutic effects against diseases over a wide range.

While the invention has been described in detail and with reference to specific embodiments thereof, it will be apparent to one skilled in the art that various changes and modifications can be made therein without departing from the spirit and scope thereof.

What is claimed is:

1. A tricyclic compound of the formula:

$$R^B \underset{(G^B)_{g^B}}{\overset{L}{\diagup}} \overset{W-(CH_2)_n-Z-Q}{\underset{X_1-X_2}{\diagdown}} \overset{R^A}{\underset{(G^A)_{g^A}}{\diagup}}$$

wherein:

$X_1$—$X_2$ is selected from the group consisting of —$CH_2$—O— or $$-CH_2-\overset{(O)_l}{\underset{\uparrow}{S}}-;$$

(wherein $l$ represents 0, 1, or 2);

L is selected from the group consisting of —CH=CH— or —S—;

is a single or double bond;

W is selected from the group consisting of —S—, —O—, —NH—, —$CH_2$—, —NHCO— or =CH—, and the left side of each formula is bound to the tricyclic nucleus;

n is 0, 1, 2, or 3;

Z is selected from the group consisting of —$NR^1CO$—, —$NR^1SO_2$—, —$NR^1CONH$—, —$NR^1CSNH$—, —$NR^1NHCONH$—, —$NR^1NHCSNH$—, —$NR^1COO$— or —$NR^1COS$—, wherein $R^1$ is hydrogen or lower alkyl, and the right side of each formula is bound to Q;

Q is selected from the group consisting of optionally substituted, N-substituted or unsubstituted pyrrolyl, (wherein the N-substituent is lower alkyl, phenyl or benzyl), pyridyl, quinolyl or isoquinolyl wherein substitution means 1 to 3 substituents on the aromatic ring, independently selected from lower alkyl, phenyl, benzyl, halogen, triflouromethyl, nitro, $OR^2$ or $SR^2$, (wherein $R^2$ represents hydrogen, lower alkyl, phenyl or benzyl);

one of $R^A$ and $R^B$ is hydrogen and the other is —Y—M— wherein Y is selected from the group consisting of a single bond, —$CR^3R^4$—$(CH_2)_m$— and —$CR^3$=$CR^4$—$(CH^2)_m)$— and each of $R^3$ and $R^4$ are independently hydrogen or lower alkyl and m is 0, 1, 2, 3, or 4, wherein the left side of each formula is bound to the tricyclic nucleus; M is —$COOR^5$ and $R^5$ is hydrogen, lower alkyl or —$CONR^{5a}R^{5b}$ and each of $R^{5a}$ and $R^{5b}$ independently are hydrogen or lower alkyl; each of $G^A$ and $G^B$ are independently lower alkyl, halogen or $OR^6$ and $R^6$ represents hydrogen, lower alkyl, phenyl or benzyl;

each of $g^A$ and $g^B$ are independently 0, 1, 2 or 3; or a pharmaceutically acceptable salt thereof.

2. A compound according to claim 1, wherein L is —CH=CH—.

3. A compound according to claim 1, wherein one of $R^A$ and $R^B$ represents hydrogen and the other represents —Y—COOH.

4. A compound according to claim 3, wherein Y is a member selected from the group consisting of single bond, $$-CH_2-, \ -\underset{\underset{CH_3}{|}}{\overset{}{C}}H-, \ -\underset{\underset{CH_3}{|}}{\overset{\overset{CH_3}{|}}{C}}- \text{ and } -CH=CH-.$$

5. A compound according to claim 1, wherein W is —S— or =CH—.

6. A compound according to claim 1, wherein Z is —$NR^1SO_2$—.

7. A compound according to claim 6, wherein $R^1$ is hydrogen.

8. A compound according to claim 1, wherein M is —COOH; W is —S or =CH—; and Z is —$NHSO_2$—.

9. A compound according to claim 8, wherein n is 1 or 2; and L is —CH=CH—.

10. A pharmaceutical composition comprising a pharmaceutical carrier and, as an active ingredient, a therapeutically effective amount of a tricyclic compound defined in claim 1.

* * * * *

UNITED STATES PATENT AND TRADEMARK OFFICE
CERTIFICATE OF CORRECTION

PATENT NO. : 5,010,087
DATED : April 23, 1991
INVENTOR(S) : ETSUO OSHIMA, ET AL.

It is certified that error appears in the above-identified patent and that said Letters Patent is hereby corrected as shown below:

On the title page: and Column 1, line 1,

IN [54] TITLE

"$TXA_2$" should read --$TXA_2$- --.

IN [56] REFERENCES CITED

FOREIGN PATENT DOCUMENTS, "139073  8/1983  Japan" should read --139073  8/1982  Japan--.

OTHER PUBLICATIONS, "1499" should read --1499 (1977),--.

IN [57] ABSTRACT

In Formula (I), " $\begin{matrix} W \\ | \end{matrix}$ " should read -- $\begin{matrix} W \\ \| \end{matrix}$ --.

COLUMN 1

Line 1, "$TXA_2$" should read --$TXA_2$- --.

COLUMN 2

Line 34, "4,282,36" should read --4,282,365--.
Line 43, "antiasthmatic," should read --antiasthmatic--.
Line 48, "$X_1-X_2$is" should read --$X_1-X_2$ is--.

COLUMN 3

Line 26, " $\begin{matrix} W \\ | \end{matrix}$ " should read -- $\begin{matrix} W \\ \| \end{matrix}$ --.

UNITED STATES PATENT AND TRADEMARK OFFICE
CERTIFICATE OF CORRECTION

PATENT NO. : 5,010,087

DATED : April 23, 1991

INVENTOR(S) : ETSUO OSHIMA, ET AL.

It is certified that error appears in the above-identified patent and that said Letters Patent is hereby corrected as shown below:

COLUMN 3

Line 33, "----" should be deleted.
Line 43, "represents" should read -- ---- represents--.
Line 44, "—CH—," should read -- —$CH_2$—,--.
Line 46, "n is" should read --¶ n is--.
Line 47, "Z" should read --¶ Z-- and "$NR^1SO_2$—, $NR^1CONH$—," should read -- —$NR^1SO_2$—, —$NR^1CONH$—, --.
Line 48, "$NR^1CONH$—," should be deleted.
Line 49, "—NR1COO— or —NR-" should read -- —$NR^1COO$— or —$NR^1COS$— --.
Line 50, "1COS—" should be deleted.
Line 62, "that with" should be deleted.
Line 63, "onto" should read --on--.
Line 67, "one" should read --¶ one--.

COLUMN 4

Line 1, "—$CR^3R^4$—($CH_2$)m—" should read -- —$CR^3R^4$—$(CH_2)_m$— --.
Line 2, "$R^4$—(CH)m—" should read -- $R^4$—$(CH_2)_m$— --.

COLUMN 5

Line 9, "$G^AG^B$," should read --$G^A$, $G^B$,--.

COLUMN 6

Line 4, "solvent" should read --solvent.--.
Line 5, "solvent" should read --solvent.--.
Line 7, "pressure" should read --pressure.--.

UNITED STATES PATENT AND TRADEMARK OFFICE
CERTIFICATE OF CORRECTION

PATENT NO. : 5,010,087
DATED : April 23, 1991
INVENTOR(S) : ETSUO OSHIMA, ET AL.

It is certified that error appears in the above-identified patent and that said Letters Patent is hereby corrected as shown below:

COLUMN 6

Line 19, "  should read --  --.

Line 26, "wherein ," should read --wherein ----,--.

Line 30, " 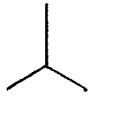 should read -- 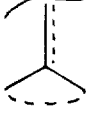 --.

COLUMN 7

Line 8, "¶ $R^7$" should read --$R^7$--.
Line 27, "room" should read --room temperature--.
Line 60, "$W_a$," should read --Wa,--.

COLUMN 8

Line 52, "$W_a$," should read --Wa,--.

COLUMN 9

Line 25, "$W_a$," should read --Wa,--.

COLUMN 10

Line 16, "[Gariel" should read --[Gabriel-- and "Merk" should read --Merck--.

UNITED STATES PATENT AND TRADEMARK OFFICE
CERTIFICATE OF CORRECTION

PATENT NO. : 5,010,087
DATED : April 23, 1991
INVENTOR(S) : ETSUO OSHIMA, ET AL.

It is certified that error appears in the above-identified patent and that said Letters Patent is hereby corrected as shown below:

COLUMN 11

Line 15, "—$NR^1SO_2$" should read -- —$NR^1SO_2$— --.

COLUMN 14

Line 13, " 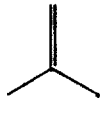 should read -- 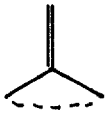 --.

COLUMN 15

Line 43, "n" should be deleted.

COLUMN 16

Line 2, "chlorine" should read --chlorine]--.
Line 3, "]" should be deleted.

COLUMN 17

Line 28, "carrier" should read --carried--.
Line 34, "Z" should read --Z is--.
Line 45, "and         ," should read --and ----,-- and "$G^B$" should read --$G^B$,--..
Line 46, "," (first occurrence) should be deleted.

Line 54, " Wb           should           -- Wb
          |            read              |:
                "                                --.

UNITED STATES PATENT AND TRADEMARK OFFICE
CERTIFICATE OF CORRECTION

PATENT NO. : 5,010,087

DATED : April 23, 1991

INVENTOR(S) : ETSUO OSHIMA, ET AL.

It is certified that error appears in the above-identified patent and that said Letters Patent is hereby corrected as shown below:

COLUMN 17

Line 62, " Wb with single bond below " should read -- Wb with double bond below --.

COLUMN 18

Line 1, " Y-shaped single bonds " should read -- Y-shaped with dashed bond --.

Line 10, ".acid" should read --acid--.
Line 18, "derivative" should read --derivatives--.
Line 23, "etc.)," should read --etc.,--.
Line 25, "ester)," should read --ester,--.

Line 55, " Y-shaped with double bond " should read -- Y-shaped with dashed bond --.

Line 60, "(Vb) (Wb = =CH—)--" should read --(Vc) (Wb = =CH—)

COLUMN 19

Line 37, "n" should read --n,--.

Line 42, " Wb with single bond " should read -- Wb with double bond --.
(both occurrences)

UNITED STATES PATENT AND TRADEMARK OFFICE
CERTIFICATE OF CORRECTION

PATENT NO. : 5,010,087

DATED : April 23, 1991

INVENTOR(S) : ETSUO OSHIMA, ET AL.

It is certified that error appears in the above-identified patent and that said Letters Patent is hereby corrected as shown below:

COLUMN 19

Line 52, " Wb | " should read -- Wb ‖ --.

Line 60, " (structure) " should read -- (structure) --.

COLUMN 20

Line 31, " Wb | " should read -- Wb ‖ --.

Line 65, " Wb($CH_2$)$_n$ | " should read -- Wb—($CH_2$)$_n$ ‖ --.

COLUMN 21

Line 44, "HC  ($CH_2$)$_n$" should read --HC〜($CH_2$)$_n$--.

COLUMN 23

Line 13, "$R^{B1}$n," should read --$R^{B1}$, n,--.

COLUMN 24

Line 13, "in" should be deleted.
Line 26, " 〜〜 " should read -- ⌒ --.
TABLE 1, "— W" should read -- ---- W--.

UNITED STATES PATENT AND TRADEMARK OFFICE
CERTIFICATE OF CORRECTION

PATENT NO. : 5,010,087
DATED : April 23, 1991
INVENTOR(S) : ETSUO OSHIMA, ET AL.

It is certified that error appears in the above-identified patent and that said Letters Patent is hereby corrected as shown below:

COLUMN 25

TABLE 1-continued, "— W" should read -- ---- W--.

COLUMN 27

TABLE 1-continued, "— W" should read -- ---- W--.

COLUMN 29

TABLE 1-continued, "— W" should read -- ---- W--.

COLUMN 31

TABLE 1-continued, "— W" should read -- ---- W--.

COLUMN 33

TABLE 1-continued, "— W" should read -- ---- W--.

COLUMN 35

TABLE 1-continued, "— W" should read -- ---- W--.

COLUMN 37

Line 1, " W     should     --  W
           |      read             |¦
              "                         --.

Line 9, "$R^A$, $R^B$," should read --$R^{A1}$, $R^{B1}$,-- and
        "Wb, $R^1$," should read --Z, W,--.
Line 11, "are" should read --is--.

UNITED STATES PATENT AND TRADEMARK OFFICE
CERTIFICATE OF CORRECTION

PATENT NO. : 5,010,087
DATED : April 23, 1991
INVENTOR(S) : ETSUO OSHIMA, ET AL.

It is certified that error appears in the above-identified patent and that said Letters Patent is hereby corrected as shown below:

COLUMN 38

Line 17, "amino]9" should read --amino]--.
Line 49, "amino]9" should read --amino]--.
Line 67, "Chemica" should read --Chemical--.

COLUMN 39

Line 11, "before" should read --for--.
Line 52, "it is" should read --they are--.
Line 65, "togethwer" should read --together--.

COLUMN 40

Line 33, "pepper" should read --peppermint,--.
Line 34, "mint," should be deleted.
Line 52, "to" should read --to be--.

COLUMN 41

TABLE 5, "—X°" should read -- ---- X°--.
Line 64, "cm-1):" should read --$cm^{-1}$):--.
Line 67, "and," should read --, and--.

COLUMN 42

Line 52, "cm-1):" should read --$cm^{-1}$):--.

COLUMN 44

Line 24, "g):" should read --g)--.
Line 39, "diStilled" should read --distilled--.

UNITED STATES PATENT AND TRADEMARK OFFICE
CERTIFICATE OF CORRECTION

PATENT NO. : 5,010,087
DATED : April 23, 1991
INVENTOR(S) : ETSUO OSHIMA, ET AL.

It is certified that error appears in the above-identified patent and that said Letters Patent is hereby corrected as shown below:

COLUMN 45

Line 10, "and," should read --, and--.
Line 60, "-$SO_2CH3$;" should read -- -$SO_2CH_3$;--.

COLUMN 46

Line 2, "pressure" should read --pressure.--.

COLUMN 47

Line 12, "$Cm^{-1}$):" should read --$cm^{-1}$):--.
Line 51, "olate." should read --olate (Compound q)--.
Line 53, "(Compound q)" should be deleted.

COLUMN 48

Line 12, "and," should read --, and--.
Line 20, "and," should read --, and--.
Line 40, "acetate" should read --acetate.--.
Line 58, "pressure" should read --pressure.--.

COLUMN 49

Line 31, "pressure" should read --pressure.--.
Line 46, "The" should read --¶ The--.
Line 48, "and," should read --, and--.
Line 59, "acetate =" should be deleted.

COLUMN 50

Line 32, "pressure" should read --pressure.--.
Line 42, "wa" should read --was--.

UNITED STATES PATENT AND TRADEMARK OFFICE
CERTIFICATE OF CORRECTION

PATENT NO. : 5,010,087

DATED : April 23, 1991

INVENTOR(S) : ETSUO OSHIMA, ET AL.

It is certified that error appears in the above-identified patent and that said Letters Patent is hereby corrected as shown below:

COLUMN 52

Line 2, "tead" should read --ted--.
    Line 9, "tead" should read --ted--.
    Line 59, "6a):" should read --6a)--.

COLUMN 55

TABLE 6-1, "2.72" should read --2.72- -- and "2.83" should read --2.83- --.

COLUMN 56

TABLE 6-1, "m/z" should read --m/Z--.

COLUMN 57

TABLE 6-1-continued, "2H," should read --2H),--.

COLUMN 58

TABLE 6-1-continued, "m/z" should read --m/Z--.

COLUMN 60

Line 43, "acid 0.2" should read --acid.0.2--.

COLUMN 62

TABLE 6-2, "m/z" should read --m/Z-- and "1H)," should read --1H)--.

UNITED STATES PATENT AND TRADEMARK OFFICE
CERTIFICATE OF CORRECTION

PATENT NO. : 5,010,087

DATED : April 23, 1991

INVENTOR(S) : ETSUO OSHIMA, ET AL.

It is certified that error appears in the above-identified patent and that said Letters Patent is hereby corrected as shown below:

COLUMN 63

TABLE 6-2-continued, "m/z" should read --m/Z-- and "7.15" should read --7.15- -- (both occurrences).

COLUMN 66

TABLE 6-3, "m/z" should read --m/Z--.
TABLE 6-4, "m/z" should read --m/Z-- and "718" should read --7.18--.

COLUMN 68

TABLE 6-5, "m/z" should read --m/Z--.

COLUMN 70

TABLE 6-5-continued, "m/z" should read --m/Z--.
Lines 20-27, "          EXAMPLE
                b)
                64
                b)
                65
                b)
                66
                4,10   "   should be deleted.

TABLE 6-6, "m/z" should read --m/Z--.

COLUMN 72

TABLE 6-6-continued, "m/z" should read --m/Z--.
Line 35, "Example 63" should be a centered heading.
TABLE 6-7, "m/z" should read --m/Z--.

UNITED STATES PATENT AND TRADEMARK OFFICE
CERTIFICATE OF CORRECTION

PATENT NO. : 5,010,087

DATED : April 23, 1991

INVENTOR(S) : ETSUO OSHIMA, ET AL.

It is certified that error appears in the above-identified patent and that said Letters Patent is hereby corrected as shown below:

COLUMN 74

TABLE 6-7-continued, "m/z" should read --m/Z--.
Line 33, "Methyl11" should read --Methyl ¶ 11--.

COLUMN 76

TABLE 6-8, "m/z" should read --m/Z--.

COLUMN 78

TABLE 6-8-continued, "m/z" should read --m/Z--.

COLUMN 80

TABLE 6-9, "m/z" should read --m/Z--;
"1H), 1001" should read --1H),--; and
"1232, 1133," should read --1232, 1133, 1001--.

COLUMN 82

TABLE 6-9-continued, "m/z" should read --m/Z--.
TABLE 6-10, "m/z" should read --m/Z--.

COLUMN 84

TABLE 6-10-continued, "m/z" should read --m/Z--.
TABLE 6-11, "m/z" should read --m/Z--.
Line 64, "Powders" should read --Powder-- and
"are" should read --is--.

UNITED STATES PATENT AND TRADEMARK OFFICE
CERTIFICATE OF CORRECTION

PATENT NO. : 5,010,087
DATED : April 23, 1991
INVENTOR(S) : ETSUO OSHIMA, ET AL.

It is certified that error appears in the above-identified patent and that said Letters Patent is hereby corrected as shown below:

COLUMN 85

Line 48, "is" should read -- ---- is--.

COLUMN 86

Line 11, "flouromethyl," should read --fluoromethyl,--.
Line 22, "are" should read --is--.
Line 23, "are" should read --is--.
Line 26, "are" should read --is--.
Line 49, "—S" should read -- —S— --

Signed and Sealed this

Fourteenth Day of June, 1994

Attest:

BRUCE LEHMAN

*Attesting Officer*  *Commissioner of Patents and Trademarks*